(12) United States Patent
Corradini et al.

(10) Patent No.: US 11,951,102 B2
(45) Date of Patent: *Apr. 9, 2024

(54) METHODS AND COMPOSITIONS FOR TREATING RETINA-ASSOCIATED DISEASE USING CCR3-INHIBITORS

(71) Applicant: ALKAHEST INC., San Carlos, CA (US)

(72) Inventors: Laura Corradini, Ingelheim am Rhein (DE); Sam Jackson, San Carlos, CA (US); Karoly Nikolich, San Carlos, CA (US)

(73) Assignee: ALKAHEST INC., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/170,384

(22) Filed: Feb. 16, 2023

(65) Prior Publication Data
US 2024/0024305 A1 Jan. 25, 2024

Related U.S. Application Data

(63) Continuation of application No. 16/603,084, filed as application No. PCT/US2018/026091 on Apr. 4, 2018, now Pat. No. 11,590,118.

(60) Provisional application No. 62/482,134, filed on Apr. 5, 2017.

(51) Int. Cl.
| | | |
|---|---|---|
| *A61K 31/4545* | (2006.01) | |
| *A61K 9/20* | (2006.01) | |
| *A61K 9/28* | (2006.01) | |
| *A61K 31/5377* | (2006.01) | |
| *A61K 45/06* | (2006.01) | |

(52) U.S. Cl.
CPC ........ *A61K 31/4545* (2013.01); *A61K 9/2018* (2013.01); *A61K 9/2027* (2013.01); *A61K 9/2054* (2013.01); *A61K 9/2059* (2013.01); *A61K 9/2813* (2013.01); *A61K 9/282* (2013.01); *A61K 9/284* (2013.01); *A61K 9/2853* (2013.01); *A61K 9/2866* (2013.01); *A61K 31/5377* (2013.01); *A61K 45/06* (2013.01); *C07B 2200/13* (2013.01)

(58) Field of Classification Search
CPC ............ A61K 31/4545; A61K 31/5377; A61K 45/06; A61K 9/2018; A61K 9/2027; A61K 9/2054; A61K 9/2059; A61K 9/2813; A61K 9/282; A61K 9/284; A61K 9/2853; A61K 9/2866; C07B 2200/13
See application file for complete search history.

(56) References Cited

U.S. PATENT DOCUMENTS

| | | |
|---|---|---|
| 8,278,302 B2 | 10/2012 | Grundl et al. |
| 8,653,075 B2 | 2/2014 | Grundl et al. |
| 8,680,280 B2 | 3/2014 | Duran et al. |
| 8,742,115 B2 | 6/2014 | Frank et al. |
| RE45,323 E | 1/2015 | Grundl et al. |
| 9,233,950 B2 | 1/2016 | Frank et al. |
| 2011/0268723 A1 | 11/2011 | Ambati |
| 2013/0261153 A1 | 10/2013 | Nivens et al. |
| 2013/0266646 A1 | 10/2013 | Fetscher et al. |
| 2014/0335083 A1 | 11/2014 | Adamson et al. |
| 2015/0105371 A1 | 4/2015 | Frank et al. |
| 2016/0081998 A1 | 3/2016 | Nivens et al. |
| 2019/0105314 A1 | 4/2019 | Braithwaite et al. |

FOREIGN PATENT DOCUMENTS

| | | |
|---|---|---|
| CL | 2019002847 A1 | 2/2020 |
| CN | 104220073 A | 12/2014 |
| EP | 3606525 A1 | 2/2020 |
| JP | 2015-500221 A | 1/2015 |
| RU | 2002112800 A | 3/2004 |
| WO | 2010/115836 A1 | 10/2010 |
| WO | 2012/045803 A1 | 4/2012 |
| WO | 2013/149926 A1 | 10/2013 |
| WO | 2013/149986 A1 | 10/2013 |
| WO | 2013/149987 A1 | 10/2013 |
| WO | 2018/187503 A1 | 10/2018 |

OTHER PUBLICATIONS

"What is Macular Degeneration?" American Macular Degeneration Foundation. First available to public on: Mar. 15, 2006. Accessed Jan. 9, 2022. Available at: < https://www.macular.org/what-macular-degeneration > . (Year: 2006).
Ambati et al., Mechanisms of age-related macular degeneration, Neuron, 75(1):26-39 (2012).
Bhisitkul et al., Macular atrophy progression and 7-year vision outcomes in subjects from the Anchor, Marina, and Horizon studies: the Seven-Up study, Am. J. Ophthalmol., 159(5):915-924 (2015).
Bokinni et al., Performance of a computerised visual acuity measurement device in subjects with age-related macular degeneration: comparison with gold standard ETDRS chart measurements, Eye(Lond), 29(8):1085-1091 (2015).
Cho et al., Aflibercept for exudative AMD with persistent fluid on ranibizumab and/or bevacizumab, Br. J. Ophthalmol., 97(8):1032-5 (2013).
Desai et al., The Future of Treatment for Wet AMD, Curr. Opthalmol. Rep., 5:93-97 (2017).

(Continued)

*Primary Examiner* — Timothy R Rozof
(74) *Attorney, Agent, or Firm* — MARSHALL, GERSTEIN & BORUN LLP

(57) ABSTRACT

Methods of improving visual endpoints related to retina-associated disease with CCR3 modulating agents are provided. An example of such an endpoint is visual acuity. Retina-associated diseases upon which visual acuity and other visual endpoints may be improved include retinopathy of prematurity, age-related macular degeneration, central retinal vein occlusion, and diabetic retinopathy.

26 Claims, 5 Drawing Sheets

(56) References Cited

OTHER PUBLICATIONS

Fujimoto et al., Optical coherence tomography: an emerging technology for biomedical imaging and optical biopsy, Neoplasia, 2(1-2):9-25 (2000).
Heier et al., Intravitreal aflibercept (VEGF trap-eye) in wet age-related macular degeneration, Ophthalmology, 119(12):2537-2548 (2012).
International Application No. PCT/US2018/026091, International Search Report and Written Opinion, dated Jul. 6, 2018.
International Preliminary Report on Patentability for corresponding International Application No. PCT/US2018/026091, dated Oct. 17, 2019.
Jager et al., Age-related macular degeneration, N. Engl. J. Med., 358(24):2606-2617 (2008).
Keane et al., Evaluation of optical coherence tomography retinal thickness parameters for use in clinical trials for neovascular age-related macular degeneration, Investigative Ophthalmology & Visual Science, 50(7):3378-3385 (2009).
Levenson et al., Chapter 111: Visual Acuity Change, Clinical Methods: The History, Physical and Laboratory Examinations. 3rd edition:553-555 (1990).
Li et al., CCR3 and Choroidal Neovascularization, PLoS ONE, 6(2):e17106 (2011).
Mizutani et al., Suppression of laser-induced choroidal neovascularization by a CCR3 antagonist, Invest Ophthalmol. Vis. Sci., 54:1564-1572 (2013).
Nagai et al., Novel CCR3 antagonists are effective mono-and combination inhibitors of choroidal neovascular growth and vascular permeability, The American Journal of Pathology, 185(9):2534-2549 (2015).
Nagineni et al., CCR-3 ligands, CCL-5, 11 and 26, are induced in human retinal cels by inflammatory cytokines: Potential role in ate-related macular degeneration, The Faseb J. Federation of American Soc. Exp. Biol., 25:1 (2011).
Nagineni et al., Inflammatory cytokines induce expression of chemokines by human retinal cells: role in chemokine receptor mediated age-related macular degeneration, Aging and Disease, 6(6):444-455 (2015).
Papadopoulou et al., Intravitreal ranibizumab may induce retinal arteriolar vasoconstriction in patients with neovascular age-related macular degeneration, Ophthalmology, 116(9):1755-1761 (2009).
Rosenfeld et al., Ranibizumab for neovascular age-related macular degeneration, N. Engl. J. Med., 355(14):1419-1431 (2006).
Sacu et al., Response of retinal vessels and retrobulbar hemodynamics to intravitreal anti-VEGF treatment in eyes with branch retinal vein occlusion, Invest. Ophthalmol. Vis. Sci., 52(6):3046-3050 (2011).
Salcedo et al., Eotaxin (CCL11) induces in vivo angiogenic responses by human CCR3 + endothelial cells, J. Immunol., 166:7571-7578 (2001).
Taiwanese Official Action dated Mar. 10, 2022; Taiwanese Patent Application No. 107112125.
Takeda et al., CCR3 is a therapeutic and diagnostic target for neovascular age-related macular degeneration, Nature, 460(7252):225-230 (2009).
Wang et al., Diabetic Retinopathy: Pathophysiology and Treatments, Int. J. Mol. Sci., 19(6):1816 (2018).
Wang et al., Upregulation of CCR3 by age-related stresses promotes choroidal endothelial cell migration via VEGF-dependent and-independent signaling, Investigative Ophthalmology & Visual Science, 52(11) (2011).

Figure 1

| Assay | Human CCR3 | Monkey CCR3 | Mouse CCR3 | Rat CCR3 | Canine CCR3 |
|---|---|---|---|---|---|
| Cell line receptor binding Ki (nM) | 3 | | 124 | 1489 | |
| Cell line $Ca^{2+}$ influx $IC_{50}$ (nM) | 1 | | | 1155 | |
| Cell line chemotaxis $IC_{50}$ (nM) | 23 | 25 | 485 | | |
| Eosinophil chemotaxis $IC_{50}$ (nM) | 65 | | | | |
| Eosinophil $Ca^{2+}$ influx $IC_{50}$ (nM) | | | | | |
| Eosinophil CCR3 internalization $IC_{50}$ (nM) | 27 | | | | |
| Eosinophil shape change $IC_{50}$ (nM) | 4 | 3 | | | |
| Eosinophil whole blood shape change $IC_{50}$ (nM) | 31 | 2 | | | 53-30000 |

Table 15.2.2:1 Descriptive Statistics Over Time For Neovascular Leakage Area (mm²) As Assessed By PA - Treated Set (OC)

| | | | Total | | | |
|---|---|---|---|---|---|---|
| | N | Mean | SD | Min | Median | Max |
| Absolute Values [mm²] | | | | | | |
| Baseline | 13 | 6.7 | 6.8 | 1.0 | 4.5 | 21.5 |
| Visit 4 | 13 | 4.9 | 4.6 | 0.9 | 3.7 | 17.7 |
| Visit 6 | 11 | 4.9 | 4.7 | 1.0 | 3.7 | 17.3 |
| Visit 8 - FUP | 5 | 9.5 | 7.2 | 3.3 | 7.1 | 21.2 |
| Change From Baseline [mm²] | | | | | | |
| Visit 4 | 12 | -2.0 | 3.4 | -11.1 | -0.3 | 1.3 |
| Visit 6 | 10 | -0.7 | 1.4 | -4.2 | -0.6 | 1.2 |
| Visit 8 - FUP | 5 | 0.7 | 1.3 | -0.5 | 0.3 | 2.7 |

Figure 4

METHODS AND COMPOSITIONS FOR TREATING RETINA-ASSOCIATED DISEASE USING CCR3-INHIBITORS

CROSS-REFERENCE TO RELATED APPLICATIONS

This application claims priority to U.S. Patent Application No. 62/482,134, filed Apr. 5, 2017, which is hereby incorporated by reference.

TECHNICAL FIELD OF THE INVENTION

The invention relates to materials and methods for improving visual acuity in a subject in need thereof.

BACKGROUND OF THE INVENTION

Among the variety of retinal-associated diseases, there are those that manifest themselves early in life as well as those that manifest themselves in connection with aging. An example of the former type of disease is retinopathy of prematurity (ROP). Examples of age-related retina-associated diseases include: age-related macular degeneration (AMD) which is the most common degenerative disease of the macula; central retinal vein occlusion (CRVO), and diabetic retinopathy. Untreated, retina-associated disease can lead to legal blindness.

AMD is the leading cause of irreversible blindness in people 50 years of age or older in the developed world. (Jager, R. et al., The New England Journal of Medicine, 358(2606-17), 2008). AMD is a term that is used to describe a family of diseases that are all characterized by a progressive loss of central vision associated with abnormalities of Bruch's membrane, the choroid, the neural retina and/or the retinal pigment epithelium. In the early stages of AMD, which is often referred to as age-related maculopathy (ARM), accumulation of drusen (biochemical byproducts of the photoreceptor cells which accumulate in Bruch's membrane which are categorized by their appearance) and disturbances of the retinal pigment epithelium (RPE) are often observed.

AMD that becomes clinically advanced is classified into two forms—"dry," nonexudative or atrophic AMD and exudative "wet" or neovascular AMD. Dry AMD occurs in approximately 15%, and wet AMD in approximately 10%, of AMD patients. Wet AMD is considered the more debilitating form of AMD and is thought to be caused by the growth of abnormal choroidal neovascular membranes (CNVM). These new blood vessels grow from the choriocapillaris, growing under the RPE or retina, and leak serum and blood. This fluid accumulates in the sub-RPE and subretinal spaces along with the neurosensory retina, and in turn causes measurable thickening of the macula. If the fovea becomes involved with the CNVM, the resulting edema and hemorrhage can significantly impair visual acuity (VA), leading to dramatic vision loss.

Estimates suggest that about 10% of those aged 65-74 years old and 30% of those aged 75-85 years old, exhibit signs of AMD. The current standard of care for wet AMD is anti-angiogenic therapies such as ranibizumab (Lucentis®) and aflibercept (Eylea®) by intravitreal (IVT) administration (i.e. injection directly into the eye). Such therapies target vascular endothelial growth factors (VEGF, VEGF-A) and their angiogenic-promoting properties. However, monthly IVT injections have been associated with the adverse effects of geographic atrophy. (Desai, S J, et al., Curr Opthalmol. Rep. (Feb. 1, 2017)). Currently, there exist no effective, less-invasive therapies, underscoring an unmet need for an orally-administered, non-anti-VEGF based therapy for treating AMD. In addition to alleviating and reversing the symptoms and dramatic detrimental effects on the vision of patients, such a therapy would have the added benefit of increased compliance. IVT injections bear increased risk to patients and are burdensome to both patients and caregivers.

The mechanistic basis of anti-VEGF therapies also bears risk. VEGF, particularly VEGF-A has a physiologic cytoprotective role in the retina. Modulating VEGF expression and activity can be toxic to multiple cell types. (Ambati, J., et al., Neuron 75(1):26-39, July 2012). Evidence shows that anti-VEGF-A therapy can also contribute to physiologic alterations in the retinal vasculature in the short-term as well as RPE toxicity in the long-term. (Papadopoulou D N, et al., Ophthalmology 116(9):1755-61 (2009); Sacu S, et al., Invest. Ophthalmol. Vis. Sci. 52(6):3046-50 (2011); and Rofagha S, et al. Am. J. Ophthalmol. 159(5):915-24 (2015)).

In contrast, treatment with C-C motif chemokine receptor 3 (CCR3) antagonists occurs without altering levels of VEGF-A or broadly affecting the immune system. In addition, CCR3 antagonists can be in the form of small, organic molecules, and can be prepared in oral formulations. The compounds, co-crystals, salts, and formulations of the invention provide for highly specific and potent small molecule modulators of the human C-C chemokine receptor type 3, which is the principal receptor for eotaxin-1. The CCR3/eotaxin axis is a key chemotactic factor for eosinophils, mast cells, and (in the retinal context) endothelial cells of the retinal vasculature, and studies on rodents have shown promise in alleviating retinal disease-associated neovascularization.

Despite this promise, there has been a failure in the industry to develop a CCR3 antagonist for human treatment of retina-associated disease. However, the compounds, co-crystals, salts, and formulations disclosed herein, which specifically modulate/antagonize CCR3, are effective at improving the visual acuity of a significant number of subjects, even while effects on neovascularization are insignificant.

SUMMARY OF THE INVENTION

Methods of treating patients for retinal-associated diseases are provided, including dry and wet age-associated macular degeneration, central retinal vein occlusion, retinopathy of prematurity, and diabetic retinopathy. A method of improving visual acuity in a subject (such as a subject diagnosed with a retina-associated disease) is provided. Aspects of the methods include modulation of CCR3, the principal receptor of CCL11/eotaxin-1 through the administration of an effective amount of CCR3 antagonists of the invention. The methods include administering effective therapeutic doses of CCR3 antagonists (e.g., a compound of Formula 1 described herein) to subjects or patients as well as monitoring for specific clinical endpoints.

BRIEF DESCRIPTION OF THE DRAWINGS

FIG. 1 is a table of potency and species selectivity for an investigational product of the invention.

FIG. 4 is a table of descriptive statistics with respect to neovascular leakage over the clinical trial timeline described in FIG. 2.

DETAILED DESCRIPTION OF THE INVENTION

Figure 2:
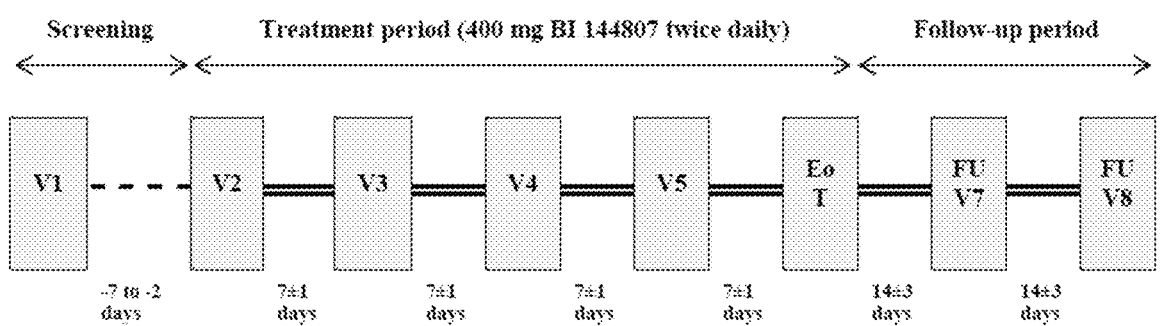
FIG. 2 depicts the overall clinical trial design and plan using the investigational product of the invention including screening, treatment, and follow-up periods.

Methods of treating symptoms of retina-related disease are provided, the method comprising administering compounds from the formulae discussed below. An embodiment of the invention comprises a method of improving visual acuity in subjects with retina-associated disease, the method comprising administering a therapeutically effective amount of a compound from the chemical formulae discussed below. Additional embodiments include administering a therapeutically effective amount of a compound wherein the compound is in the form of the co-crystals or salts of the formulae discussed below. Further embodiments of the invention include administering a therapeutically effective amount of a compound wherein the compound is in the form of individual optical isomers, a mixture of the individual enantiomers, a racemate or enantiomerically pure compounds. Additional embodiments of the invention also include administering a therapeutically effective amount of a compound wherein the compound is in the form of the pharmaceutical compositions and formulations further discussed below.

Another embodiment of the invention comprises a method of improving visual acuity in subjects with retina-associated disease, the method comprising administering a therapeutically effective amount of a combination of a compound from the chemical formulae discussed below in conjunction with the current standard of care in the United States for retina-associated disease. Further embodiments of the invention include administering a therapeutically effective amount of a combination of a compound from the chemical formulae discussed below in conjunction with an anti-VEGF-A therapy such as antibodies to VEGF-A (e.g. ranibizumab (Lucentis®), bevacizumab (Avastin®), recombinant fusion proteins that bind one or more VEGF receptor types (e.g. aflibercept, Eylea®), or small organic molecules which bind either VEGF-A or one of its receptor types (e.g. VEGF receptor 1 or 2).

By "treatment" it is meant that at least an amelioration of one or more symptoms associated with retina-related disease afflicting the patient, where amelioration is used in a broad sense to refer to at least a reduction in the magnitude of a parameter, e.g., a symptom associated with the disease being treated. As such, treatment also includes situations where a pathological condition, or at least symptoms associated therewith, is completely inhibited, e.g., prevented from happening, or stopped, e.g., terminated, such that patient no longer suffers from the impairment, or at least the symptoms that characterize the impairment. In some instances, "treatment", "treating" and the like refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" may be any treatment of a disease in a subject, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may result in a variety of different physical manifestations, e.g., modulation in gene expression, increased neurogenesis, rejuvenation of tissue or organs, etc. Treatment of ongoing disease, where the treatment stabilizes or reduces the undesirable clinical symptoms of the patient, occurs in some embodiments. Such treatment may be performed prior to complete loss of function in the affected tissues. The subject therapy may be administered during the symptomatic stage of the disease, and in some cases after the symptomatic stage of the disease.

In some instances, the subject is a mammal. Mammalian species that may be treated with the present methods include canines and felines; equines; bovines; ovines; etc., and primates, including humans. The subject methods, compositions, and reagents may also be applied to animal models, including small mammals, e.g., murine, lagomorpha, etc., for example, in experimental investigations.

a. Compounds

The methods of the invention further comprise administration to a subject of the compounds that follow. In the groups, radicals, or moieties defined in this "Compounds" section the number of carbon atoms is often specified preceding the group, for example, $C_{1-6}$ alkyl means an alkyl group or radical having 1 to 6 carbon atoms. In general, for groups comprising two or more subgroups which are disclosed in this "Compounds" section, the last named group is the radical attachment point, for example, "thioalkyl" means a monovalent radical of the formula HS-Alk-. Unless otherwise specified below, conventional definitions of terms control and conventional stable atom valences are presumed and achieved in all formulas and groups.

An embodiment of the invention further comprises administration to a subject of the compounds of formula 1, wherein

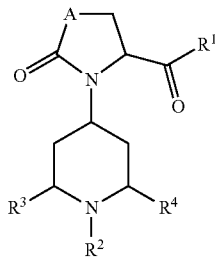

Formula 1

A is $CH_2$, O or N—$C_{1-6}$-alkyl;
$R^1$ is selected from $NHR^{1.1}$, $NMeR^{1.1}$; $NHR^{1.2}$, $NMeR^{1.2}$; $NHCH_2$—$R^{1.3}$—;
NH—$C_{3-6}$-cycloalkyl, whereas optionally one carbon atom is replaced by a nitrogen atom, whereas the ring is optionally substituted with one or two residues selected from the group consisting of $C_{1-6}$-alkyl, O—$C_{1-6}$-alkyl, $NHSO_2$-phenyl, NHCONH-phenyl, halogen, CN, $SO_2$—$C_{1-6}$-alkyl, COO—$C_{1-6}$-alkyl; a $C_{9\ or\ 10}$-bicyclic-ring, whereas one or two carbon atoms are replaced by nitrogen atoms and the ring system is bound via a nitrogen atom to the basic structure of formula 1 and whereas the ring system is optionally substituted with one or two residues selected from the group consisting of $C_{1-6}$-alkyl, COO—$C_{1-6}$-alkyl, $C_{1-6}$-haloalkyl, O—$C_{1-6}$-alkyl, $NO_2$, halogen, CN, $NHSO_2$—$C_{1-6}$-alkyl, methoxy-phenyl; a group selected from NHCH(pyridinyl)$CH_2$COO—$C_{1-6}$-alkyl, NHCH($CH_2$O—$C_{1-6}$-alkyl)-benzoimidazolyl, optionally substituted with halogen or CN; or 1-aminocyclopentyl, optionally substituted with methyl-oxadiazole;

$R^{1.1}$ is phenyl, optionally substituted with one or two residues selected from the group consisting of $C_{1-6}$-alkyl, $C_{2-6}$-alkenyl, $C_{2-6}$-alkynyl, $C_{1-6}$-haloalkyl, $C_{1-6}$-alkylene-OH, $C_{2-6}$-alkenylene-OH, $C_{2-6}$-alkynylene-OH, $CH_2CON(C_{1-6}$-alkyl)$_2$, $CH_2NHCONH$—$C_{3-6}$-cycloalkyl, CN, CO-pyridinyl, $CONR^{1.1.1}R^{1.1.2}$, COO—$C_{1-6}$-alkyl, $N(SO_2$—$C_{1-6}$-alkyl)($CH_2CON$ $(C_{1-4}$-alkyl)$_2$)O—$C_{1-6}$-alkyl, O-pyridinyl, $SO_2$—$C_{1-6}$-alkyl, $SO_2$—$C_{1-6}$-alkylen-OH, $SO_2$—$C_{3-6}$-cycloalkyl, $SO_2$-piperidinyl, $SO_2NH$—$C_{1-6}$-alkyl, $SO_2N(C_{1-6}$-alkyl)$_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl and =O;

$R^{1.1.1}$ is selected from H, $C_{1-6}$-alkyl, $C_{3-6}$-cycloalkyl, $C_{1-6}$-haloalkyl, $CH_2CON(C_{1-6}$-alkyl)$_2$, $CH_2CO$-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;

$R^{1.1.2}$ H, $C_{1-6}$-alkyl, $SO_2C_{1-6}$-alkyl; or $R^{1.1.1}$ and $R^{1.1.2}$ together are forming a four-, five- or six-membered carbocyclic ring, optionally containing one N or O, replacing a carbon atom of the ring, optionally substituted with one or two residues selected from the group consisting of $C_{1-6}$-alkyl, $C_{1-4}$-alkylene-OH, OH, =O; or $R^{1.1}$ is phenyl, wherein two adjacent residues are together forming a five- or six-membered carbocyclic aromatic or non-aromatic ring, optionally containing independently from each other one or two N, S, or $SO_2$, replacing a carbon atom of the ring, wherein the ring is optionally substituted with $C_{1-4}$-alkyl or =O;

$R^{1.2}$ is selected from heteroaryl, optionally substituted with one or two residues selected from the group consisting of $C_{1-6}$-alkyl, $C_{2-6}$-alkenyl, $C_{2-6}$-alkynyl, $C_{3-6}$-cycloalkyl, $CH_2COO$—$C_{1-6}$-alkyl, $CONR^{1.2.1}R^{1.2.2}$, $COR^{1.2.3}$, COO—$C_{1-6}$-alkyl, $CONH_2$, O—$C_{1-6}$-alkyl, halogen, CN, $SO_2N(C_{1-6}$-alkyl)$_2$ or heteroaryl optionally substituted with one or two residues selected from the group consisting of $C_{1-6}$-alkyl; heteroaryl, optionally substituted with a five- or six-membered carbocyclic non-aromatic ring containing independently from each other two N, O, S, or $SO_2$, replacing a carbon atom of the ring; a aromatic or non-aromatic $C_{9\ or\ 10}$-bicyclic-ring, whereas one or two carbon atoms are replaced by N, O or S each optionally substituted with one or two residues selected from the group consisting of N $(C_{1-6}$-alkyl)$_2$, CONH—$C_{1-6}$-alkyl, =O; a heterocyclic non-aromatic ring, optionally substituted with pyridinyl; 4,5-dihydro-naphtho[2,1-d]thiazole, optionally substituted with NHCO—$C_{1-6}$-alkyl, $R^{1.2.1}$ is selected from H, $C_{1-6}$-alkyl, $C_{1-6}$-alkylene-$C_{3-6}$-cycloalkyl, $C_{1-4}$-alkylene-phenyl, $C_{1-4}$-alkylene-furanyl, $C_{3-6}$-cycloalkyl, $C_{1-4}$-alkylene-O—$C_{1-4}$-alkyl, $C_{1-6}$-haloalkyl or a five- or six-membered carbocyclic non-aromatic ring, optionally containing independently from each other one or two N, O, S, or $SO_2$, replacing a carbon atom of the ring, optionally substituted with 4-cyclopropylmethyl-piperazinyl $R^{1.2.2}$ is selected from H, $C_{1-6}$-alkyl;

$R^{1.2.3}$ is selected from a five- or six-membered carbocyclic non-aromatic ring, optionally containing independently from each other one or two N, O, S, or $SO_2$, replacing a carbon atom of the ring;

$R^{1.3}$ is selected from phenyl, heteroaryl or indolyl, each optionally substituted with one or two residues selected from the group consisting of $C_{1-6}$-alkyl, $C_{3-6}$-cycloalkyl, O—$C_{1-6}$-alkyl, O—$C_{1-6}$-haloalkyl, phenyl, heteroaryl;

$R^2$ is selected from the group consisting of $C_{1-6}$-alkylene-phenyl, $C_{1-6}$-alkylene-naphthyl, and $C_{1-6}$-alkylene-heteroaryl; each optionally substituted with one, two or three residues selected from the group consisting of $C_{1-6}$-alkyl, $C_{1-6}$-haloalkyl, O—$C_{1-6}$-alkyl, O—$C_{1-6}$-haloalkyl, halogen;

$R^3$ is selected from H, $C_{1-6}$-alkyl;

$R^4$ is selected from H, $C_{1-6}$-alkyl; or $R^3$ and $R^4$ together are forming a $CH_2$—$CH_2$ group.

Another embodiment of the present invention further comprises administration to a subject of the compounds of formula 1 (above), wherein A is $CH_2$, O or N—$C_{1-4}$-alkyl;

$R^1$ is selected from $NHR^{1.1}$, $NMeR^{1.1}$; $NHR^{1.2}$, $NMeR^{1.2}$; $NHCH_2$—$R^{1.3}$; wherein $R^{1.1}$ is phenyl, optionally substituted with one or two residues selected from the group consisting of $C_{1-6}$-alkyl, $C_{2-6}$-alkenyl, $C_{2-6}$-alkynyl, $C_{1-6}$-haloalkyl, $C_{1-6}$-alkylene-OH, $C_{2-6}$-alkenylene-OH, $C_{2-6}$-alkynylene-OH, $CH_2CON(C_{1-6}$-alkyl)$_2$, $CH_2NHCONH$—$C_{3-6}$-cycloalkyl, CN, CO-pyridinyl, $CONR^{1.1.1}R^{1.1.2}$, COO—$C_{1-6}$-alkyl, $N(SO_2$—$C_{1-6}$-alkyl)($CH_2CON(C_{1-4}$-alkyl)$_2$) O—$C_{1-6}$-alkyl, O-pyridinyl, $SO_2$—$C_{1-6}$-alkyl, $SO_2$—$C_{1-6}$-alkylen-OH, $SO_2$—$C_{3-6}$-cycloalkyl, $SO_2$-piperidinyl, $SO_2NH$—$C_{1-6}$-alkyl, $SO_2N(C_{1-6}$-alkyl)$_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl, =O;

$R^{1.1.1}$ is selected from H, $C_{1-6}$-alkyl, $C_{3-6}$-cycloalkyl, $C_{1-6}$-haloalkyl, $CH_2CON(C_{1-6}$-alkyl)$_2$, $CH_2CO$-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;

$R^{1.1.2}$ is selected from H, $C_{1-6}$-alkyl, $SO_2C_{1-6}$-alkyl; or $R^{1.1.1}$ and $R^{1.1.2}$ together are forming a four-, five- or six-membered carbocyclic ring, optionally containing one N or O, replacing a carbon atom of the ring, optionally substituted with one or two residues selected from the group consisting of $C_{1-6}$-alkyl, $C_{1-4}$-alkylene-OH, OH, =O; or $R^{1.1}$ is selected from phenyl, wherein two adjacent residues are together forming a five- or six-membered carbocyclic aromatic or non-aromatic ring, optionally containing independently from each other one or two N, S, or $SO_2$, replacing a carbon atom of the ring, wherein the ring is optionally substituted with $C_{1-4}$-alkyl or =O;

$R^{1.2}$ is selected from heteroaryl, optionally substituted with one or two residues selected from the group consisting of $C_{1-6}$-alkyl, $C_{2-6}$-alkenyl, $C_{2-6}$-alkynyl, $C_{3-6}$-cycloalkyl, $CH_2COO$—$C_{1-6}$-alkyl, $CONR^{1.2.1}R^{1.2.2}$, $COR^{1.2.3}$, $COO$—$C_{1-6}$-alkyl, $CONH_2$, $O$—$C_{1-6}$-alkyl, halogen, CN, $SO_2N(C_{1-4}$-alkyl$)_2$ or heteroaryl optionally substituted with one or two residues selected from the group consisting of $C_{1-6}$-alkyl; heteroaryl, optionally substituted with a five- or six-membered carbocyclic non-aromatic ring containing independently from each other two N, O, S, or $SO_2$, replacing a carbon atom of the ring; wherein $R^{1.2.1}$ is selected from H, $C_{1-6}$-alkyl, $C_{1-6}$-alkylene-$C_{3-6}$-cycloalkyl, $C_{1-4}$-alkylene-phenyl, $C_{1-4}$-alkylene-furanyl, $C_{3-6}$-cycloalkyl, $C_{1-4}$-alkylene-$O$—$C_{1-4}$-alkyl, $C_{1-6}$-haloalkyl or a five- or six-membered carbocyclic non-aromatic ring, optionally containing independently from each other one or two N, O, S, or $SO_2$, replacing a carbon atom of the ring, optionally substituted with 4-cyclopropylmethyl-piperazinyl $R^{1.2.2}$ is selected from H, $C_{1-6}$-alkyl;

$R^{1.2.3}$ is selected from a five- or six-membered carbocyclic non-aromatic ring, optionally containing independently from each other one or two N, O, S, or $SO_2$, replacing a carbon atom of the ring;

$R^{1.3}$ is selected from phenyl, heteroaryl or indolyl, each optionally substituted with one or two residues selected from the group consisting of $C_{1-6}$-alkyl, $C_{3-6}$-cycloalkyl, $O$—$C_{1-6}$-alkyl, $O$—$C_{1-6}$-haloalkyl, phenyl, heteroaryl; where in some instances $R^{1.3}$ is selected from phenyl, pyrazolyl, isoxazolyl, pyridinyl, pyrimidinyl, indolyl or oxadiazolyl, each optionally substituted with one or two residues selected from the group consisting of $C_{1-6}$-alkyl, $C_{3-6}$-cycloalkyl, $O$—$C_{1-6}$-alkyl, $O$—$C_{1-6}$-haloalkyl, phenyl, pyrrolidinyl;

$R^2$ is selected from the group consisting of $C_{1-6}$-alkylene-phenyl, $C_{1-6}$-alkylene-naphthyl, and $C_{1-6}$-alkylene-thiophenyl; each optionally substituted with one, two or three residues selected from the group consisting of $C_{1-6}$-alkyl, $C_{1-6}$-haloalkyl, $O$—$C_{1-6}$-alkyl, $O$—$C_{1-6}$-haloalkyl, halogen;

$R^3$ is selected from H, $C_{1-4}$-alkyl;

$R^4$ is selected from H, $C_{1-4}$-alkyl; or $R^3$ and $R^4$ together are forming a $CH_2$—$CH_2$ group.

Another embodiment of the present invention further comprises administration to a subject of the compounds of formula 1 (above), wherein A is $CH_2$, O or N—$C_{1-4}$-alkyl;

$R^1$ is selected from $NHR^{1.1}$, $NMeR^{1.1}$;

$R^{1.1}$ is phenyl, optionally substituted with one or two residues selected from the group consisting of $C_{1-6}$-alkyl, $C_{2-6}$-alkenyl, $C_{2-6}$-alkynyl, $C_{1-6}$-haloalkyl, $C_{1-6}$-alkylene-OH, $C_{2-6}$-alkenylene-OH, $C_{2-6}$-alkynylene-OH, $CH_2CON(C_{1-6}$-alkyl$)_2$, $CH_2NHCONH$—$C_{3-6}$-cycloalkyl, CN, CO-pyridinyl, $CONR^{1.1.1}R^{1.1.2}$, $COO$—$C_{1-6}$-alkyl, $N(SO_2$—$C_{1-6}$-alkyl)($CH_2CON(C_{1-4}$-alkyl$)_2$)$O$—$C_{1-6}$-alkyl, O-pyridinyl, $SO_2$—$C_{1-6}$-alkyl, $SO_2$—$C_{1-6}$-alkylen-OH, $SO_2$—$C_{3-6}$-cycloalkyl, $SO_2$-piperidinyl, $SO_2NH$—$C_{1-6}$-alkyl, $SO_2N(C_{1-6}$-alkyl$)_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl, =O;

$R^{1.1.1}$ is selected from H, $C_{1-6}$-alkyl, $C_{3-6}$-cycloalkyl, $C_{1-6}$-haloalkyl, $CH_2CON(C_{1-6}$-alkyl$)_2$, $CH_2CO$-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;

$R^{1.1.2}$ is selected from H, $C_{1-6}$-alkyl, $SO_2C_{1-6}$-alkyl; or $R^{1.1.1}$ and $R^{1.1.2}$ together are forming a four-, five- or six-membered carbocyclic ring, optionally containing one N or O, replacing a carbon atom of the ring, optionally substituted with one or two residues selected from the group consisting of $C_{1-6}$-alkyl, $C_{1-4}$-alkylene-OH, OH, =O; or $R^{1.1}$ is phenyl, wherein two adjacent residues are together forming a five- or six-membered carbocyclic aromatic or non-aromatic ring, optionally containing independently from each other one or two N, S, or $SO_2$, replacing a carbon atom of the ring, wherein the ring is optionally substituted with $C_{1-4}$-alkyl or =O;

$R^2$ is selected from the group consisting of $C_{1-6}$-alkylene-phenyl, $C_{1-6}$-alkylene-naphthyl, and $C_{1-6}$-alkylene-thiophenyl; each optionally substituted with one, two or three residues selected from the group consisting of $C_{1-6}$-alkyl, $C_{1-6}$-haloalkyl, $O$—$C_{1-6}$-alkyl, $O$—$C_{1-6}$-haloalkyl, halogen;

$R^3$ is selected from H, $C_{1-4}$-alkyl;

$R^4$ is selected from H, $C_{1-4}$-alkyl; or $R^3$ and $R^4$ together are forming a $CH_2$—$CH_2$ group.

Another embodiment of the present invention further comprises administration to a subject of the compounds of formula 1, wherein A is $CH_2$, O or N—$C_{1-4}$-alkyl;

$R^1$ is selected from $NHR^{1.2}$, $NMeR^{1.2}$; wherein $R^{1.2}$ is selected from heteroaryl, optionally substituted with one or two residues selected from the group consisting of $C_{1-6}$-alkyl, $C_{2-6}$-alkenyl, $C_{2-6}$-alkynyl, $C_{3-6}$-cycloalkyl, $CH_2COO$—$C_{1-6}$-alkyl, $CONR^{1.2.1}R^{1.2.2}$, $COR^{1.2.3}$, $COO$—$C_{1-6}$-alkyl, $CONH_2$, $O$—$C_{1-6}$-alkyl, halogen, CN, $SO_2N(C_{1-4}$-alkyl$)_2$ or heteroaryl optionally substituted with one or two residues selected from the group consisting of $C_{1-6}$-alkyl; heteroaryl, optionally substituted with a five- or six-membered carbocyclic non-aromatic ring containing independently from each other two N, O, S, or $SO_2$, replacing a carbon atom of the ring; benzothiazolyl, indazolyl, dihydro-indolyl, indanyl, tetrahydro-quinolinyl, each optionally substituted with one or two residues selected from the group consisting of $N(C_{1-6}$-alkyl$)_2$, $CONH$—$C_{1-6}$-alkyl, =O; piperidinyl, optionally substituted with pyridinyl; or 4,5-dihydro-naphtho[2,1-d]thiazole, optionally substituted with $NHCO$—$C_{1-6}$-alkyl, $R^{1.2.1}$ is selected from H, $C_{1-6}$-alkyl, $C_{1-6}$-alkylene-$C_{3-6}$-cycloalkyl, $C_{1-4}$-alkylene-phenyl, $C_{1-4}$-alkylene-furanyl, $C_{3-6}$-cycloalkyl, $C_{1-4}$-alkylene-$O$—$C_{1-4}$-alkyl, $C_{1-6}$-haloalkyl or a five- or six-membered carbocyclic non-aromatic ring, optionally containing independently from each other one or two N, O, S, or $SO_2$, replacing a carbon atom of the ring, optionally substituted with 4-cyclopropylmethyl-piperazinyl $R^{1.2.2}$ is selected from H, $C_{1-6}$-alkyl;

$R^{1.2.3}$ is selected from a five- or six-membered carbocyclic non-aromatic ring, optionally containing independently from each other one or two N, O, S, or $SO_2$, replacing a carbon atom of the ring;

$R^2$ is selected from the group consisting of $C_{1-6}$-alkylene-phenyl, $C_{1-6}$-alkylene-naphthyl, and $C_{1-6}$-alkylene-thiophenyl; each optionally substituted with one, two or three residues selected from the group consisting of $C_{1-6}$-alkyl, $C_{1-6}$-haloalkyl, O—$C_{1-6}$-alkyl, O—$C_{1-6}$-haloalkyl, halogen;
$R^3$ is selected from H, $C_{1-4}$-alkyl;
$R^4$ is selected from H, $C_{1-4}$-alkyl; or
$R^3$ and $R^4$ together are forming a $CH_2$—$CH_2$ group.

Another embodiment of the present invention further comprises administration to a subject of the compounds of formula 1 (above), wherein
A is $CH_2$, O or N—$C_{1-4}$-alkyl;
$R^1$ is selected from $NHR^{1.2}$, $NMeR^{1.2}$; wherein
$R^{1.2}$ is selected from heteroaryl, optionally substituted with one or two residues selected from the group consisting of $C_{1-6}$-alkyl, $C_{2-6}$-alkenyl, $C_{2-6}$-alkynyl, $C_{3-6}$-cycloalkyl, $CH_2COO$—$C_{1-6}$-alkyl, $CONR^{1.2.1}R^{1.2.2}$, $COR^{1.2.3}$, COO—$C_{1-6}$-alkyl, $CONH_2$, O—$C_{1-6}$-alkyl, halogen, CN, $SO_2N(C_{1-4}$-alkyl$)_2$ or heteroaryl optionally substituted with one or two residues selected from the group consisting of $C_{1-6}$-alkyl; heteroaryl, optionally substituted with a five- or six-membered carbocyclic non-aromatic ring containing independently from each other two N, O, S, or $SO_2$, replacing a carbon atom of the ring;
$R^{1.2.1}$ is selected from H, $C_{1-6}$-alkyl, $C_{1-6}$-alkylene-$C_{3-6}$-cycloalkyl, $C_{1-4}$-alkylene-phenyl, $C_{1-4}$-alkylene-furanyl, $C_{3-6}$-cycloalkyl, $C_{1-4}$-alkylene-O—$C_{1-4}$-alkyl, $C_{1-6}$-haloalkyl or a five- or six-membered carbocyclic non-aromatic ring, optionally containing independently from each other one or two N, O, S, or $SO_2$, replacing a carbon atom of the ring, optionally substituted with 4-cyclopropylmethyl-piperazinyl
$R^{1.2.2}$ is selected from H, $C_{1-6}$-alkyl;
$R^{1.2.3}$ is selected from a five- or six-membered carbocyclic non-aromatic ring, optionally containing independently from each other one or two N, O, S, or $SO_2$, replacing a carbon atom of the ring;
$R^2$ is selected from the group consisting of $C_{1-6}$-alkylene-phenyl, $C_{1-6}$-alkylene-naphthyl, and $C_{1-6}$-alkylene-thiophenyl; each optionally substituted with one, two or three residues selected from the group consisting of $C_{1-6}$-alkyl, $C_{1-6}$-haloalkyl, O—$C_{1-6}$-alkyl, O—$C_{1-6}$-haloalkyl, halogen;
$R^3$ is selected from H, $C_{1-4}$-alkyl;
$R^4$ is selected from H, $C_{1-4}$-alkyl; or
$R^3$ and $R^4$ together are forming a $CH_2$—$CH_2$ group.

Another embodiment of the present invention further comprises administration to a subject of the compounds of formula 1, wherein
A is $CH_2$, O or N—$C_{1-4}$-alkyl;
$R^1$ is $NHCH_2$—$R^{1.3}$; wherein
$R^{1.3}$ is selected from phenyl, pyrazolyl, isoxazolyl, pyridinyl, pyrimidinyl, indolyl or oxadiazolyl, each optionally substituted with one or two residues selected from the group consisting of $C_{1-6}$-alkyl, $C_{3-6}$-cycloalkyl, O—$C_{1-6}$-alkyl, O—$C_{1-6}$-haloalkyl, phenyl, pyrrolidinyl;
$R^2$ is selected from the group consisting of $C_{1-6}$-alkylene-phenyl, $C_{1-6}$-alkylene-naphthyl, and $C_{1-6}$-alkylene-thiophenyl; each optionally substituted with one, two or three residues selected from the group consisting of $C_{1-6}$-alkyl, $C_{1-6}$-haloalkyl, O—$C_{1-6}$-alkyl, O—$C_{1-6}$-haloalkyl, halogen;
$R^3$ is selected from H, $C_{1-4}$-alkyl;
$R^4$ is selected from H, $C_{1-4}$-alkyl; or
$R^3$ and $R^4$ together are forming a $CH_2$—$CH_2$ group.

Another embodiment of the present invention further comprises administration to a subject of the compounds of formula 1, wherein
A is selected from $CH_2$, O or N—$C_{1-4}$-alkyl;
$R^1$ is selected from $NHR^{1.1}$, $NMeR^{1.1}$; $NHR^{1.2}$, $NMeR^{1.2}$; $NHCH_2$—$R^{1.3}$;
NH—$C_{3-6}$-cycloalkyl, whereas optionally one carbon atom is replaced by a nitrogen atom, whereas the ring is optionally substituted with one or two residues selected from the group consisting of $C_{1-6}$-alkyl, O—$C_{1-6}$-alkyl, $NHSO_2$-phenyl, NHCONH-phenyl, halogen, CN, $SO_2$—$C_{1-6}$-alkyl, COO—$C_{1-6}$-alkyl; a $C_{9\,or\,10}$-bicyclic-ring, whereas one or two carbon atoms are replaced by nitrogen atoms and the ring system is bound via a nitrogen atom to the basic structure of formula 1 and whereas the ring system is optionally substituted with one or two residues selected from the group consisting of $C_{1-6}$-alkyl, COO—$C_{1-6}$-alkyl, $C_{1-6}$-haloalkyl, O—$C_{1-6}$-alkyl, $NO_2$, halogen, CN, $NHSO_2$—$C_{1-6}$-alkyl, m-methoxyphenyl; a group selected from NHCH(pyridinyl)$CH_2$COO—$C_{1-6}$-alkyl, NHCH($CH_2O$—$C_{1-6}$-alkyl)-benzoimidazolyl, optionally substituted with Cl; or 1-aminocyclopentyl, optionally substituted with methyl-oxadiazolyl; wherein
$R^{1.1}$ is phenyl, optionally substituted with one or two residues selected from the group consisting of $C_{1-6}$-alkyl, $C_{1-6}$-haloalkyl, $CH_2CON(C_{1-6}$-alkyl$)_2$, $CH_2NHCONH$—$C_{3-6}$-cycloalkyl, CN, $CONR^{1.1.1}R^{1.1.2}$, COO—$C_{1-6}$-alkyl, O—$C_{1-6}$-alkyl, $SO_2$—$C_{1-6}$-alkyl, $SO_2$—$C_{1-6}$-alkylen-OH, $SO_2$—$C_{3-6}$-cycloalkyl, $SO_2$-piperidinyl, $SO_2NH$—$C_{1-6}$-alkyl, $SO_2N(C_{1-6}$-alkyl$)_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl, and $=O$;
$R^{1.1.1}$ is selected from H, $C_{1-6}$-alkyl, $C_{3-6}$-cycloalkyl, $C_{1-6}$-haloalkyl, $CH_2CON(C_{1-6}$-alkyl$)_2$, $CH_2CO$-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;
$R^{1.1.2}$ is selected from H, $C_{1-6}$-alkyl, or $SO_2C_{1-6}$-alkyl; or
$R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$;
$R^{1.2}$ is selected from heteroaryl, optionally substituted with one or two residues selected from the group consisting of $C_{1-6}$-alkyl, $C_{3-6}$-cycloalkyl, $CH_2COO$—$C_{1-6}$-alkyl, $CONR^{1.2.1}R^{1.2.2}$, COO—$C_{1-6}$-alkyl, $CONH_2$, O—$C_{1-6}$-alkyl, halogen, CN, CO-pyrrolidinyl, CO-morpholinyl or heteroaryl optionally substituted with one or two residues selected from the group consisting of $C_{1-6}$-alkyl; benzothiazolyl, indazolyl, dihydro-indolyl, indanyl, tetrahydro-quinolinyl, each optionally substituted with one or two residues selected from the group consisting of $N(C_{1-6}$-alkyl$)_2$, CONH—$C_{1-6}$-alkyl, $=O$; piperidinyl, optionally substituted with pyridinyl; and 4,5-dihydro-naphtho[2,1-d]thiazole, optionally substituted with NHCO—$C_{1-6}$-alkyl,
$R^{1.2.1}$ is selected from H, $C_{1-6}$-alkyl;
$R^{1.2.2}$ is selected from H, $C_{1-6}$-alkyl;

$R^{1.3}$ is selected from phenyl, pyrazolyl, isoxazolyl, pyrimidinyl, indolyl or oxadiazolyl, each optionally substituted with one or two residues selected from the group consisting of $C_{1-6}$-alkyl, $C_{3-6}$-cycloalkyl, O—$C_{1-6}$-alkyl, O—$C_{1-6}$-haloalkyl;

$R^2$ is selected from $C_{1-6}$-alkylene-phenyl or $C_{1-6}$-alkylene-naphthyl, both optionally substituted with one or two residues selected from the group consisting of $C_{1-6}$-alkyl, $C_{1-6}$-haloalkyl, O—$C_{1-6}$-alkyl, O—$C_{1-6}$-haloalkyl, halogen; or $CH_2$-thiophenyl, optionally substituted with one or two residues selected from the group consisting of halogen;

$R^3$ is selected from H, $C_{1-4}$-alkyl;

$R^4$ is selected from H, $C_{1-4}$-alkyl; or $R^3$ and $R^4$ together are forming a $CH_2$—$CH_2$ group.

Another embodiment of the present invention further comprises administration to a subject of the compounds of formula 1, wherein A is $CH_2$, O or NMe;

$R^1$ is selected from $NHR^{1.1}$, $NMeR^{1.1}$; $NHR^{1.2}$, $NMeR^{1.2}$; $NHCH_2$—$R^{1.3}$; NH-cyclohexyl, optionally substituted with one or two residues selected from the group consisting of $C_{1-4}$-alkyl, $NHSO_2$-phenyl, NHCONH-phenyl, halogen; NH-pyrrolidinyl, optionally substituted with one or two residues selected from the group consisting of $SO_2$—$C_{1-4}$-alkyl, COO—$C_{1-4}$-alkyl; piperidinyl, optionally substituted with one or two residues selected from the group consisting of $NHSO_2$—$C_{1-4}$-alkyl, m-methoxyphenyl; dihydro-indolyl, dihydro-isoindolyl, tetrahydro-quinolinyl or tetrahydro-isoquinolinyl, optionally substituted with one or two residues selected from the group consisting of $C_{1-4}$-alkyl, COO—$C_{1-4}$-alkyl, $C_{1-4}$-haloalkyl, O—$C_{1-4}$-alkyl, $NO_2$, halogen; a group selected from NHCH(pyridinyl)$CH_2COO$—$C_{1-4}$-alkyl, $NHCH(CH_2O$—$C_{1-4}$-alkyl)-benzoimidazolyl, optionally substituted with Cl; or 1-aminocyclopentyl, optionally substituted with methyl-oxadiazolyl; wherein $R^{1.1}$ is phenyl, optionally substituted with one or two residues selected from the group consisting of $C_{1-4}$-alkyl, $C_{1-4}$-haloalkyl, $CH_2CON(C_{1-4}$-alkyl)$_2$, $CH_2NHCONH$—$C_{3-6}$-cycloalkyl, CN, $CONR^{1.1.1}R^{1.1.2}$, COO—$C_{1-4}$-alkyl, O—$C_{1-4}$-alkyl, $SO_2$—$C_{1-4}$-alkyl, $SO_2$—$C_{1-4}$-alkylen-OH, $SO_2$—$C_{3-6}$-cycloalkyl, $SO_2$-piperidinyl, $SO_2NH$—$C_{1-4}$-alkyl, $SO_2N(C_{1-4}$-alkyl)$_2$, halogen, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of $C_{1-4}$-alkyl, $NHC_{1-4}$-alkyl, =O;

$R^{1.1.1}$ is selected from H, $C_{1-6}$-alkyl, $C_{3-6}$-cycloalkyl, $C_{1-4}$-haloalkyl, $CH_2CON(C_{1-4}$-alkyl)$_2$, $CH_2CO$-azetindinyl, $C_{1-4}$-alkylen-$C_{3-6}$-cycloalkyl, $CH_2$-pyranyl, $CH_2$-tetrahydrofuranyl, $CH_2$-furanyl, $C_{1-4}$-alkylen-OH or thiadiazolyl, optionally substituted with $C_{1-4}$-alkyl;

$R^{1.1.2}$ is selected from H, $C_{1-4}$-alkyl, or $SO_2C_{1-4}$-alkyl; or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$ $R^{1.2}$ is selected from pyridinyl, pyridazinyl, pyrrolyl, pyrazolyl, isoxazolyl, thiazolyl, thiadiazolyl, optionally substituted with one or two residues selected from the group consisting of $C_{1-4}$-alkyl, $C_{3-6}$-cycloalkyl, $CH_2COO$—$C_{1-4}$-alkyl, $CONR^{1.2.1}R^{1.2.2}$, COO—$C_{1-4}$-alkyl, $CONH_2$, O—$C_{1-4}$-alkyl, halogen, CO-pyrrolidinyl, CO-morpholinyl or pyrazolyl, triazolyl, tetrazolyl, isoxazolyl, oxadiazolyl, each optionally substituted with one or two residues selected from the group consisting of $C_{1-4}$-alkyl; benzothiazolyl, indazolyl, dihydro-indolyl, indanyl, tetrahydro-quinolinyl, each optionally substituted with one or two residues selected from the group consisting of $N(C_{1-4}$-alkyl)$_2$, CONH—$C_{1-4}$-alkyl, =O; piperidinyl, optionally substituted with pyridinyl; 4,5-dihydro-naphtho[2,1-d]thiazole, optionally substituted with NHCO—$C_{1-4}$-alkyl;

$R^{1.2.1}$ is selected from H, $C_{1-4}$-alkyl;

$R^{1.2.2}$ is selected from H, $C_{1-4}$-alkyl;

$R^{1.3}$ is selected from phenyl, pyrazolyl, isoxazolyl, pyrimidinyl, indolyl or oxadiazolyl, each optionally substituted with one or two residues selected from the group consisting of $C_{1-4}$-alkyl, $C_{3-6}$-cycloalkyl, O—$C_{1-4}$-alkyl, O—$C_{1-4}$-haloalkyl;

$R^2$ is selected from $C_{1-6}$-alkylene-phenyl or $C_{1-6}$-alkylene-naphthyl, both optionally substituted with one or two residues selected from the group consisting of $C_{1-4}$-alkyl, $C_{1-4}$-haloalkyl, O—$C_{1-4}$-haloalkyl, halogen; or $CH_2$-thiophenyl, optionally substituted with one or two residues selected from the group consisting of halogen;

$R^3$ is H;

$R^4$ is H; or $R^3$ and $R^4$ together are forming a $CH_2$—$CH_2$ group.

Another embodiment of the present invention further comprises administration to a subject of the compounds of formula 1, wherein A is $CH_2$, O or NMe;

$R^1$ is selected from $NHR^{1.1}$, $NMeR^{1.1}$; $NHR^{1.2}$, $NMeR^{1.2}$; $NHCH_2$—$R^{1.3}$; NH-piperidinyl, optionally substituted with pyridinyl; NH-cyclohexyl, optionally substituted with one or two residues selected from the group consisting of t-Bu, $NHSO_2$-phenyl, NHCONH-phenyl, F; NH-pyrrolidinyl, optionally substituted with one or two residues selected from the group consisting of $SO_2Me$, COO-t-Bu; piperidinyl, optionally substituted with one or two residues selected from the group consisting of $NHSO_2$-n-Bu, m-methoxyphenyl; dihydro-indolyl, dihydro-isoindolyl, tetrahydro-quinolinyl or tetrahydro-isoquinolinyl, optionally substituted with one or two residues selected from the group consisting of Me, COOMe, $CF_3$, OMe, $NO_2$, F, Br; a group selected from NHCH(pyridinyl)$CH_2COOMe$, $NHCH(CH_2OMe)$-benzoimidazolyl, optionally substituted with Cl; or 1-aminocyclopentyl, optionally substituted with methyl-oxadiazolyl;

$R^{1.1}$ is phenyl, optionally substituted with one or two residues selected from the group consisting of Me, Et, t-Bu, $CF_3$, $CH_2CONMe_2$, $CH_2NHCONH$-cyclohexyl, CN, $CONR^{1.1.1}R^{1.1.2}$, COOMe, COOEt, OMe, $SO_2Me$, $SO_2CH_2CH_2OH$, $SO_2Et$, $SO_2$-cyclopropyl, $SO_2$-piperidinyl, $SO_2NHEt$, $SO_2NMeEt$, F, Cl, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

$R^{1.1.1}$ is selected from H, Me, Et, t-Bu, i-Pr, cyclopropyl, $CH_2$-i-Pr, $CH_2$-t-Bu, $CH(CH_3)CH_2CH_3$, $CH_2CHF_2$, $CH_2CONMe_2$, $CH_2CO$-azetindinyl, $CH_2$-cyclopropyl, $CH_2$-cyclobutyl, $CH_2$-pyranyl, $CH_2$-tetrahydrofuranyl, $CH_2$-furanyl, $CH_2CH_2OH$ or thiadiazolyl, optionally substituted with Me;

$R^{1.1.2}$ is selected from H, Me, Et, $SO_2Me$, or $SO_2Et$, or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$ $R^{1.2}$ is selected from pyridinyl, pyrrolyl, pyrazolyl, isoxazolyl, thiazolyl, thiadiazolyl, optionally substituted with one or two residues selected from the group consisting of Me, Et, Pr, Bu, cyclopropyl, $CH_2COOEt$, $CONR^{1.2.1}R^{1.2.2}$, COOMe, COOEt, $CONH_2$, OMe, Cl, Br CO-pyrrolidinyl, CO-morpholinyl or pyrazolyl, triazolyl, tetrazolyl, isoxazolyl, oxadiazolyl, each optionally substituted Me; benzothiazolyl, indazolyl, dihydro-indolyl, indanyl, tetrahydro-quinolinyl, each optionally substituted with one or two residues selected from the group consisting of $NMe_2$, CONHMe, =O; 4,5-dihydro-naphtho[2,1-d]thiazole, optionally substituted with NHCOMe, wherein $R^{1.2.1}$ is selected from H, Me;
$R^{1.2.2}$ is selected from H, Me;

$R^{1.3}$ is selected from phenyl, pyrazolyl, isoxazolyl, pyrimidinyl, indolyl or oxadiazolyl, each optionally substituted with one or two residues selected from the group consisting of Me, Et, Pr, cyclopentyl, OMe, $OCHF_2$;

$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et; or $CH_2$-thiophenyl, optionally substituted with one or two residues selected from the group consisting of Cl, Br;

$R^3$ is H;
$R^4$ is H; or
$R^3$ and $R^4$ together are forming a $CH_2$—$CH_2$ group.

Another embodiment of the present invention further comprises administration to a subject of the compounds of formula 1, wherein A is $CH_2$, O or NMe;
$R^1$ is selected from $NHR^{1.1}$ or $NHR^{1.2}$, wherein
$R^{1.1}$ is phenyl, optionally substituted with one or two residues selected from the group consisting of Me, Et, Pr, Bu, $CF_3$, $CH_2CONMe_2$, $CH_2NHCONH$-cyclohexyl, CN, $CONR^{1.1.1}R^{1.1.2}$, COOMe, COOEt, OMe, $SO_2Me$, $SO_2CH_2CH_2OH$, $SO_2Et$, $SO_2$-cyclopropyl, $SO_2$-piperidinyl, $SO_2NHEt$, $SO_2NMeEt$, F, Cl, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

$R^{1.1.1}$ is selected from H, Me, Et, t-Bu, i-Pr, cyclopropyl, $CH_2$-i-Pr, $CH_2$-t-Bu, $CH(CH_3)CH_2CH_3$, $CH_2CHF_2$, $CH_2CONMe_2$, $CH_2CO$-azetindinyl, $CH_2$-cyclopropyl, $CH_2$-cyclobutyl, $CH_2$-pyranyl, $CH_2$-tetrahydrofuranyl, $CH_2$-furanyl, $CH_2CH_2OH$ or thiadiazolyl, optionally substituted with Me;

$R^{1.1.2}$ is selected from H, Me, Et, $SO_2Me$, $SO_2Et$ or
$R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$;

$R^{1.2}$ is selected from pyridinyl, pyrrolyl, pyrazolyl, isoxazolyl, thiazolyl, thiadiazolyl, optionally substituted with one or two residues selected from the group consisting of Me, Et, Pr, Bu, cyclopropyl, $CH_2COOEt$, $CONR^{1.2.1}R^{1.2.2}$, COOMe, COOEt, $CONH_2$, OMe, Cl, Br CO-pyrrolidinyl, CO-morpholinyl or pyrazolyl, triazolyl, tetrazolyl, isoxazolyl, oxadiazolyl, each optionally substituted Me; benzothiazolyl, indazolyl, dihydro-indolyl, indanyl, tetrahydro-quinolinyl, each optionally substituted with one or two residues selected from the group consisting of $NMe_2$, CONHMe, =O; 4,5-dihydro-naphtho[2,1-d]thiazole, optionally substituted with NHCOMe, wherein $R^{1.2.1}$ is selected from H, Me;
$R^{1.2.2}$ is selected from H, Me;

$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et $R^3$ is H;
$R^4$ is H.

Another embodiment of the present invention further comprises administration to a subject of the compounds of formula 1, wherein A is $CH_2$, O or NMe;
$R^1$ is selected from $NHR^{1.1}$, $NMeR^{1.1}$; $NHR^{1.2}$, $NMeR^{1.2}$; or $NHCH_2$—$R^{1.3}$;

$R^{1.1}$ is phenyl, optionally substituted with one or two residues selected from the group consisting of Me, Et, Pr, Bu, $CF_3$, $CH_2CONMe_2$, $CH_2NHCONH$-cyclohexyl, CN, $CONR^{1.1.1}R^{1.1.2}$, COOMe, COOEt, OMe, $SO_2Me$, $SO_2CH_2CH_2OH$, $SO_2Et$, $SO_2$-cyclopropyl, $SO_2$-piperidinyl, $SO_2NHEt$, $SO_2NMeEt$, F, Cl, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

$R^{1.1.1}$ is selected from H, Me, Et, Pr, Bu, cyclopropyl, $CH_2$—Pr, $CH_2$—Bu, $CH(CH_3)CH_2CH_3$, $CH_2CHF_2$, $CH_2CONMe_2$, $CH_2CO$-azetindinyl, $CH_2$-cyclopropyl, $CH_2$-cyclobutyl, $CH_2$-pyranyl, $CH_2$-tetrahydrofuranyl, $CH_2$-furanyl, $CH_2CH_2OH$ or thiadiazolyl, optionally substituted with Me;

$R^{1.1.2}$ is selected from H, Me, Et, $SO_2Me$, $SO_2Et$, or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$ $R^{1.2}$ is selected from pyridinyl, pyrrolyl, pyrazolyl, isoxazolyl, thiazolyl, thiadiazolyl, optionally substituted with one or two residues selected from the group consisting of Me, Et, Pr, Bu, cyclopropyl, $CH_2COOEt$, $CONR^{1.2.1}R^{1.2.2}$, COOMe, COOEt, CONH$_2$, OMe, Cl, Br CO-pyrrolidinyl, CO-morpholinyl or pyrazolyl, triazolyl, tetrazolyl, isoxazolyl, oxadiazolyl, each optionally substituted Me; benzothiazolyl, indazolyl, dihydro-indolyl, indanyl, tetrahydro-quinolinyl, each optionally substituted with one or two residues selected from the group consisting of NMe$_2$, CONHMe, =O; 4,5-dihydronaphtho[2,1-d]thiazole, optionally substituted with NHCOMe, wherein $R^{1.2.1}$ is selected from H, Me;

$R^{1.2.2}$ is selected from H, Me;

$R^{1.3}$ is selected from phenyl, pyrazolyl, isoxazolyl, pyrimidinyl, indolyl or oxadiazolyl, each optionally substituted with one or two residues selected from the group consisting of Me, Et, Pr, cyclopentyl, OMe, OCHF$_2$;

$R^2$ is selected from CH$_2$-phenyl or CH$_2$-naphthyl, both optionally substituted with one or two residues selected from the group consisting of CH$_3$, CF$_3$, OCF$_3$, F, Cl, Br, Et; or CH$_2$-thiophenyl, optionally substituted with one or two residues selected from the group consisting of Cl, Br;

$R^3$ is H;

$R^4$ is H;

or $R^3$ and $R^4$ together are forming a CH$_2$—CH$_2$ group.

Another embodiment of the present invention further comprises administration to a subject of the compounds of formula 1, wherein A is CH$_2$, O or NMe;

$R^1$ is selected from NHR$^{1.1}$, NMeR$^{1.1}$;

$R^{1.1}$ is phenyl, optionally substituted with one or two residues selected from the group consisting of Me, Et, t-Bu, CF$_3$, CH$_2$CONMe$_2$, CH$_2$NHCONH-cyclohexyl, CN, CONR$^{1.1.1}$R$^{1.1.2}$, COOMe, COOEt, OMe, SO$_2$Me, SO$_2$CH$_2$CH$_2$OH, SO$_2$Et, SO$_2$-cyclopropyl, SO$_2$-piperidinyl, SO$_2$NHEt, SO$_2$NMeEt, F, Cl, CO-morpholinyl, CH$_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O; wherein $R^{1.1.1}$ is selected from H, Me, Et, Bu, Pr, cyclopropyl, CH$_2$—Pr, CH$_2$—Bu, CH(CH$_3$)CH$_2$CH$_3$, CH$_2$CHF$_2$, CH$_2$CONMe$_2$, CH$_2$CO-azetindinyl, CH$_2$-cyclopropyl, CH$_2$-cyclobutyl, CH$_2$-pyranyl, CH$_2$-tetrahydrofuranyl, CH$_2$-furanyl, CH$_2$CH$_2$OH or thiadiazolyl, optionally substituted with Me;

$R^{1.1.2}$ is selected from H, Me, Et, SO$_2$Me, SO$_2$Et or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of CH$_2$OH;

$R^2$ is selected from CH$_2$-phenyl or CH$_2$-naphthyl, both optionally substituted with one or two residues selected from the group consisting of CH$_3$, CF$_3$, OCF$_3$, F, Cl, Br, Et; or CH$_2$-thiophenyl, optionally substituted with one or two residues selected from the group consisting of Cl, Br;

$R^3$ is H;

$R^4$ is H;

or $R^3$ and $R^4$ together are forming a CH$_2$—CH$_2$ group.

Another embodiment of the present invention further comprises administration to a subject of the compounds of formula 1, wherein A is CH$_2$, O or NMe $R^1$ is selected from NHR$^{1.1}$, NMeR$^{1.1}$; wherein $R^{1.1}$ is phenyl, optionally substituted with one or two residues selected from the group consisting of Me, Et, t-Bu, CF$_3$, CH$_2$CONMe$_2$, CH$_2$NHCONH-cyclohexyl, CN, CONR$^{1.1.1}$R$^{1.1.2}$, COOMe, COOEt, OMe, SO$_2$Me, SO$_2$CH$_2$CH$_2$OH, SO$_2$Et, SO$_2$-cyclopropyl, SO$_2$-piperidinyl, SO$_2$NHEt, SO$_2$NMeEt, F, Cl, CO-morpholinyl, CH$_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O; wherein $R^{1.1.1}$ is selected from H, Me, Et, Bu, Pr, cyclopropyl, CH$_2$—Pr, CH$_2$—Bu, CH(CH$_3$)CH$_2$CH$_3$, CH$_2$CHF$_2$, CH$_2$CONMe$_2$, CH$_2$CO-azetindinyl, CH$_2$-cyclopropyl, CH$_2$-cyclobutyl, CH$_2$-pyranyl, CH$_2$-tetrahydrofuranyl, CH$_2$-furanyl, CH$_2$CH$_2$OH or thiadiazolyl, optionally substituted with Me;

$R^{1.1.2}$ is selected from H, Me, Et, SO$_2$Me, SO$_2$Et or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of CH$_2$OH;

$R^2$ is defined as in Table 1 shown below;

$R^3$ is H;

$R^4$ is H.

Another embodiment of the present invention further comprises administration to a subject of the compounds of formula 1, wherein A is CH$_2$, O or NMe;

$R^1$ is selected from NHR$^{1.1}$, NMeR$^{1.1}$; wherein $R^{1.1}$ is phenyl, optionally substituted with one or two residues selected from the group consisting of Me, Et, t-Bu, CF$_3$, CH$_2$CONMe$_2$, CH$_2$NHCONH-cyclohexyl, CN, CONR$^{1.1.1}$R$^{1.1.2}$, COOMe, COOEt, OMe, SO$_2$Me, SO$_2$CH$_2$CH$_2$OH, SO$_2$Et, SO$_2$-cyclopropyl, SO$_2$-piperidinyl, SO$_2$NHEt, SO$_2$NMeEt, F, Cl, CO-morpholinyl, CH$_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

and $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of CH$_2$OH;

$R^2$ is defined as in Table 1 shown below;

$R^3$ is H;

$R^4$ is H.

Another embodiment of the present invention further comprises administration to a subject of the compounds of formula 1, wherein A is CH$_2$, O or NMe;

$R^1$ is selected from NHR$^{1.1}$, NMeR$^{1.1}$; wherein $R^{1.1}$ is phenyl, optionally substituted with one or two residues selected from the group consisting of Me, Et, t-Bu, CF$_3$, CH$_2$CONMe$_2$, CH$_2$NHCONH-cyclohexyl, CN, CONR$^{1.1.1}$R$^{1.1.2}$, COOMe, COOEt, OMe, F, Cl; wherein $R^{1.1.1}$ is selected from H, Me, Et, Bu, Pr, cyclopropyl, CH$_2$—Pr, CH$_2$—Bu, CH(CH$_3$)CH$_2$CH$_3$, CH$_2$CHF$_2$, CH$_2$CONMe$_2$, CH$_2$CO-azetindinyl, CH$_2$-cyclopropyl, CH$_2$-cyclobutyl, CH$_2$-pyranyl, CH$_2$-tetrahydrofuranyl, CH$_2$-furanyl, CH$_2$CH$_2$OH or thiadiazolyl, optionally substituted with Me;

R$^{1.1.2}$ is selected from H, Me, Et, SO$_2$Me, SO$_2$Et;

R$^2$ is defined as in Table 1 shown below;

R$^3$ is H;

R$^4$ is H.

Another embodiment of the present invention further comprises administration to a subject of the compounds of formula 1, wherein A is CH$_2$, O or NMe;

R$^1$ is selected from NHR$^{1.1}$, NMeR$^{1.1}$; wherein

R$^{1.1}$ is phenyl, optionally substituted with one or two residues selected from the group consisting of SO$_2$Me, SO$_2$CH$_2$CH$_2$OH, SO$_2$Et, SO$_2$-cyclopropyl, SO$_2$-piperidinyl, SO$_2$NHEt, SO$_2$NMeEt; wherein R$^{1.1.1}$ is selected from H, Me, Et, Bu, Pr, cyclopropyl, CH$_2$—Pr, CH$_2$—Bu, CH(CH$_3$)CH$_2$CH$_3$, CH$_2$CHF$_2$, CH$_2$CONMe$_2$, CH$_2$CO-azetindinyl, CH$_2$-cyclopropyl, CH$_2$-cyclobutyl, CH$_2$-pyranyl, CH$_2$-tetrahydrofuranyl, CH$_2$-furanyl, CH$_2$CH$_2$OH or thiadiazolyl, optionally substituted with Me;

R$^{1.1.2}$ is selected from H, Me, Et, SO$_2$Me, SO$_2$Et;

R$^2$ is defined as in Table 1 shown below;

R$^3$ is H;

R$^4$ is H.

Another embodiment of the present invention further comprises administration to a subject of the compounds of formula 1, wherein A is CH$_2$, O or NMe;

R$^1$ is selected from NHR$^{1.1}$, NMeR$^{1.1}$; wherein

R$^{1.1}$ is phenyl, optionally substituted with one residue selected from the group consisting of Me, Et, t-Bu, CF$_3$, CH$_2$CONMe$_2$, CH$_2$NHCONH-cyclohexyl, CN, CONR$^{1.1.1}$R$^{1.1.2}$, COOMe, COOEt, OMe, SO$_2$Me, SO$_2$CH$_2$CH$_2$OH, SO$_2$Et, SO$_2$-cyclopropyl, SO$_2$-piperidinyl, SO$_2$NHEt, SO$_2$NMeEt, F, Cl, and additionally with one residue selected from the group consisting of CO-morpholinyl, CH$_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O; wherein R$^{1.1.1}$ is selected from H, Me, Et, Bu, Pr, cyclopropyl, CH$_2$—Pr, CH$_2$—Bu, CH(CH$_3$)CH$_2$CH$_3$, CH$_2$CHF$_2$, CH$_2$CONMe$_2$, CH$_2$CO-azetindinyl, CH$_2$-cyclopropyl, CH$_2$-cyclobutyl, CH$_2$-pyranyl, CH$_2$-tetrahydrofuranyl, CH$_2$-furanyl, CH$_2$CH$_2$OH or thiadiazolyl, optionally substituted with Me;

R$^{1.1.2}$ is selected from H, Me, Et, SO$_2$Me, SO$_2$Et;

R$^2$ is defined as in Table 1 shown below;

R$^3$ is H;

R$^4$ is H.

Another embodiment of the present invention further comprises administration to a subject of the compounds of formula 1, wherein A is CH$_2$, O or NMe;

R$^1$ is selected from NHR$^{1.2}$, NMeR$^{1.2}$; wherein

R$^{1.2}$ is selected from pyridinyl, pyridazinyl, pyrrolyl, pyrazolyl, isoxazolyl, thiazolyl, thiadiazolyl, optionally substituted with one or two residues selected from the group consisting of Me, Et, Pr, Bu, cyclopropyl, CH$_2$COOEt, CONR$^{1.2.1}$R$^{1.2.2}$, COOMe, COOEt, CONH$_2$, OMe, Cl, Br CO-pyrrolidinyl, CO-morpholinyl or pyrazolyl, triazolyl, tetrazolyl, isoxazolyl, oxadiazolyl, each optionally substituted Me; benzothiazolyl, indazolyl, dihydro-indolyl, indanyl, tetrahydro-quinolinyl, each optionally substituted with one or two residues selected from the group consisting of NMe$_2$, CONHMe, =O; 4,5-dihydro-naphtho[2,1-d]thiazole, optionally substituted with NHCOMe, wherein R$^{1.2.1}$ is selected from H, Me;

R$^{1.2.2}$ is selected from H, Me;

R$^2$ is selected from CH$_2$-phenyl or CH$_2$-naphthyl, both optionally substituted with one or two residues selected from the group consisting of CH$_3$, CF$_3$, OCF$_3$, F, Cl, Br, Et; or CH$_2$-thiophenyl, optionally substituted with one or two residues selected from the group consisting of Cl, Br;

R$^3$ is H;

R$^4$ is H;

or R$^3$ and R$^4$ together are forming a CH$_2$—CH$_2$ group.

Another embodiment of the present invention further comprises administration to a subject of the compounds of formula 1, wherein A is CH$_2$, O or NMe;

R$^1$ is selected from NHR$^{1.2}$, NMeR$^{1.2}$; wherein

R$^{1.2}$ is selected from pyridinyl, pyridazinyl, pyrrolyl, pyrazolyl, isoxazolyl, thiazolyl, thiadiazolyl, optionally substituted with one or two residues selected from the group consisting of Me, Et, n-Pr, i-Pr, Bu, cyclopropyl, CH$_2$COOEt, CONR$^{1.2.1}$R$^{1.2.2}$, COOMe, COOEt, CONH$_2$, OMe, Cl, Br CO-pyrrolidinyl, CO-morpholinyl or pyrazolyl, triazolyl, tetrazolyl, isoxazolyl, oxadiazolyl, each optionally substituted Me; wherein R$^{1.2.1}$ is selected from H, Me;

R$^{1.2.2}$ is selected from H, Me;

R$^2$ is selected from CH$_2$-phenyl or CH$_2$-naphthyl, both optionally substituted with one or two residues selected from the group consisting of CH$_3$, CF$_3$, OCF$_3$, F, Cl, Br, Et; or CH$_2$-thiophenyl, optionally substituted with one or two residues selected from the group consisting of Cl, Br;

R$^3$ is H;

R$^4$ is H;

or R$^3$ and R$^4$ together are forming a CH$_2$—CH$_2$ group.

Another embodiment of the present invention further comprises administration to a subject of the compounds of formula 1, wherein A is CH$_2$, O or NMe;

R$^1$ is selected from NHCH$_2$—R$^{1.3}$; wherein

R$^{1.3}$ is selected from phenyl, pyrazolyl, isoxazolyl, pyrimidinyl, indolyl or oxadiazolyl, each optionally substituted with one or two residues selected from the group consisting of Me, Et, Pr, cyclopentyl, OMe, OCHF$_2$;

R$^2$ is selected from CH$_2$-phenyl or CH$_2$-naphthyl, both optionally substituted with one or two residues selected from the group consisting of CH$_3$, CF$_3$, OCF$_3$, F, Cl, Br, Et; or CH$_2$-thiophenyl, optionally substituted with one or two residues selected from the group consisting of Cl, Br;

R$^3$ is H;

R$^4$ is H;

or R$^3$ and R$^4$ together are forming a CH$_2$—CH$_2$ group.

Another embodiment of the present invention further comprises administration to a subject of the compounds of formula 1, wherein
A is $CH_2$, O or NMe;
$R^1$ is selected from NH-piperidinyl, optionally substituted with pyridinyl; NH-cyclohexyl, optionally substituted with one or two residues selected from the group consisting of t-Bu, $NHSO_2$-phenyl, NHCONH-phenyl, F; NH-pyrrolidinyl, optionally substituted with one or two residues selected from the group consisting of $SO_2Me$, COO-t-Bu; piperidinyl, optionally substituted with one or two residues selected from the group consisting of $NHSO_2$-n-Bu, m-methoxyphenyl; dihydro-indolyl, dihydro-isoindolyl, tetrahydro-quinolinyl or tetrahydro-isoquinolinyl, optionally substituted with one or two residues selected from the group consisting of Me, COOMe, $CF_3$, OMe, $NO_2$, F, Br; a group selected from $NHCH(pyridinyl)CH_2COOMe$, $NHCH(CH_2OMe)$-benzoimidazolyl, optionally substituted with Cl; or 1-aminocyclopentyl, optionally substituted with Methyl-Oxadiazolyl;
$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et; or $CH_2$-thiophenyl, optionally substituted with one or two residues selected from the group consisting of Cl, Br;
$R^3$ is H;
$R^4$ is H;
or $R^3$ and $R^4$ together are forming a $CH_2$—$CH_2$ group.

Another embodiment of the present invention further comprises administration to a subject of the compounds of formula 1, wherein A is $CH_2$, O or NMe, $R^1$ is selected from $NHR^{1.2}$, $NMeR^{1.2}$; $R^2$ is defined as in Table 1 shown below; $R^3$ is H; $R^4$ is and $R^{1.2}$ is selected from pyridinyl, optionally substituted with one or two residues selected from the group consisting of Me, Et, i-Pr, n-Bu, cyclopropyl, $CONR^{1.2.1}R^{1.2.2}$, COOMe, COOEt, $CONH_2$, OMe, Cl, Br CO-pyrrolidinyl, CO-morpholinyl or pyrazolyl, triazolyl, tetrazolyl, isoxazolyl, oxadiazolyl, each optionally substituted Me; pyrrolyl, optionally substituted with one or two residues selected from the group consisting of Me, Et, COOMe, COOEt; pyrazolyl, optionally substituted with one or two residues selected from the group consisting of Me, Et, cyclopropyl, COOEt, CO-pyrrolidinyl; isoxazolyl, optionally substituted with one or two residues selected from the group consisting of t-Bu, COOEt; thiazolyl, optionally substituted with one or two residues selected from the group consisting of Me, n-Pr, i-Pr, Bu, COOMe, COOEt, $CH_2COOEt$, $CONR^{1.2.1}R^{1.2.2}$; thiadiazolyl, optionally substituted with one or two residues selected from the group consisting of COOEt; benzothiazolyl, indazolyl, dihydro-indolyl, indanyl, tetrahydro-quinolinyl, each optionally substituted with one or two residues selected from the group consisting of $NMe_2$, CONHMe, =O; or 4,5-dihydro-naphtho[2,1-d]thiazole, optionally substituted with NHCOMe, and
$R^{1.2.1}$ is selected from H or Me;
$R^{1.2.2}$ is selected from H or Me.

Another embodiment of the present invention further comprises administration to a subject of the compounds of formula 1, wherein A is $CH_2$, O or NMe, $R^1$ is selected from $NHR^{1.2}$, $NMeR^{1.2}$; $R^2$ is defined as in Table 1 shown below; $R^3$ is H; $R^4$ is and $R^{1.2}$ is selected from pyridinyl, optionally substituted with one or two residues selected from the group consisting of Me, Et, i-Pr, n-Bu, $CONR^{1.2.1}R^{1.2.2}$, COOMe, COOEt, $CONH_2$, OMe, Cl, Br; pyrrolyl, optionally substituted with one or two residues selected from the group consisting of Me, Et, COOMe, COOEt; pyrazolyl, optionally substituted with one or two residues selected from the group consisting of Me, Et, cyclopropyl, COOEt, CO-pyrrolidinyl; isoxazolyl, optionally substituted with one or two residues selected from the group consisting of t-Bu, COOEt; thiazolyl, optionally substituted with one or two residues selected from the group consisting of Me, n-Pr, i-Pr, Bu, COOMe, COOEt, $CONR^{1.2.1}R^{1.2.2}$; thiadiazolyl, optionally substituted with one or two residues selected from the group consisting of COOEt; benzothiazolyl, indazolyl, dihydro-indolyl, indanyl, tetrahydro-quinolinyl, each optionally substituted with one or two residues selected from the group consisting of $NMe_2$, CONHMe, =O; and
$R^{1.2.1}$ is H or Me;
$R^{1.2.2}$ is H or Me.

Another embodiment of the present invention further comprises administration to a subject of the compounds of formula 1, wherein A is $CH_2$, O or NMe, $R^1$ is selected from $NHR^{1.2}$, $NMeR^{1.2}$; $R^2$ is defined as in Table 1 shown below; $R^3$ is H; $R^4$ is H; $R^{1.2}$ is pyridinyl, optionally substituted with one or two residues selected from the group consisting of Me, Et, i-Pr, n-Bu, $CONR^{1.2.1}R^{1.2.2}$, COOMe, COOEt, $CONH_2$, OMe, Cl, Br; $R^{1.2.1}$ is H or Me and $R^{1.2.2}$ is H or Me;
A is $CH_2$, O or NMe, $R^1$ is selected from $NHR^{1.2}$, $NMeR^{1.2}$; $R^2$ is defined as in Table 1 shown below; $R^3$ is H; $R^4$ is H; $R^{1.2}$ is pyrrolyl, optionally substituted with one or two residues selected from the group consisting of Me, Et, COOMe, COOEt; $R^{1.2.1}$ is H or Me and $R^{1.2.2}$ is H or Me;
A is $CH_2$, O or NMe, $R^1$ is selected from $NHR^{1.2}$, $NMeR^{1.2}$; $R^2$ is defined as in Table 1 shown below; $R^3$ is H; $R^4$ is H; $R^{1.2}$ is pyrazolyl, optionally substituted with one or two residues selected from the group consisting of Me, Et, cyclopropyl, COOEt, CO-pyrrolidinyl; $R^{1.2.1}$ is H or Me and $R^{1.2.2}$ is H or Me;
A is $CH_2$, O or NMe, $R^1$ is selected from $NHR^{1.2}$, $NMeR^{1.2}$; $R^2$ is defined as in Table 1 shown below; $R^3$ is H; $R^4$ is H; $R^{1.2}$ is isoxazolyl, optionally substituted with one or two residues selected from the group consisting of t-Bu, COOEt; $R^{1.2.1}$ is H or Me and $R^{1.2.2}$ is H or Me;
A is $CH_2$, O or NMe, $R^1$ is selected from $NHR^{1.2}$, $NMeR^{1.2}$; $R^2$ is defined as in Table 1 shown below; $R^3$ is H; $R^4$ is H; $R^{1.2}$ is thiazolyl, optionally substituted with one or two residues selected from the group consisting of Me, n-Pr, i-Pr, Bu, COOMe, COOEt, $CONR^{1.2.1}R^{1.2.2}$; $R^{1.2.1}$ is H or Me and $R^{1.2.2}$ is H or Me;
A is $CH_2$, O or NMe, $R^1$ is selected from $NHR^{1.2}$, $NMeR^{1.2}$; $R^2$ is defined as in Table 1 shown below; $R^3$ is H; $R^4$ is H; $R^{1.2}$ is thiadiazolyl, optionally substituted with one or two residues selected from the group consisting of COOEt; $R^{1.2.1}$ is H or Me and $R^{1.2.2}$ is H or Me; or
A is $CH_2$, O or NMe, $R^1$ is selected from $NHR^{1.2}$, $NMeR^{1.2}$; $R^2$ is defined as in Table 1 shown below; $R^3$ is H; $R^4$ is H; $R^{1.2}$ is benzothiazolyl, indazolyl, dihydro-indolyl, indanyl, tetrahydro-quinolinyl, each optionally substituted with one or two residues selected from the group consisting of $NMe_2$, CONHMe, =O; $R^{1.2.1}$ is H or Me and $R^{1.2.2}$ is H or Me.

Another embodiment of the present invention further comprises administration to a subject of the compounds of formula 1, wherein all groups are defined as above except $R^{1.3}$ is selected from phenyl, optionally substituted with OCHF$_2$; pyrazolyl, optionally substituted with Me or Et; isoxazolyl, optionally substituted with Pr; pyrimidinyl, optionally substituted with two OMe; indolyl; or oxadiazolyl, optionally substituted with cyclopentyl.

Another embodiment of the present invention further comprises administration to a subject of the compounds of formula 1, wherein all groups are defined as above except A is CH$_2$.

Another embodiment of the present invention further comprises administration to a subject of the compounds of formula 1, wherein all groups are defined as above except A is O.

Another embodiment of the present invention further comprises administration to a subject of the compounds of formula 1, wherein all groups are defined as above except A is NMe.

Another embodiment of the present invention are compounds of formula 1, wherein
A is CH$_2$, O or NMe;
R$^1$ is selected from

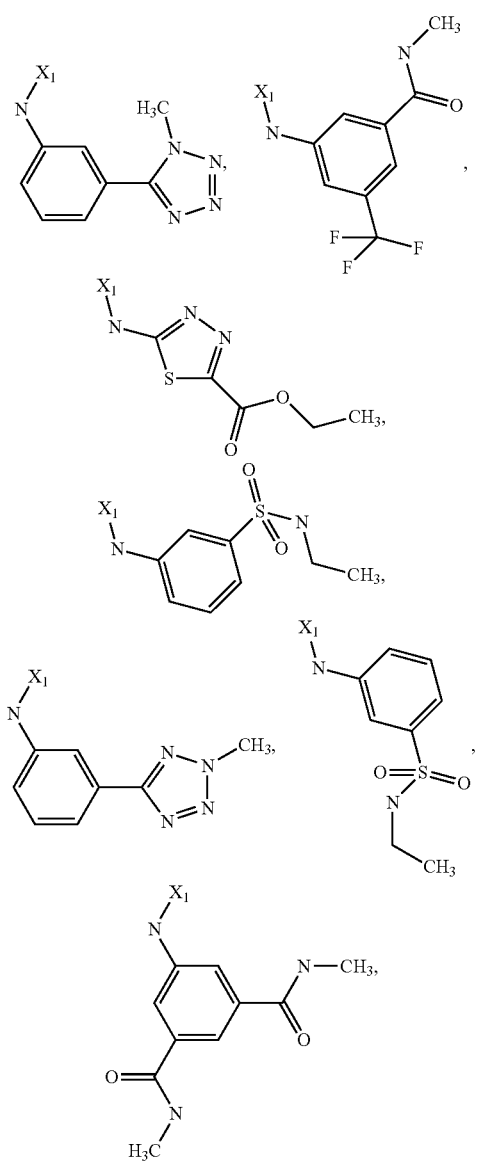

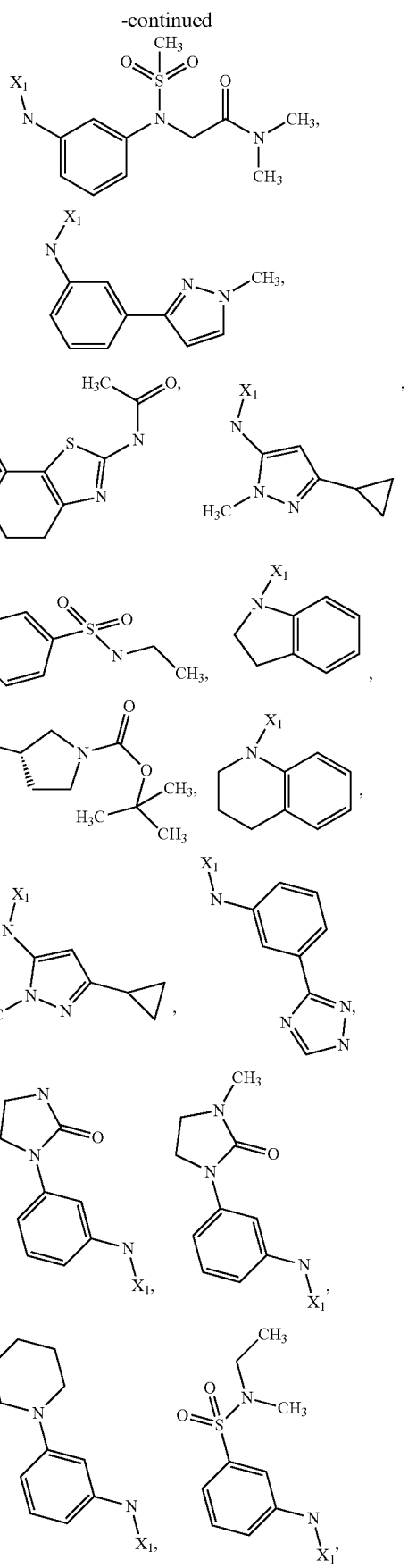

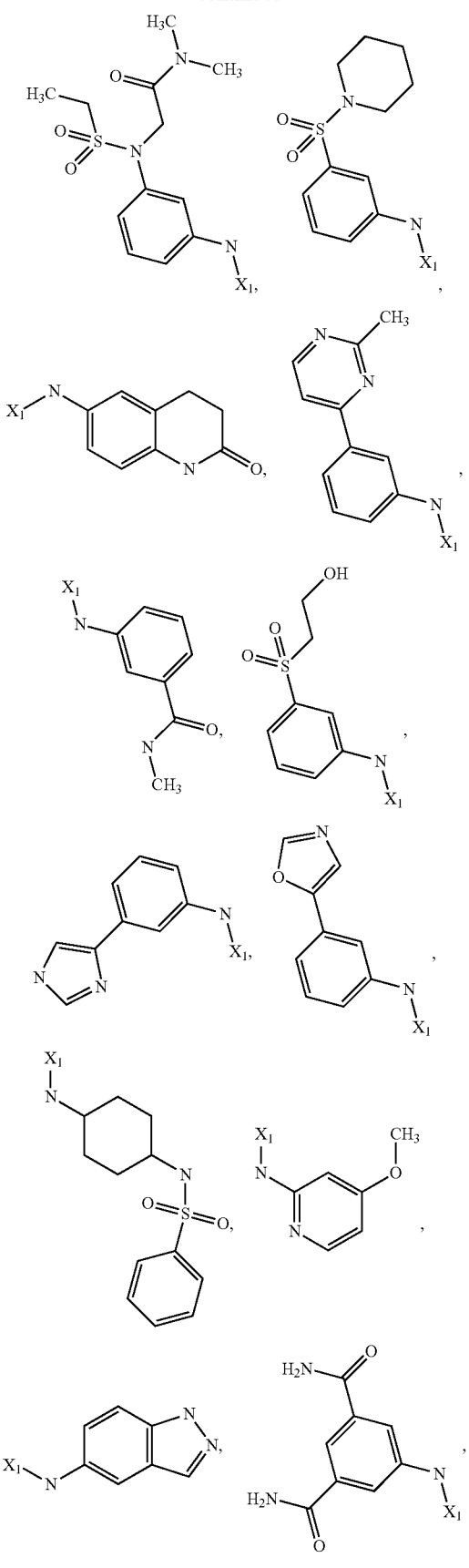
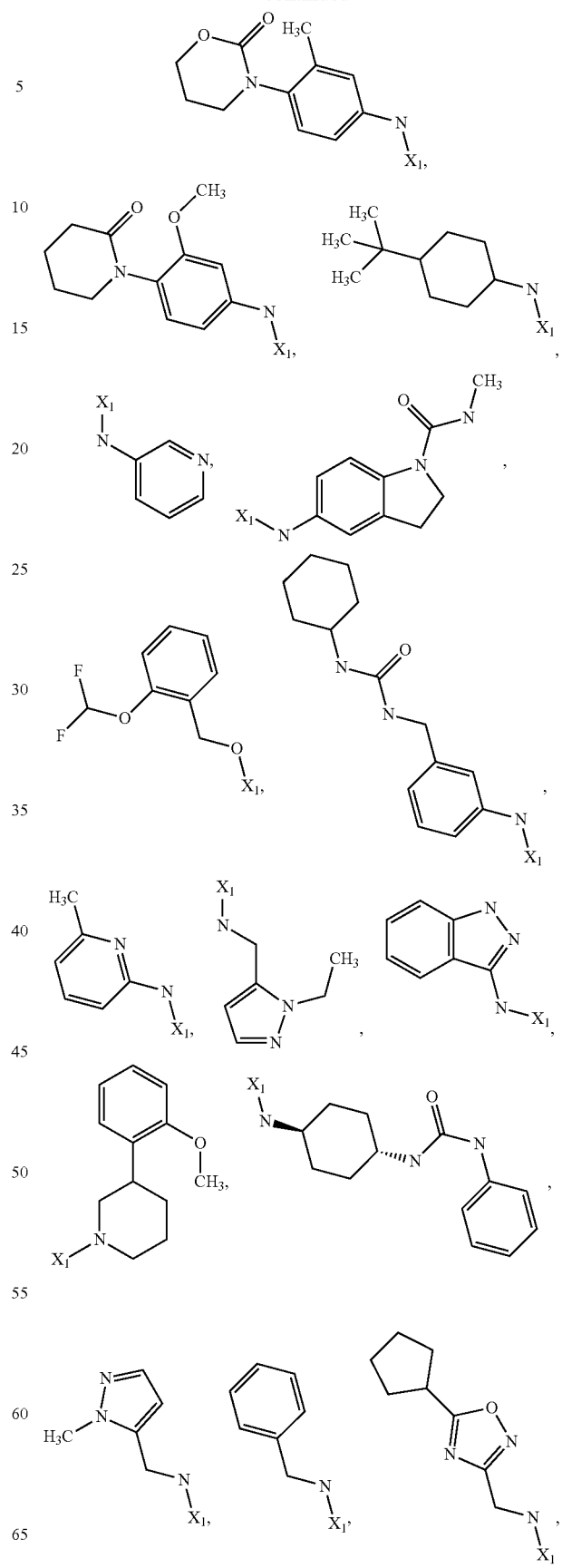

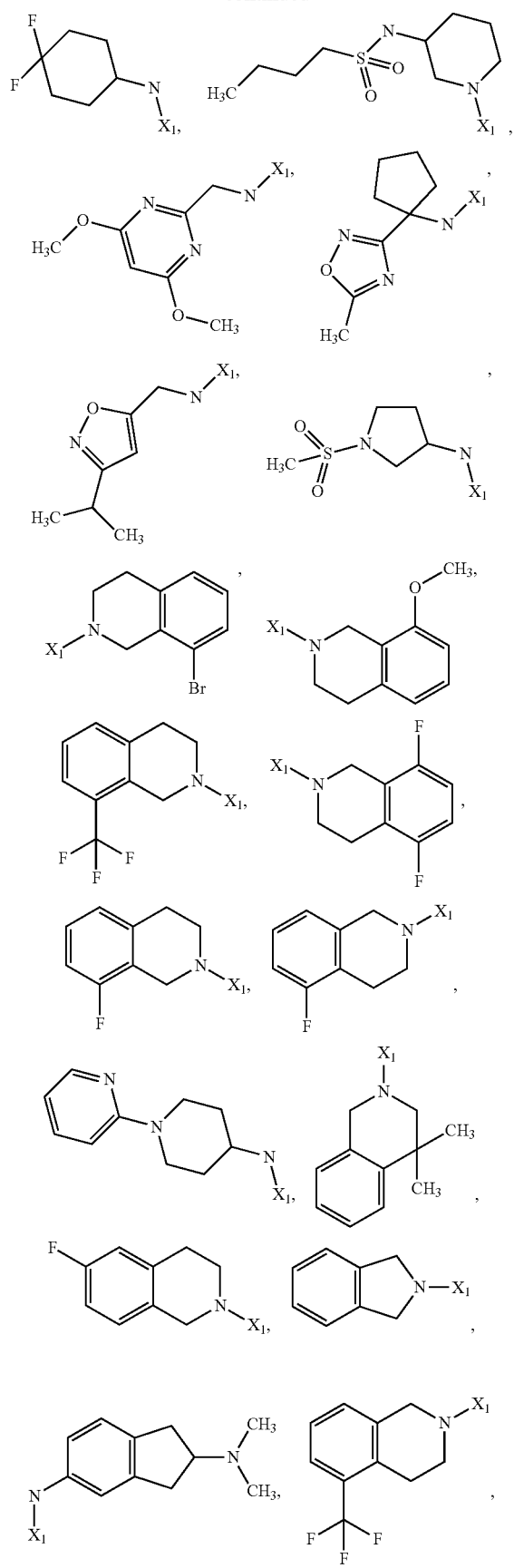
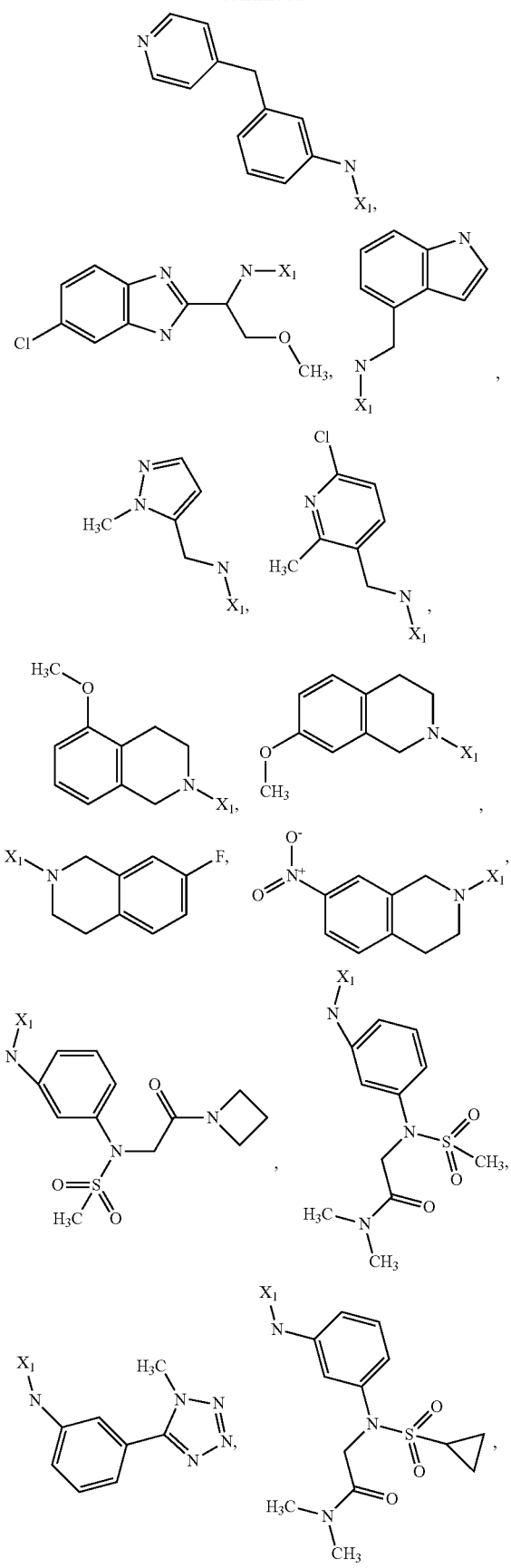

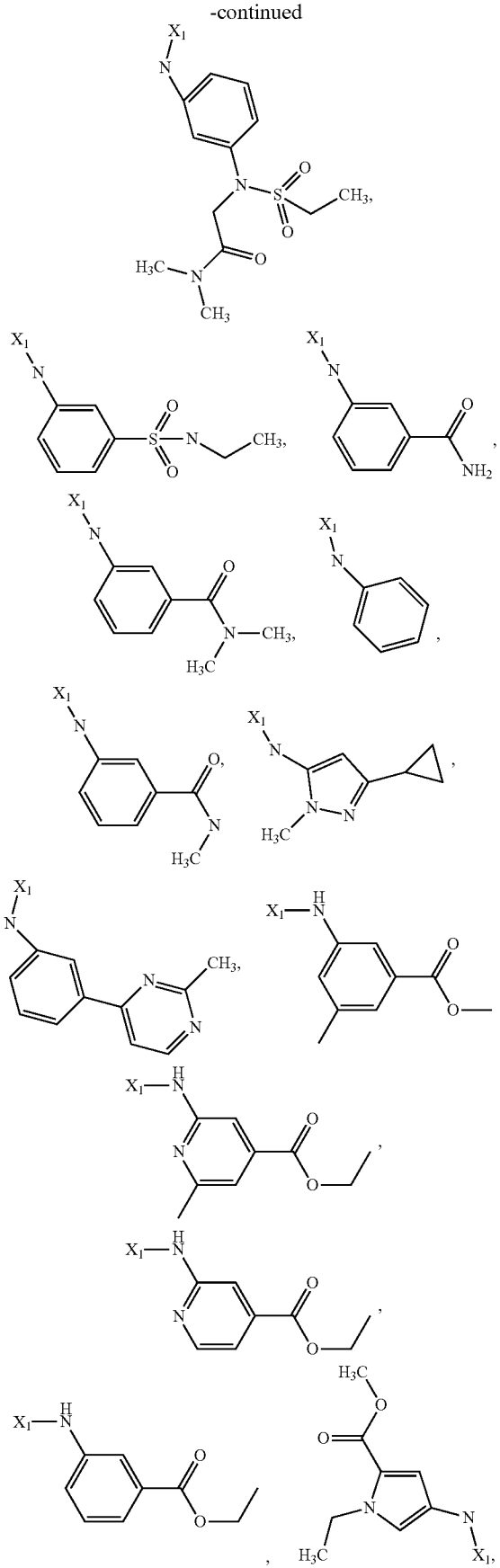
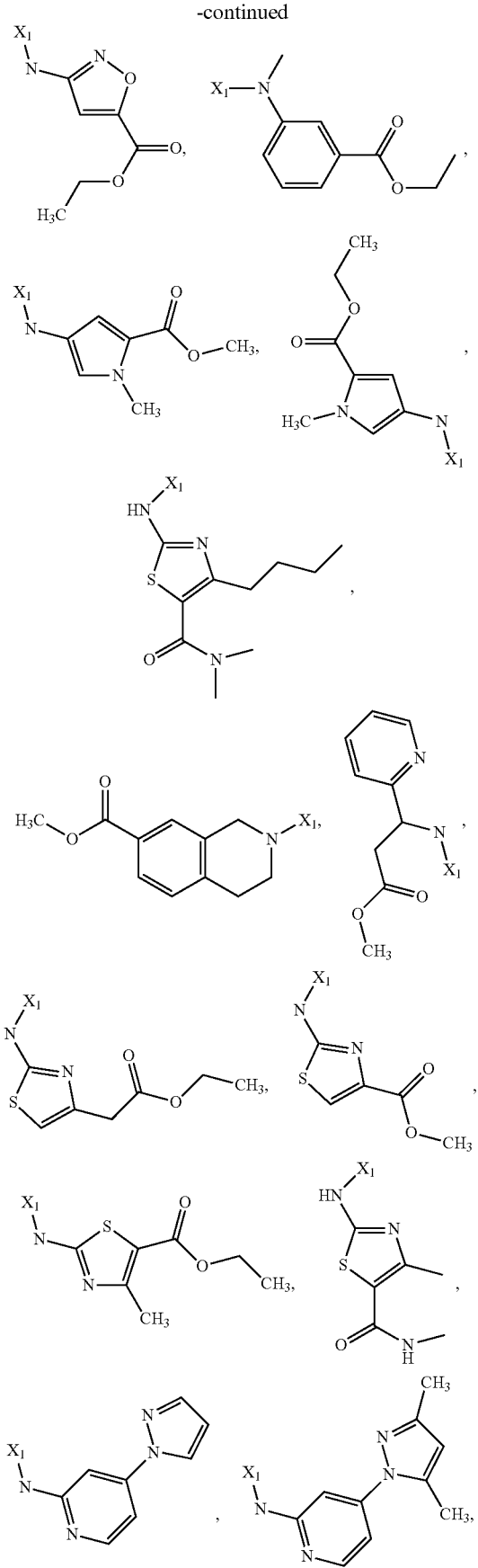

-continued
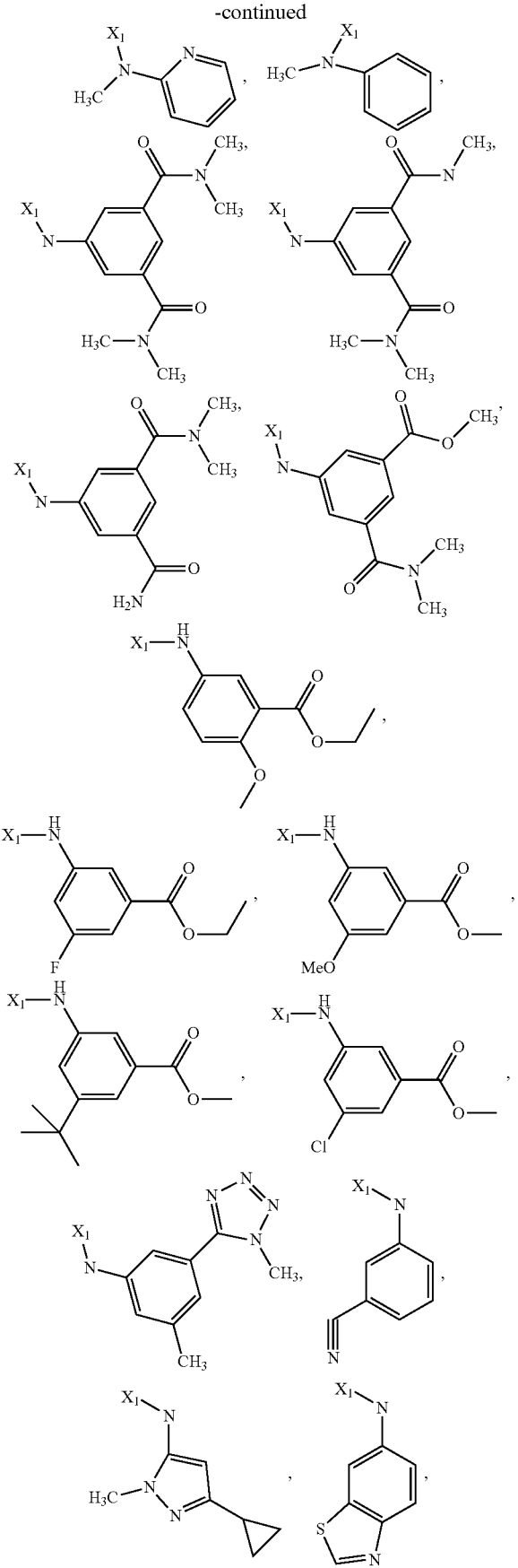
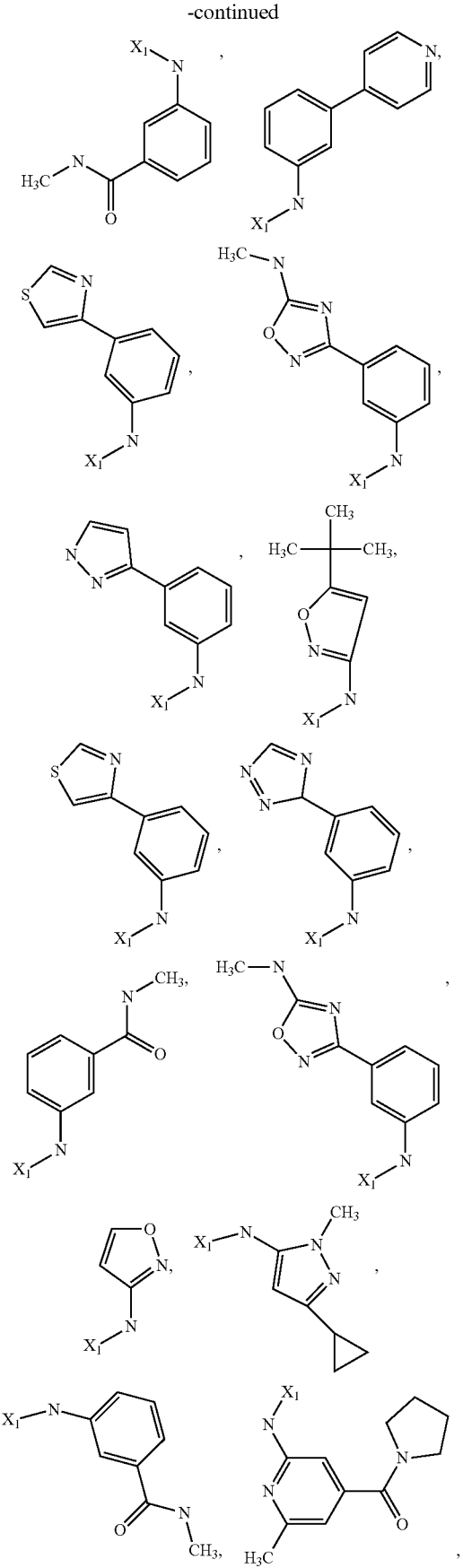

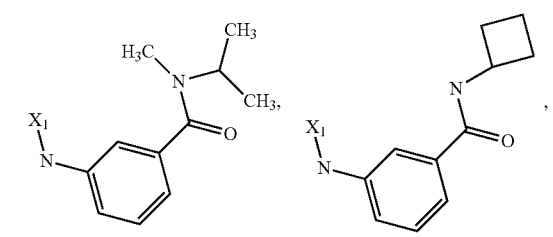
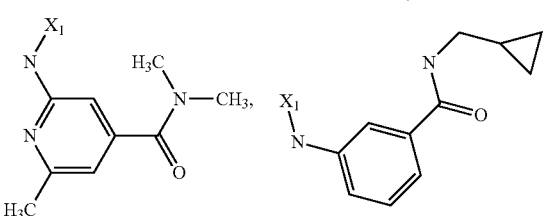
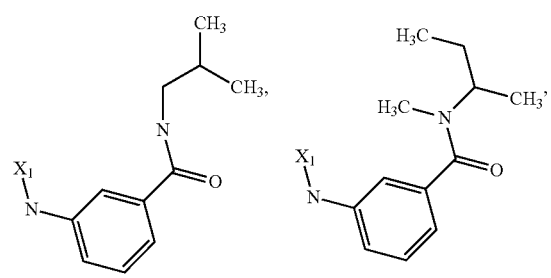
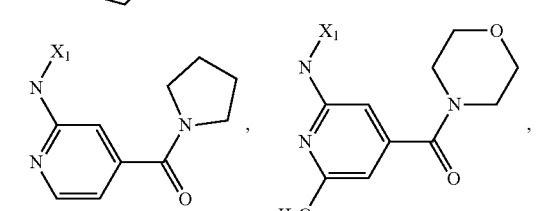
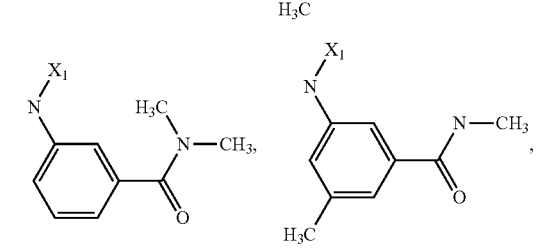
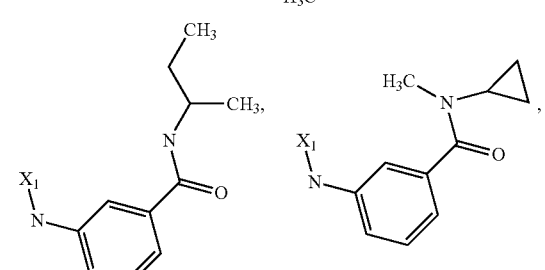
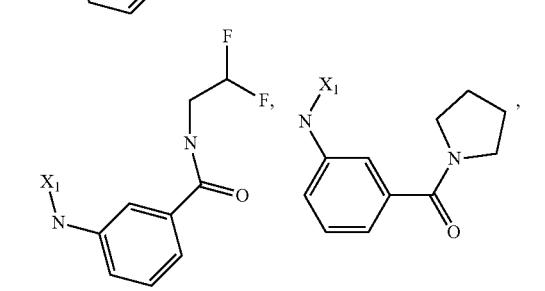
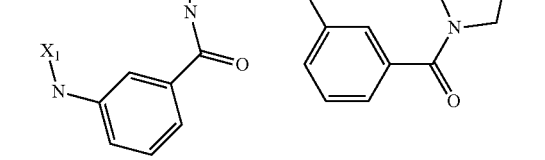
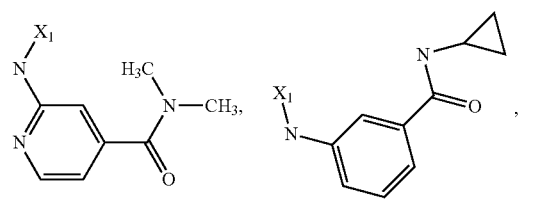
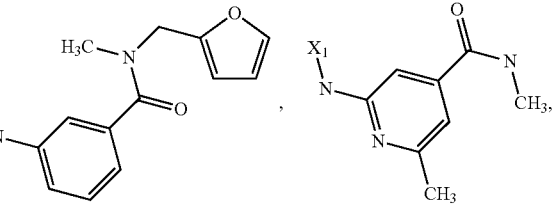
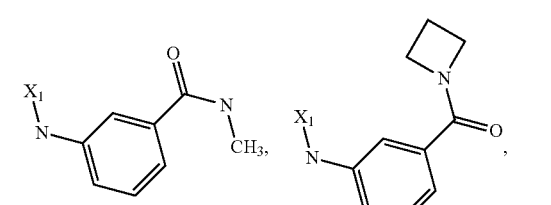
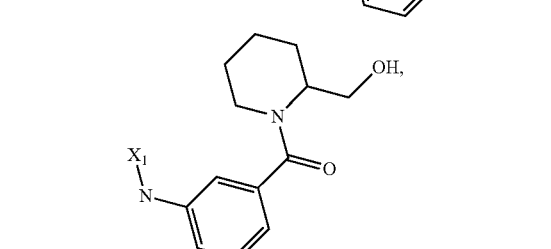
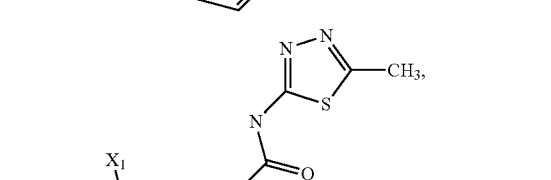
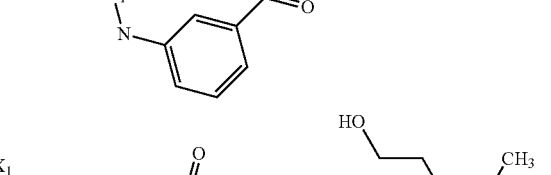
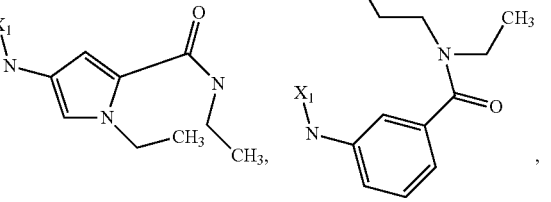
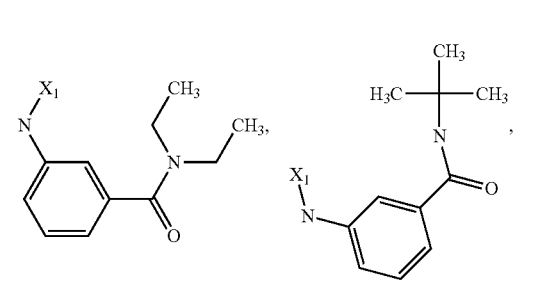

33
-continued
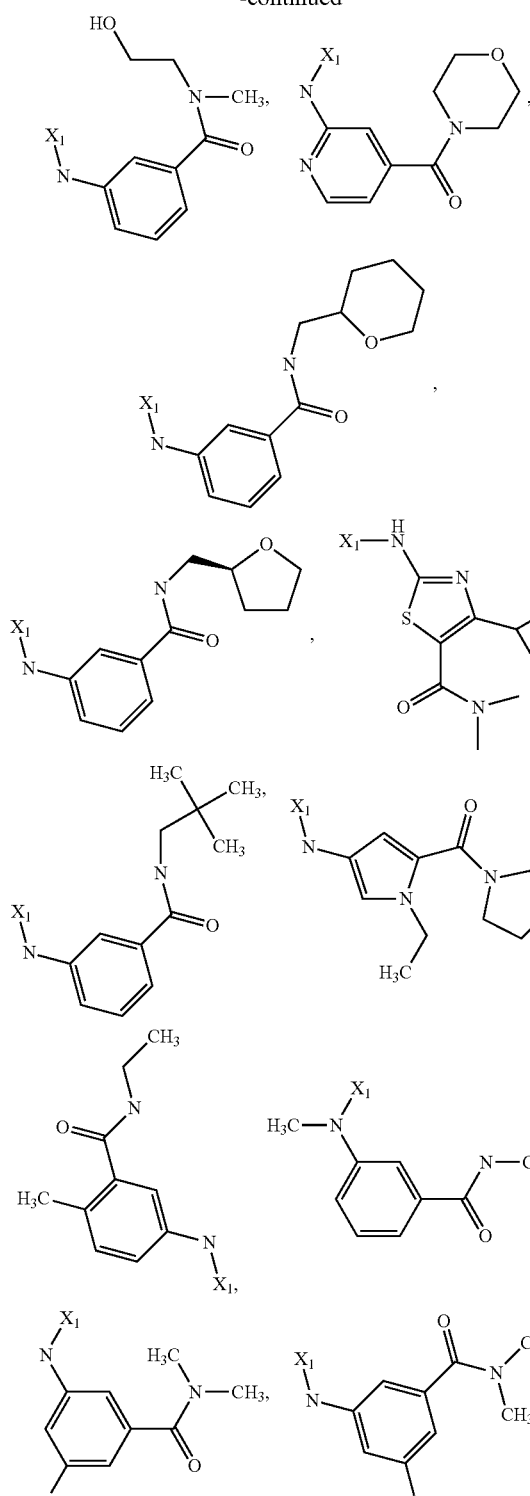
34
-continued
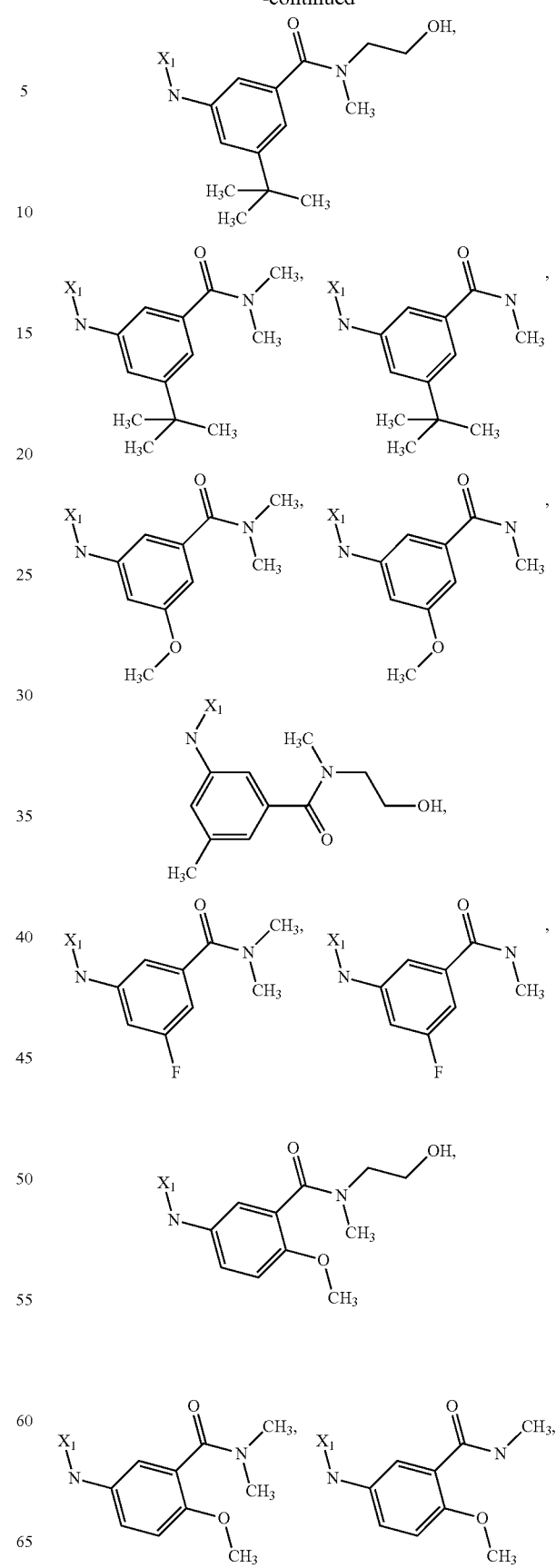

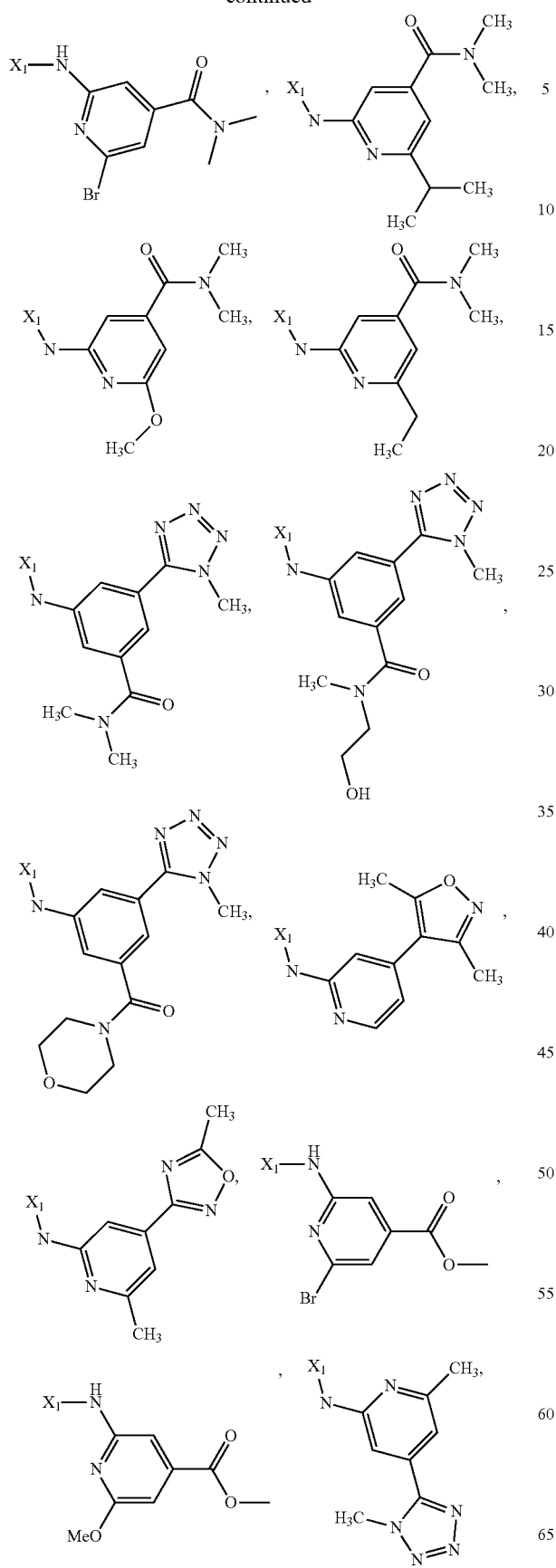
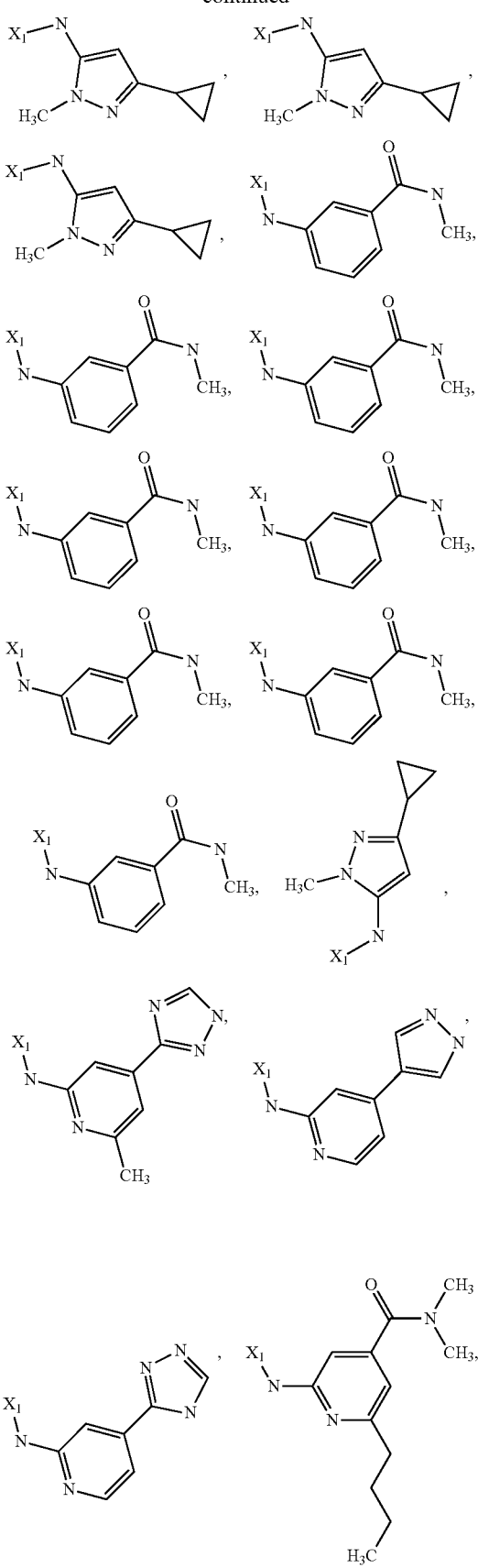

-continued
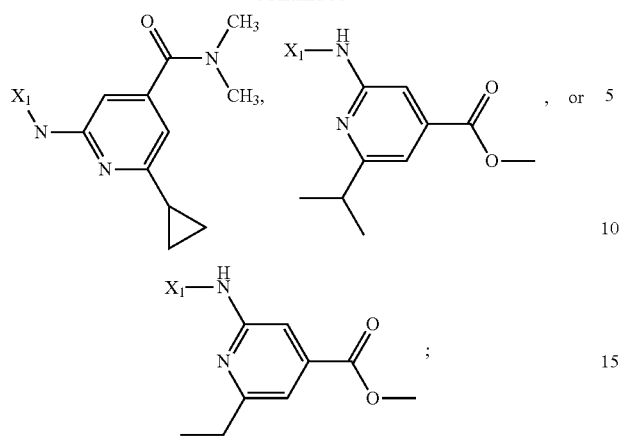
R² is selected from
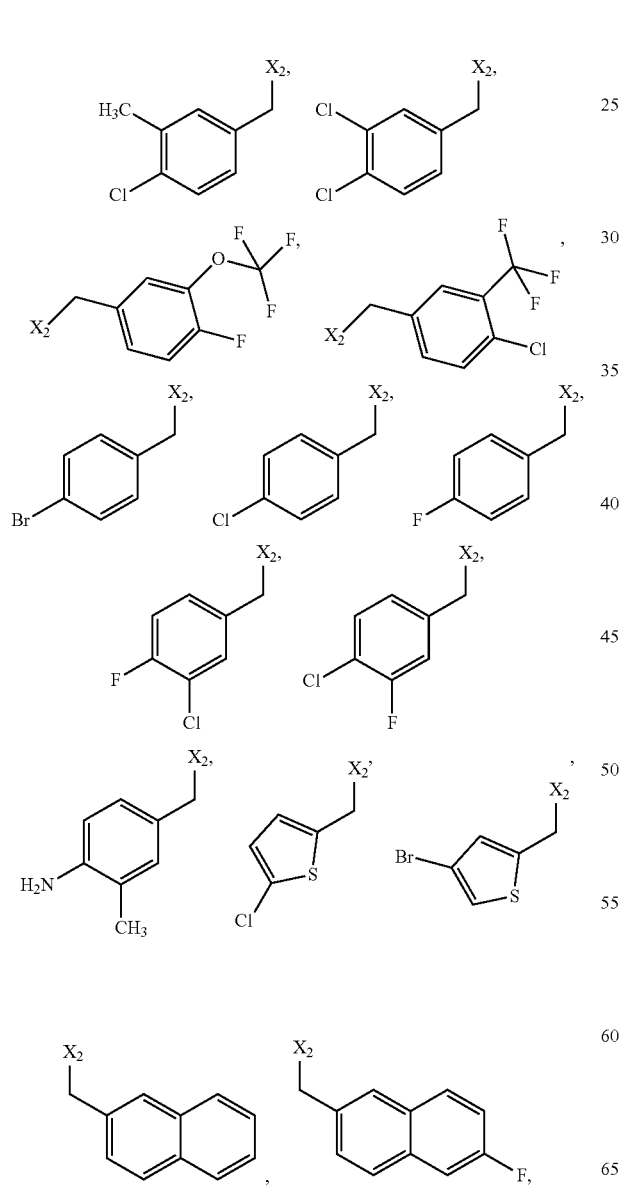
-continued
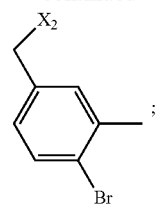
R³ is H;
R⁴ is H;
or R³ and R⁴ together are forming a CH₂—CH₂ group.
Another embodiment of the present invention are compounds of formula 1, wherein A is defined as above; R³ is H; R⁴ is H; and R² is defined as in Table 1 shown below; and R¹ is selected from
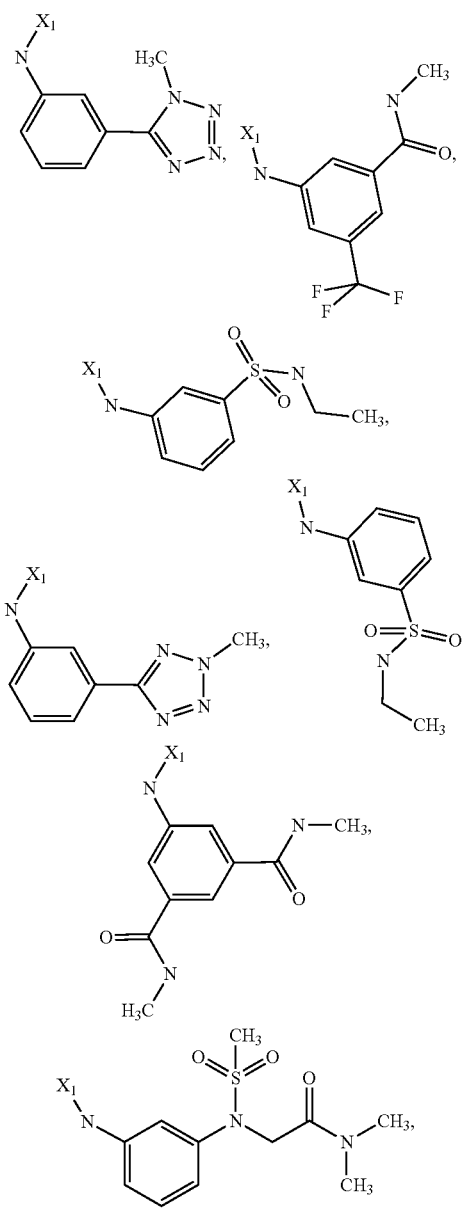

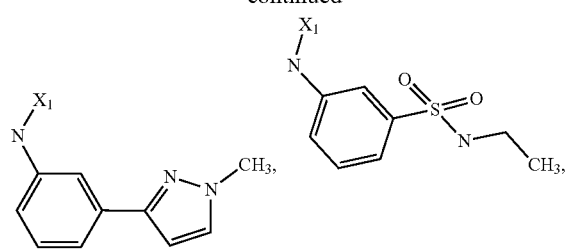
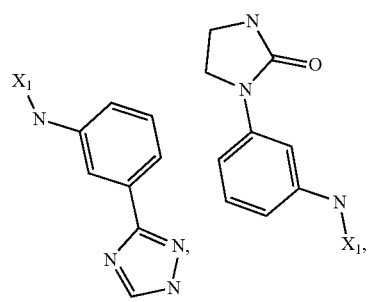
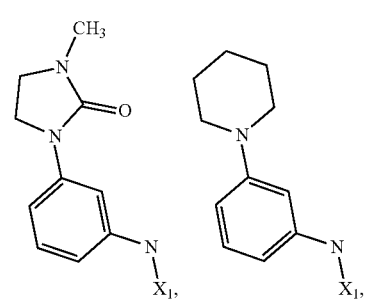
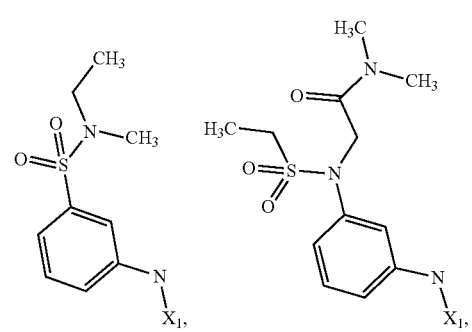
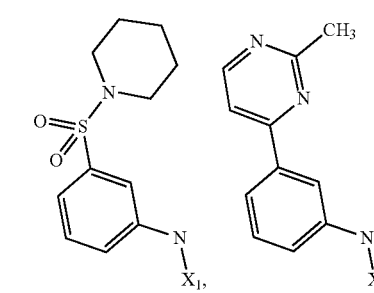
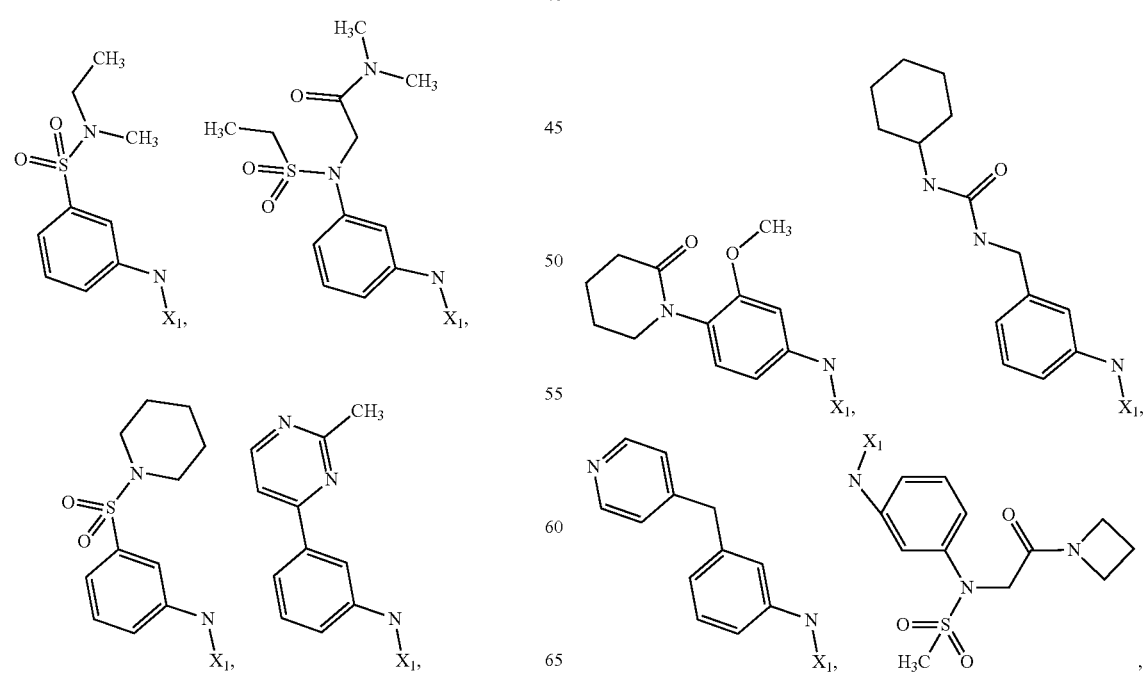

-continued
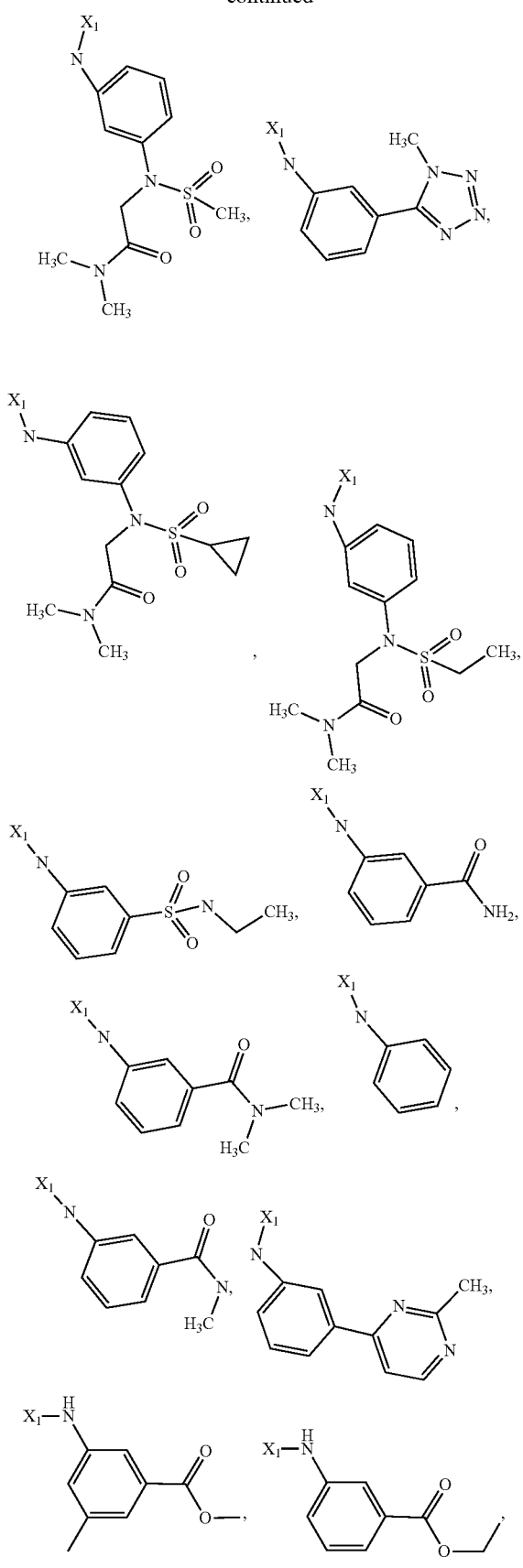
-continued
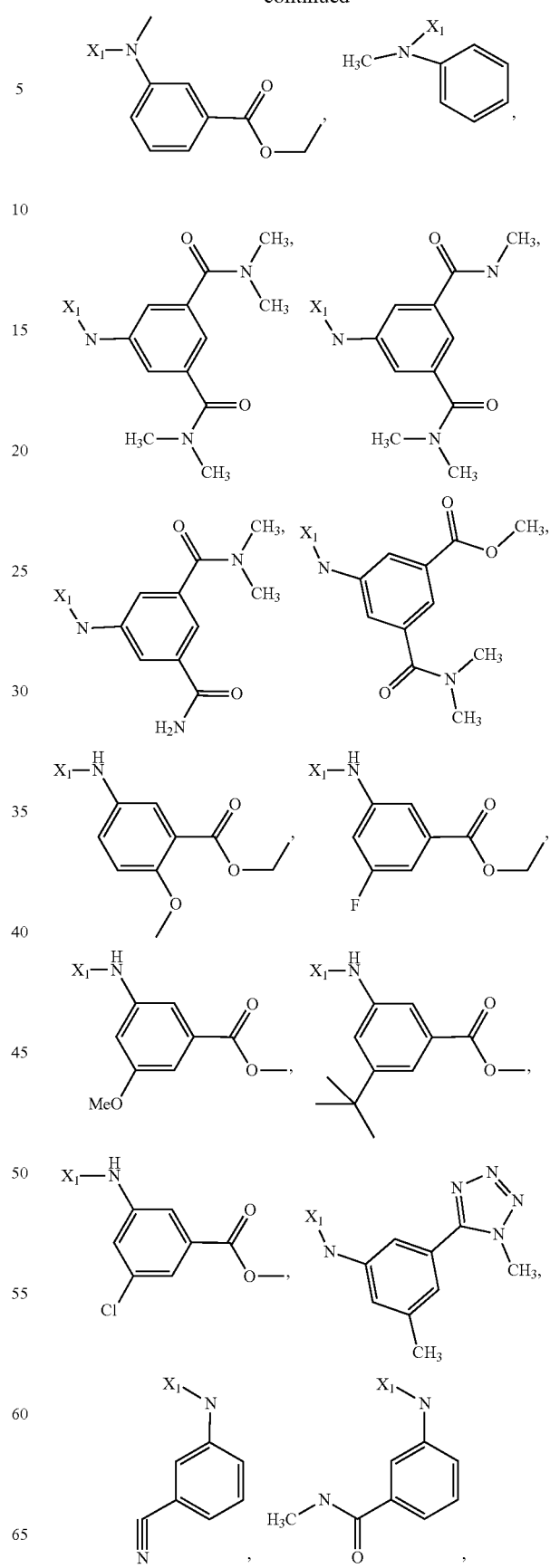

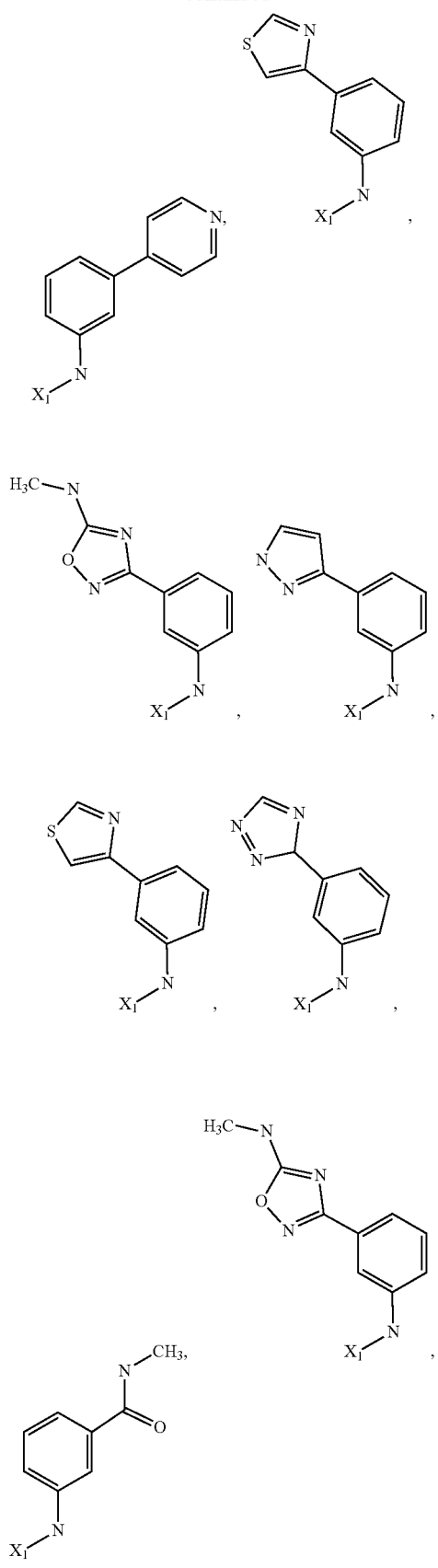
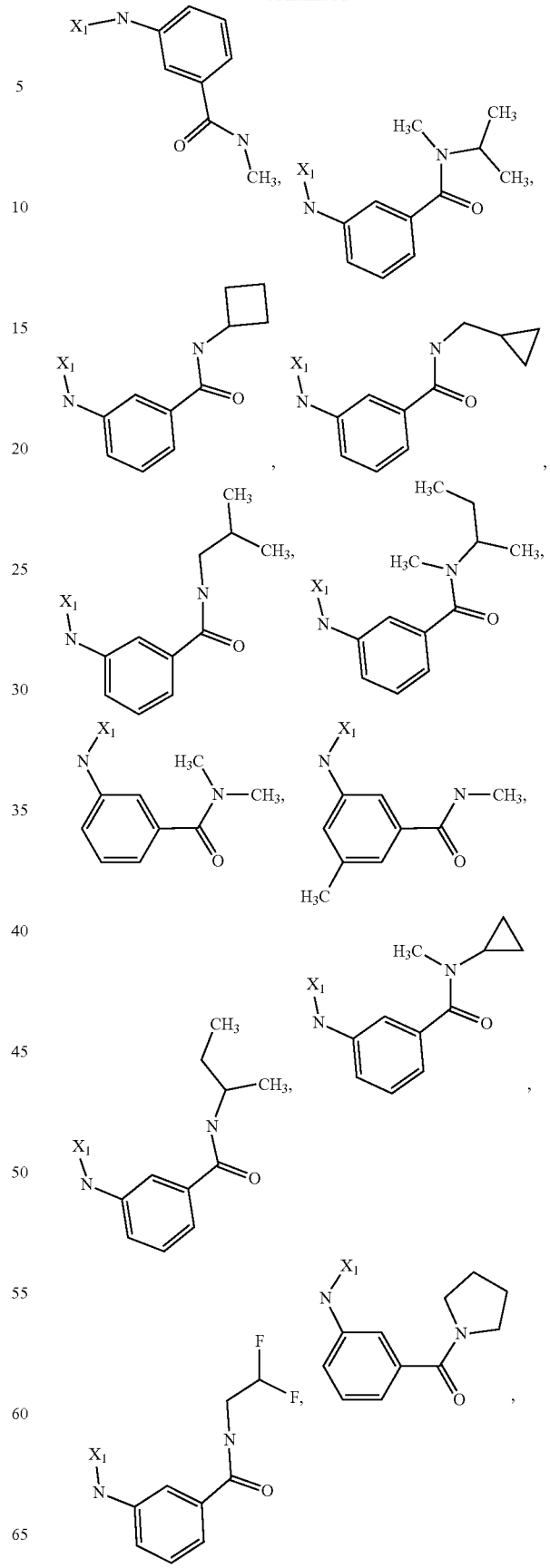

-continued
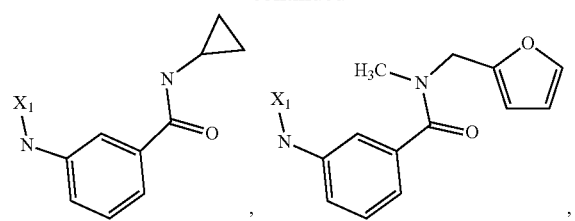
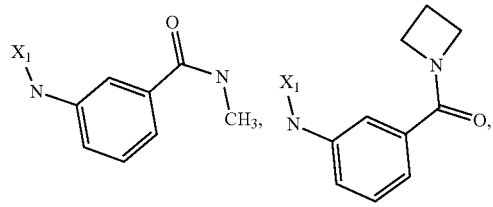
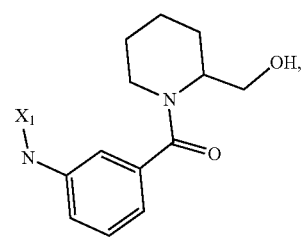
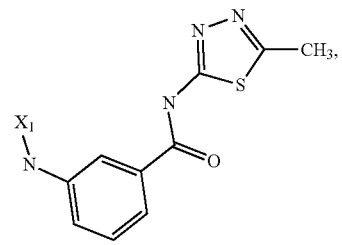
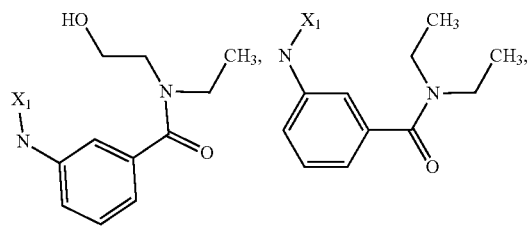
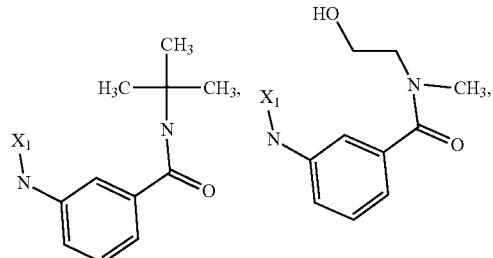
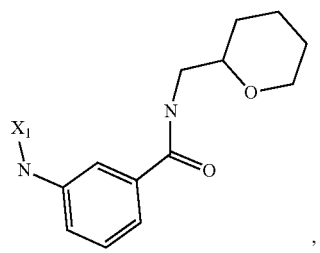
-continued
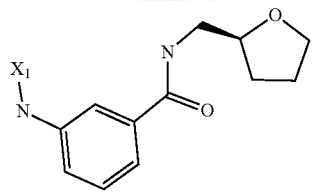
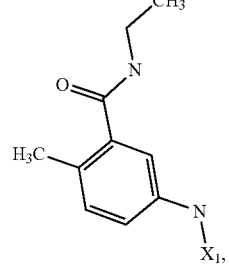
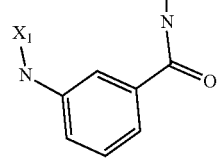
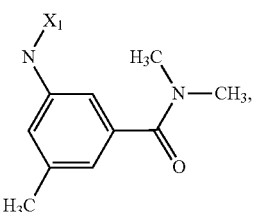
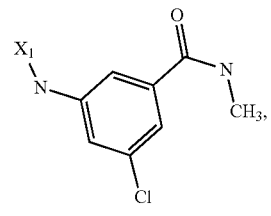
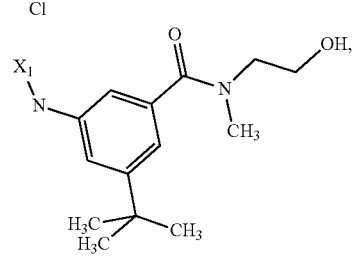
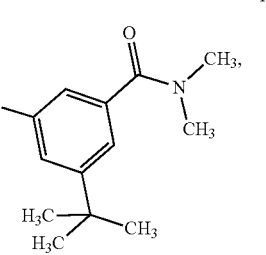

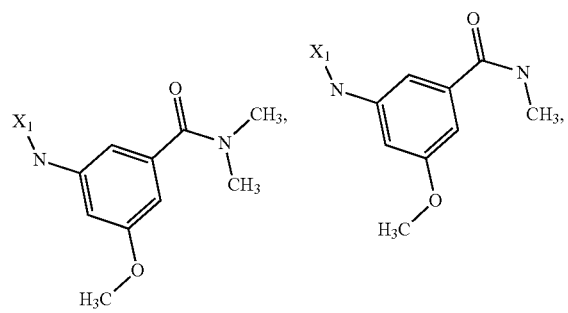
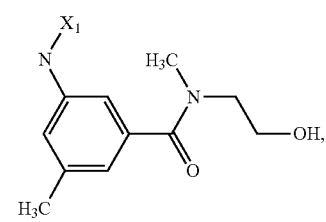
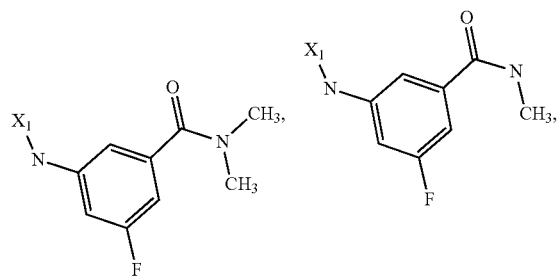
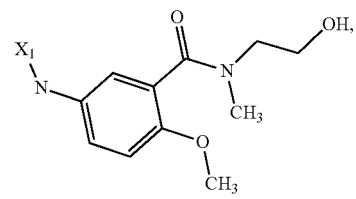
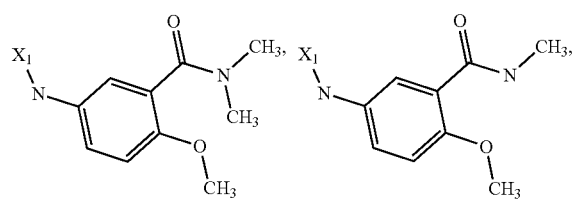
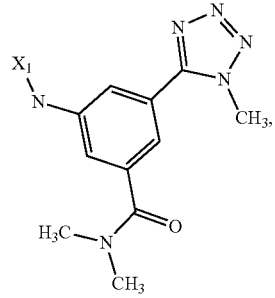
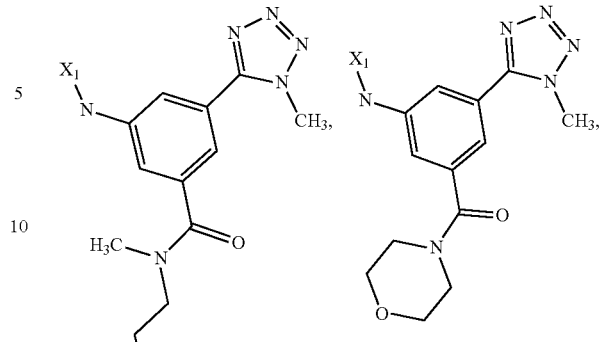
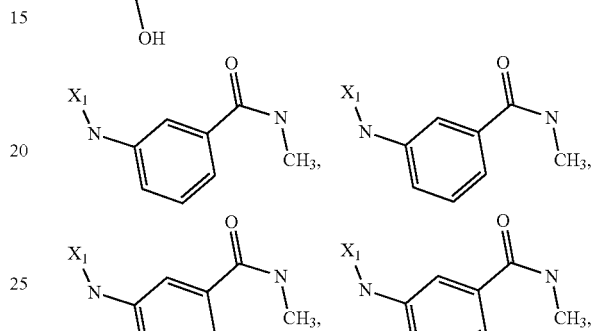
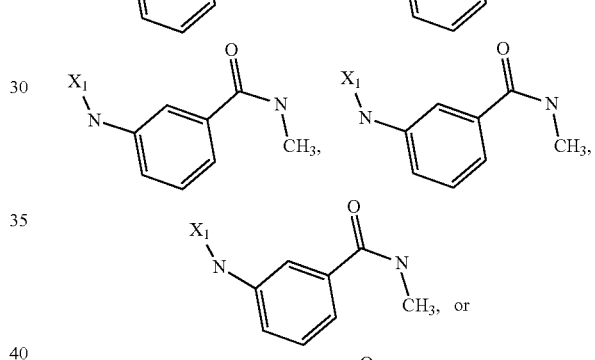
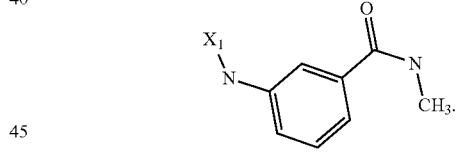
Another embodiment of the present invention further comprises administration to a subject of the compounds of formula 1, wherein A is defined as above; $R^3$ is H; $R^4$ is H; and $R^2$ is defined as in Table 1 shown below; and $R^1$ is selected from
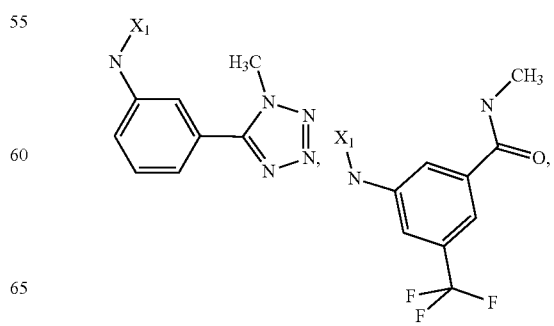

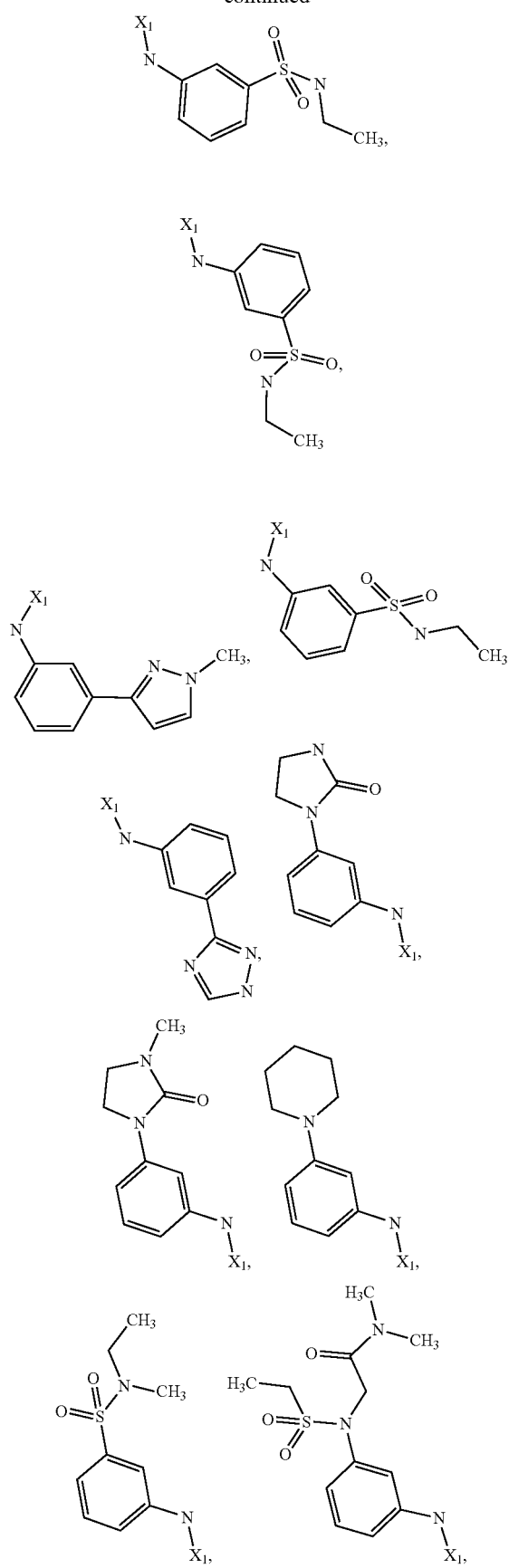
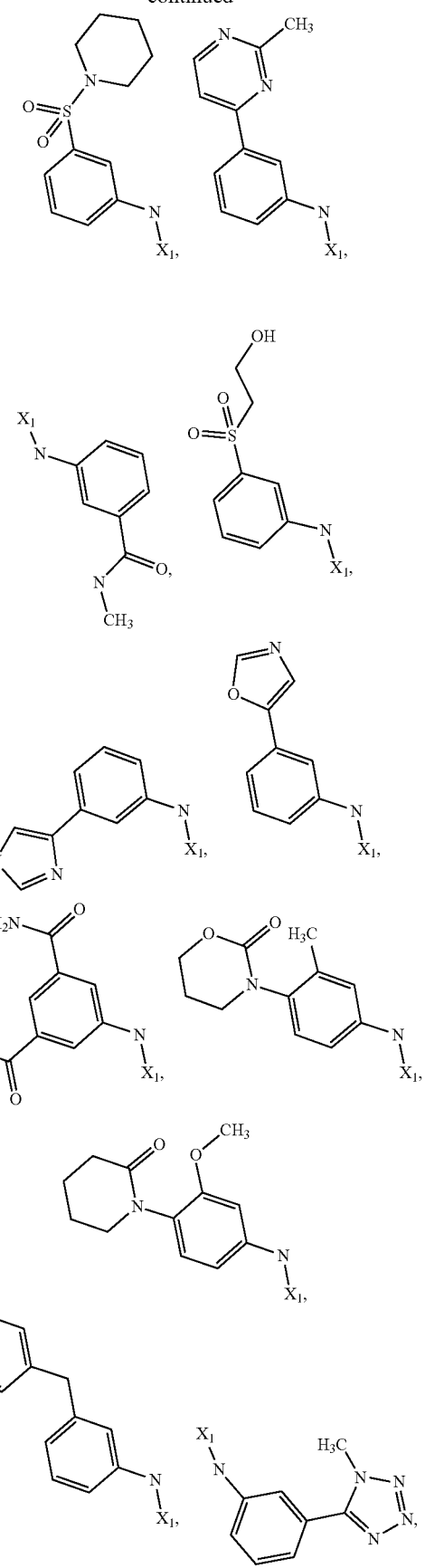

-continued
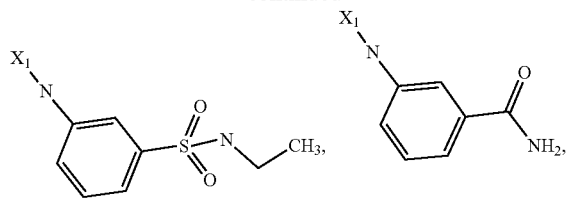
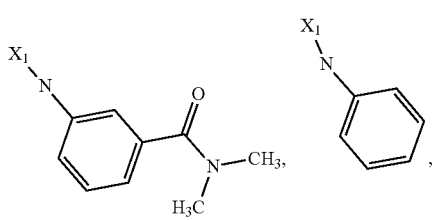
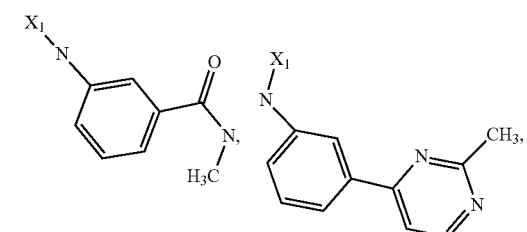
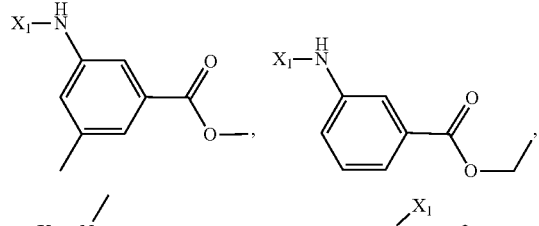
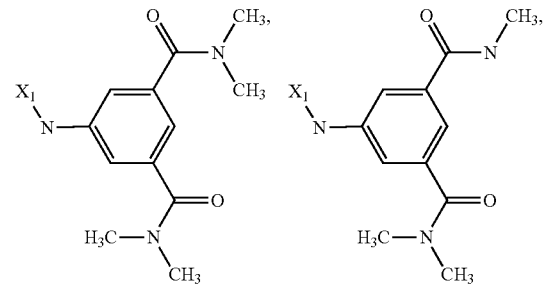
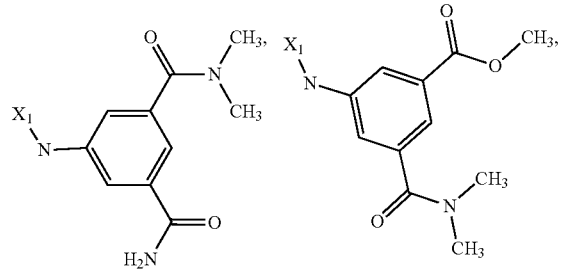
-continued
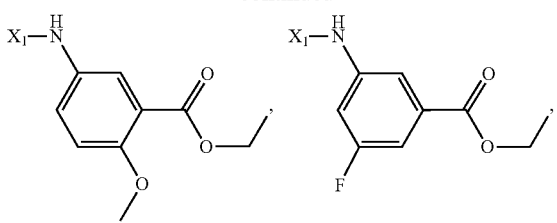
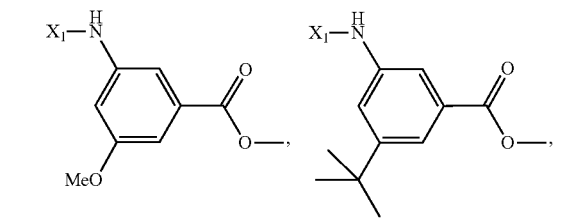
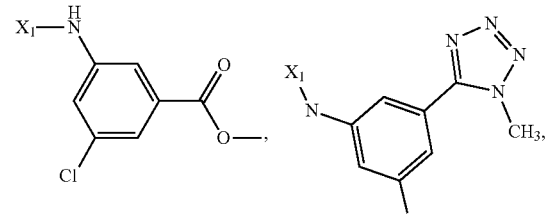
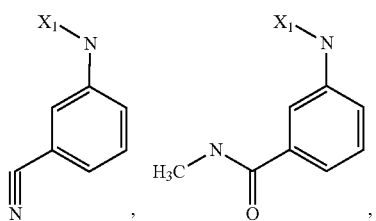
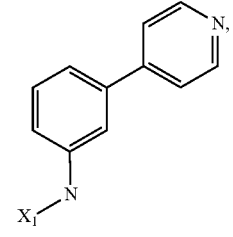
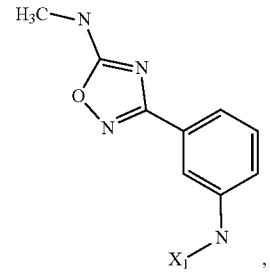

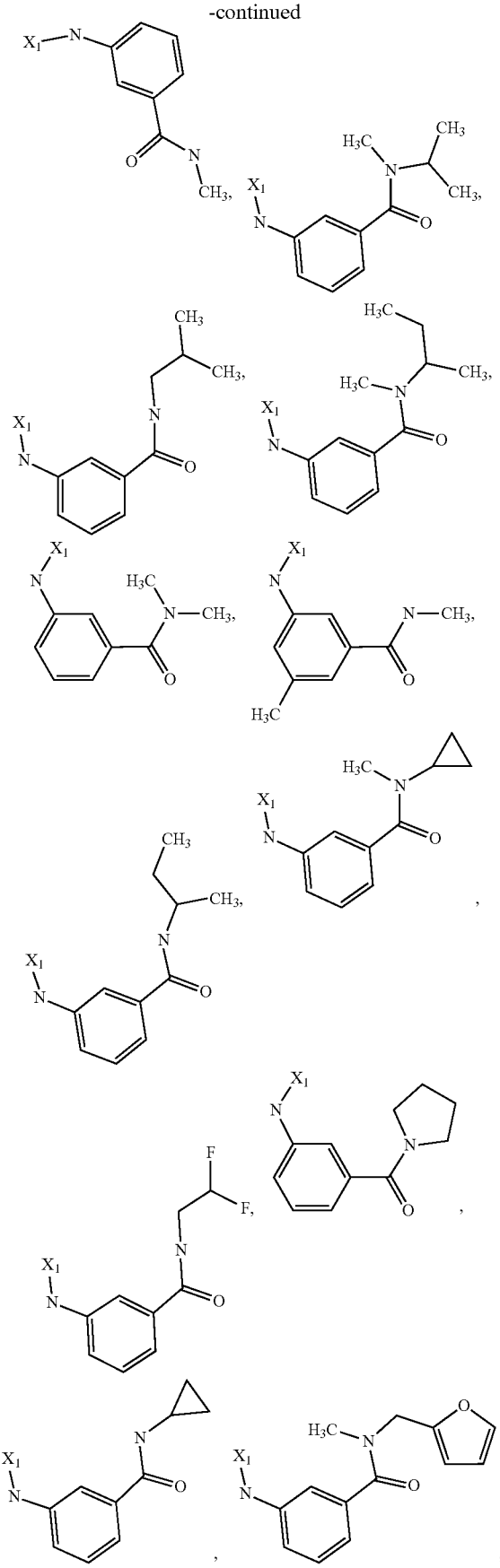
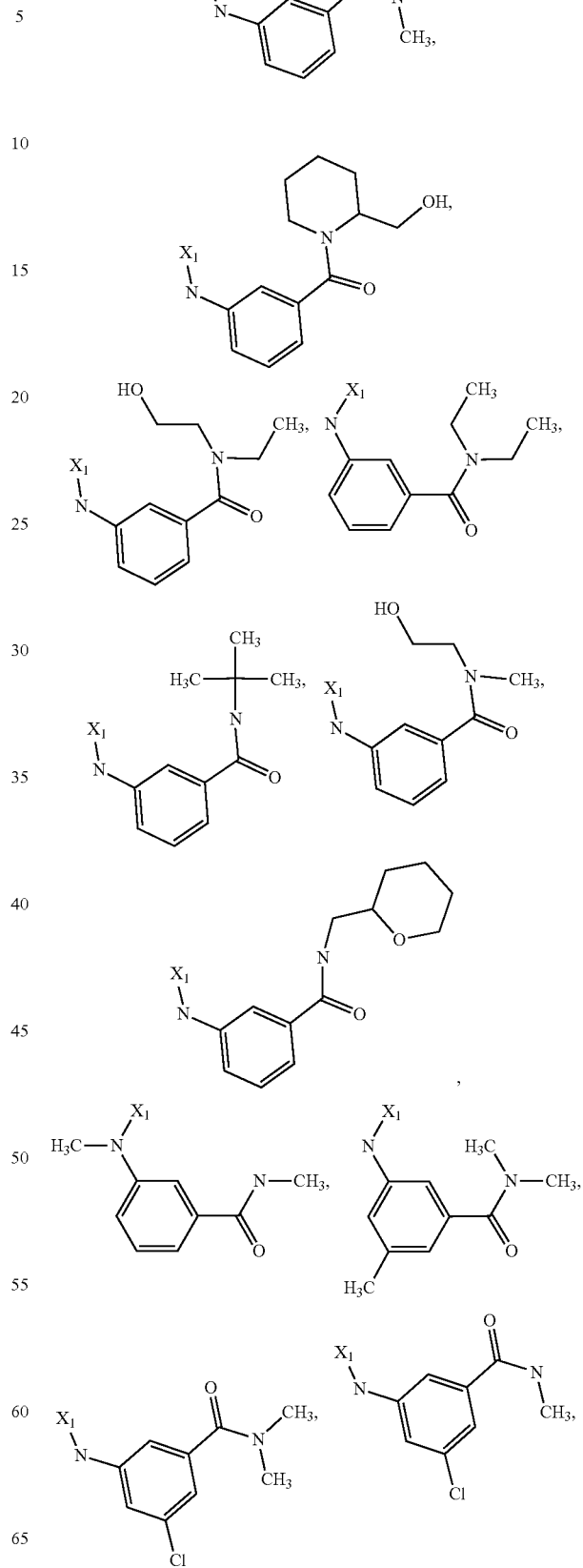

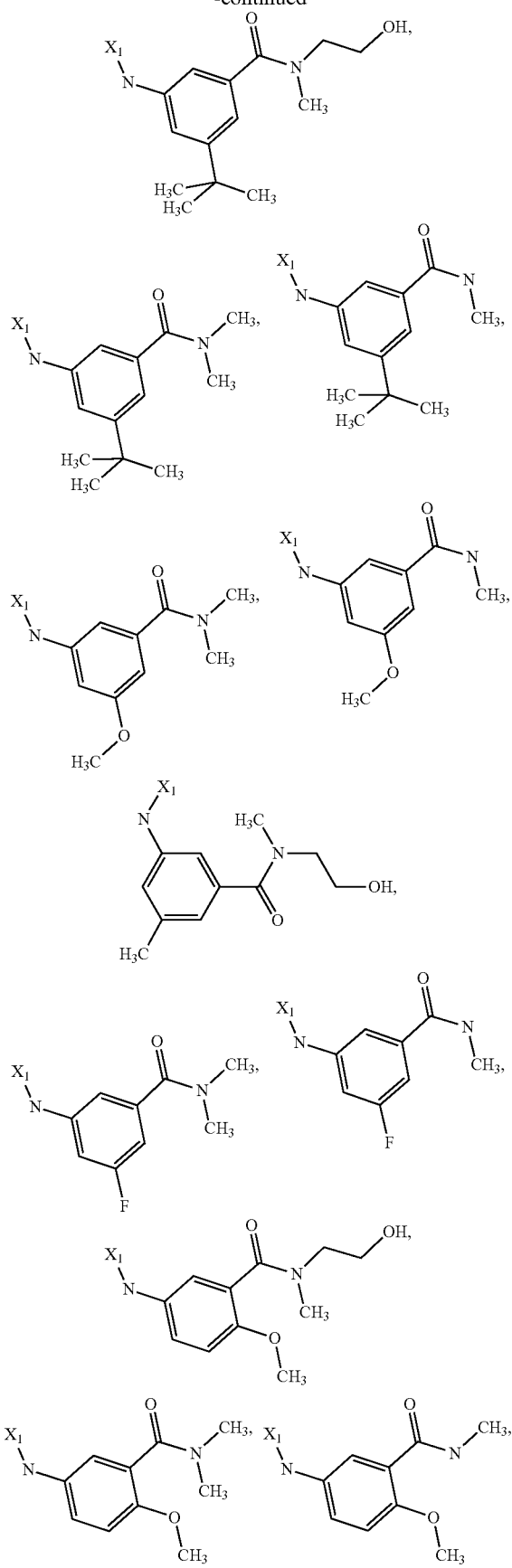
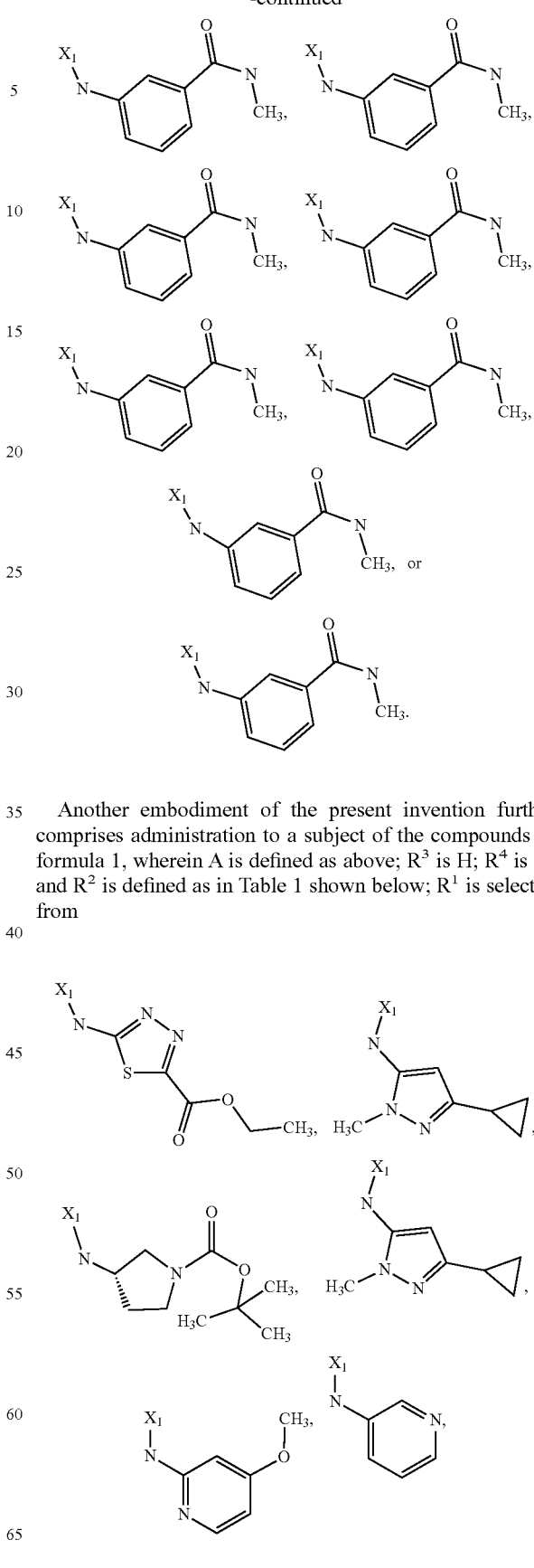
Another embodiment of the present invention further comprises administration to a subject of the compounds of formula 1, wherein A is defined as above; $R^3$ is H; $R^4$ is H; and $R^2$ is defined as in Table 1 shown below; $R^1$ is selected from -continued
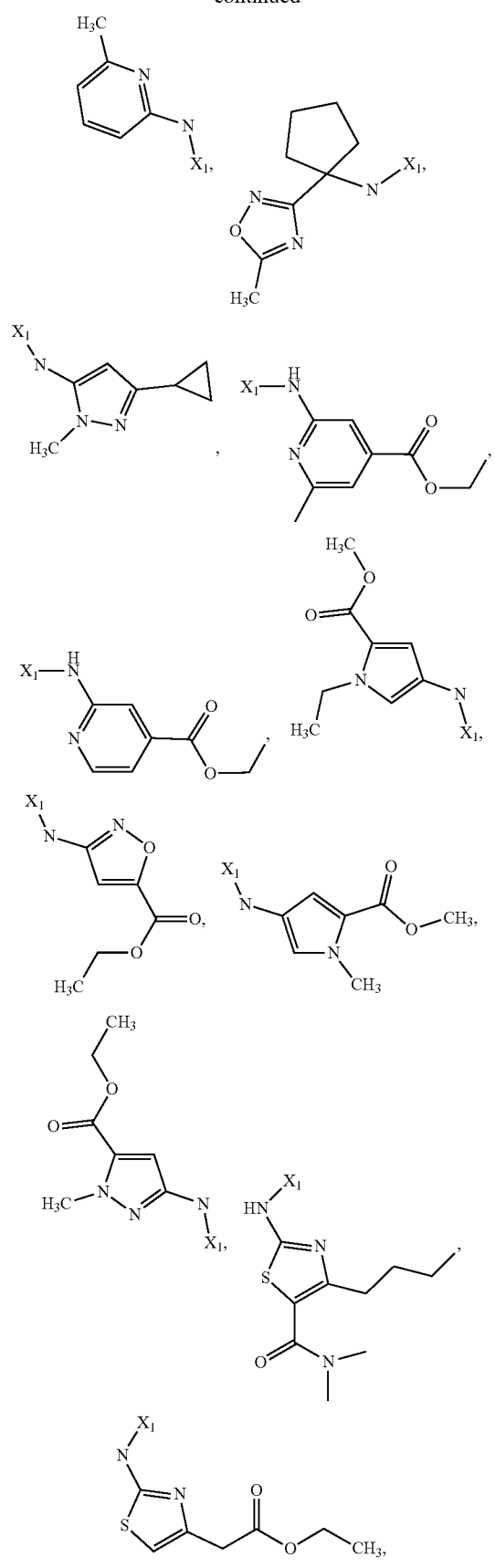
-continued
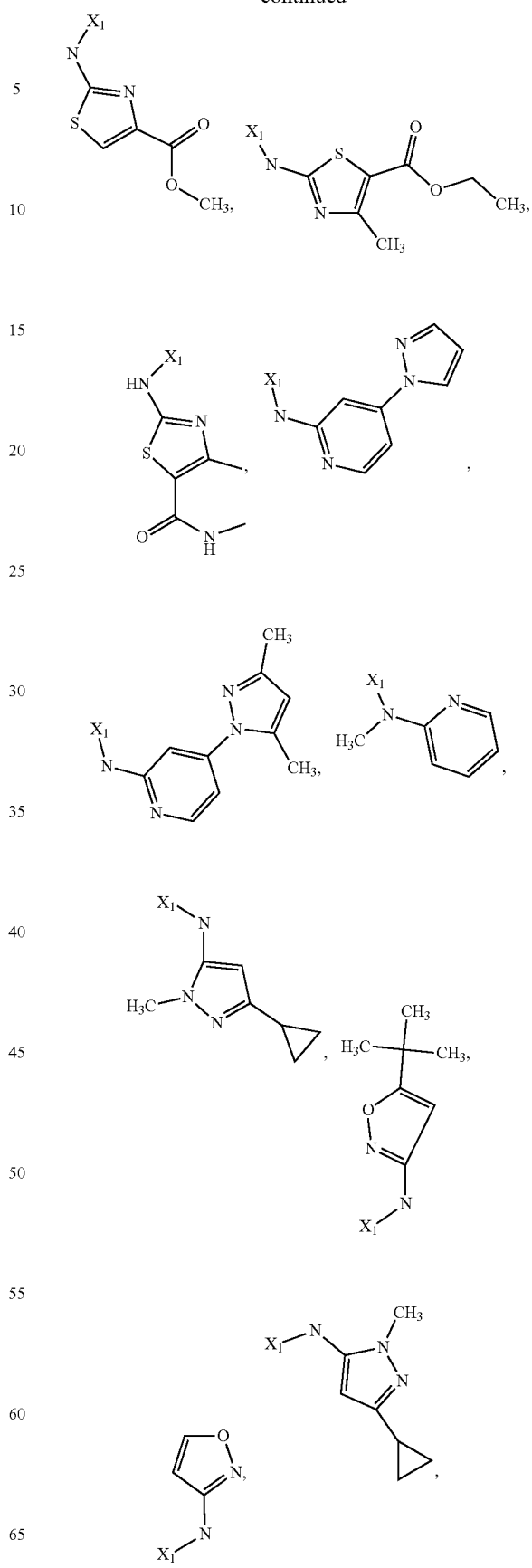

-continued
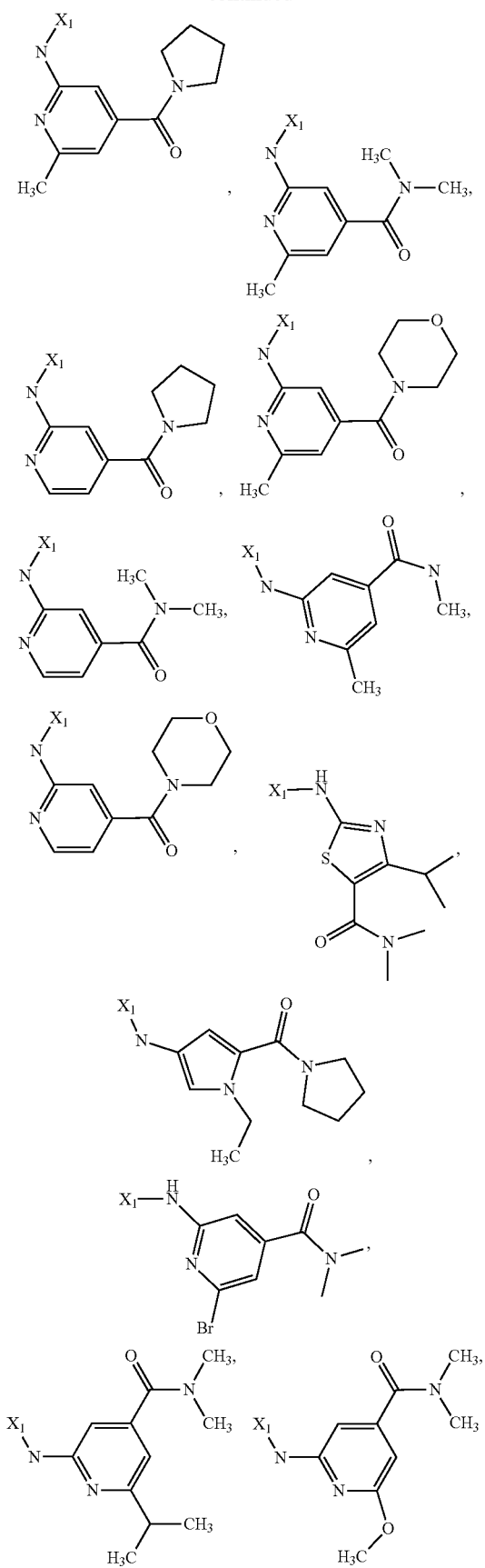
-continued
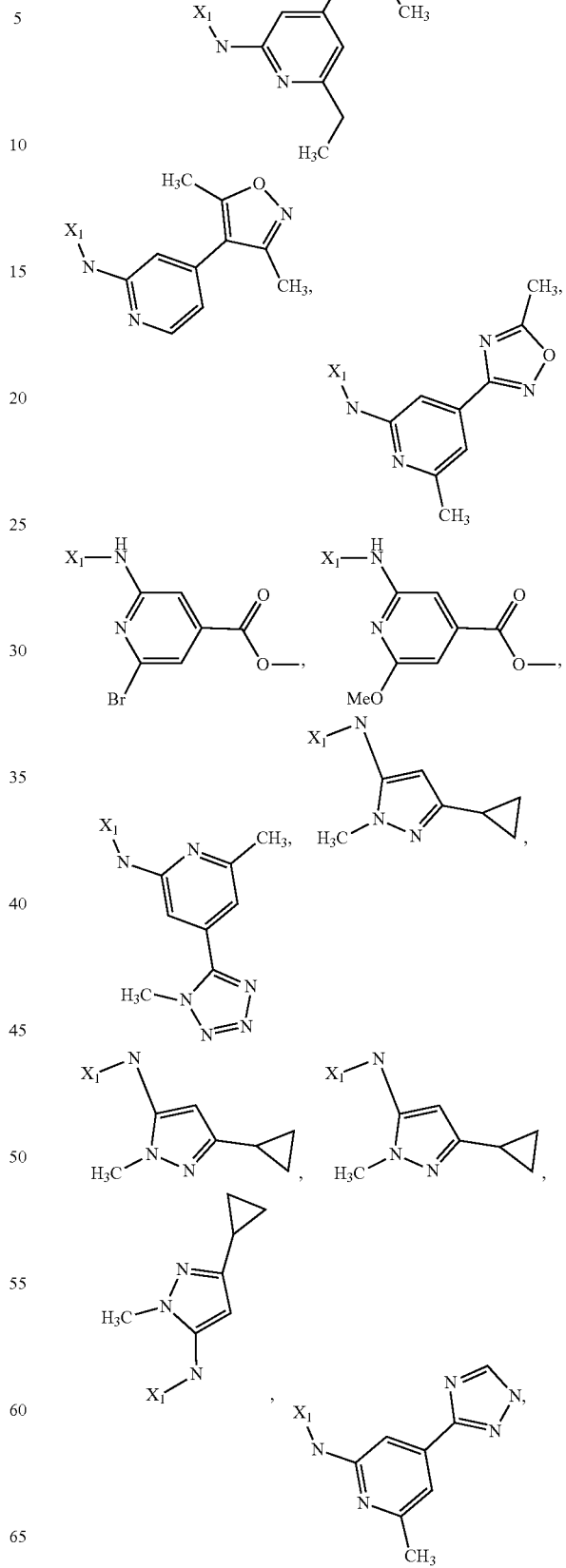

-continued
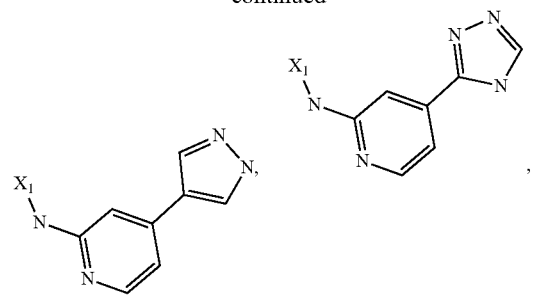
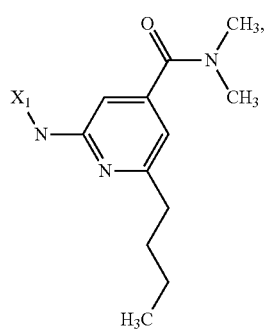
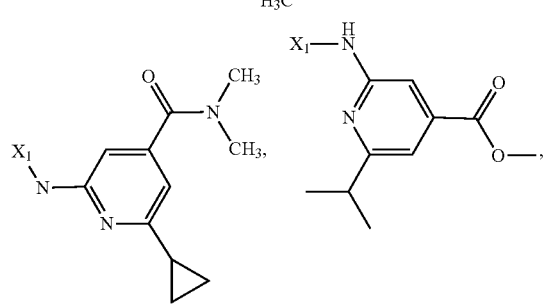
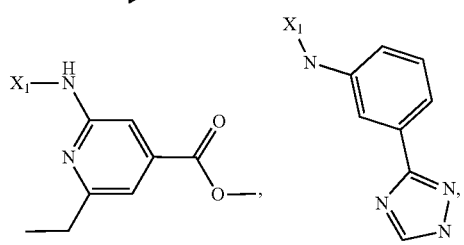
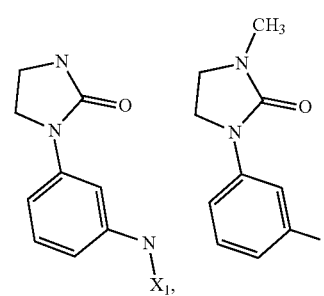
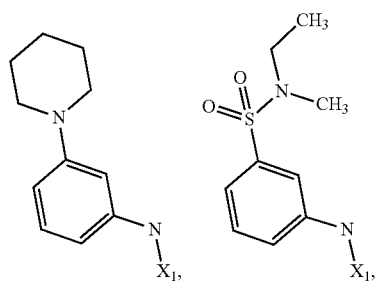
-continued
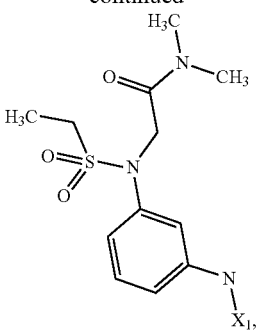
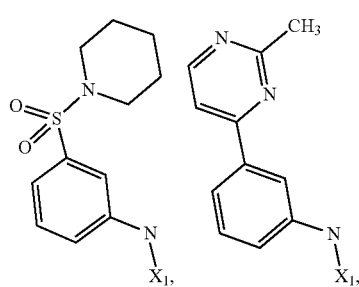
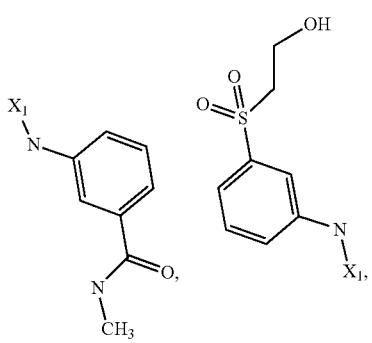
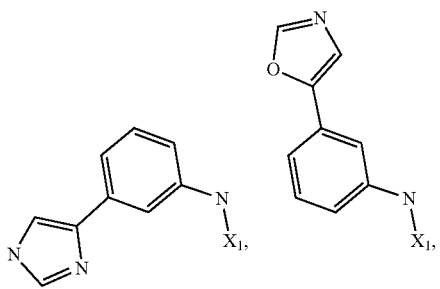
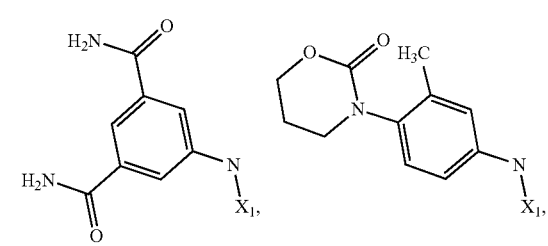

-continued
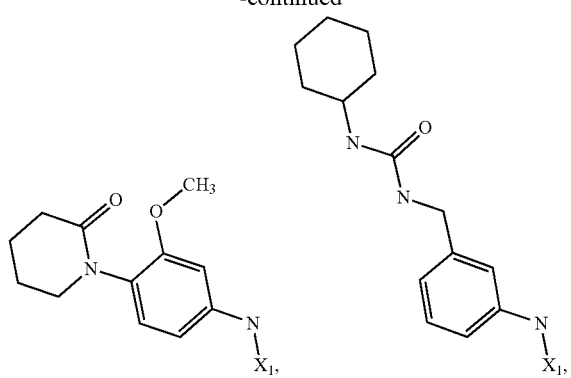
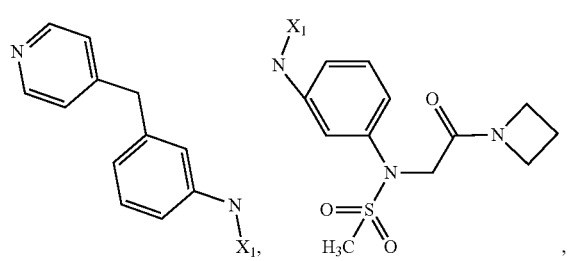
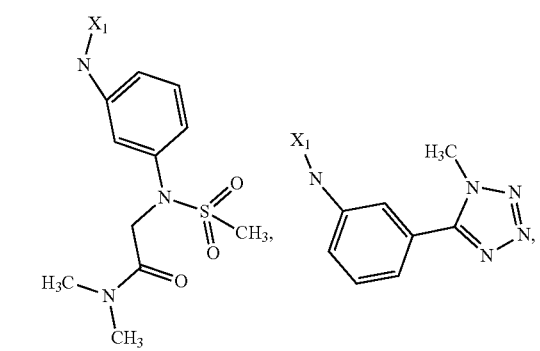
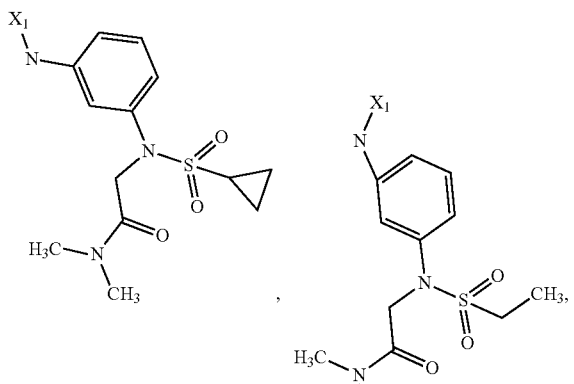
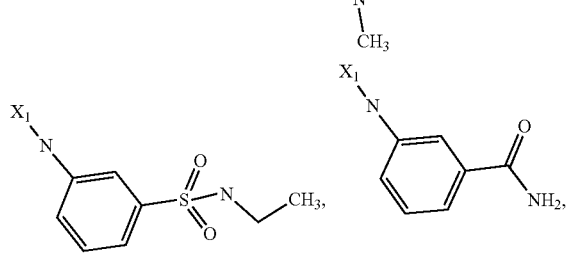
-continued
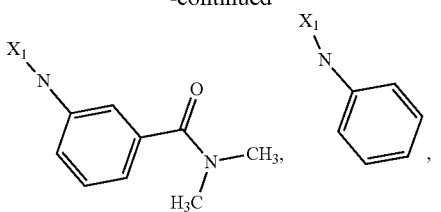
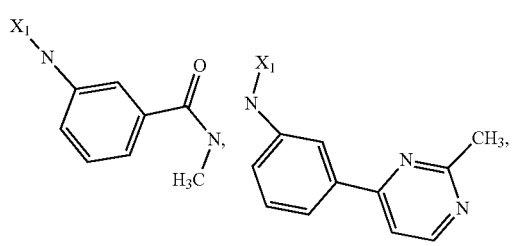
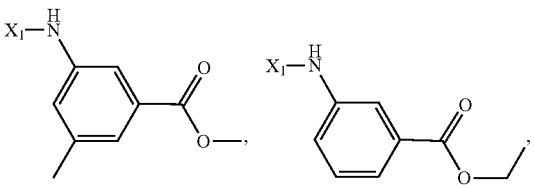
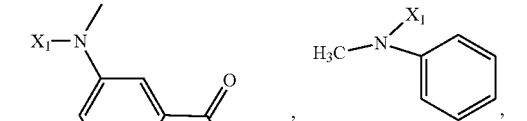
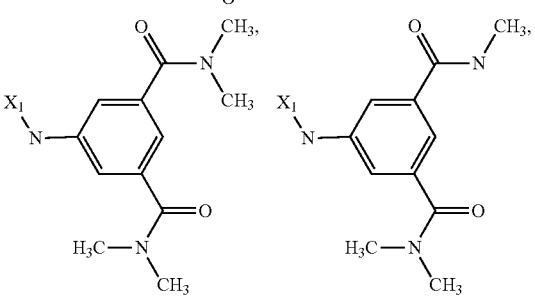
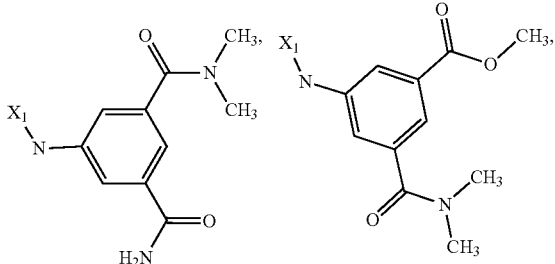
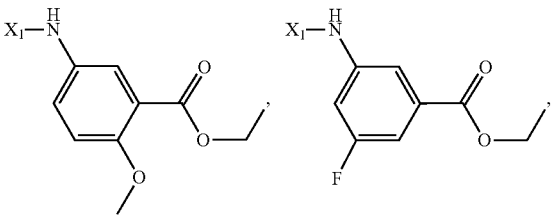

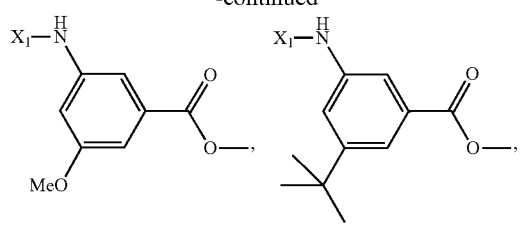
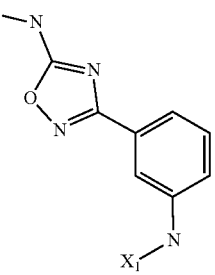
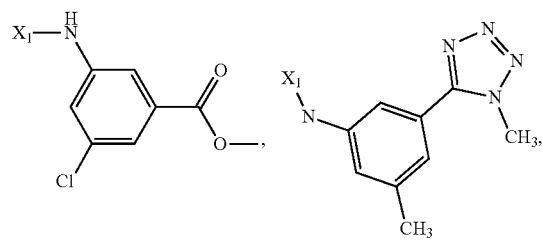
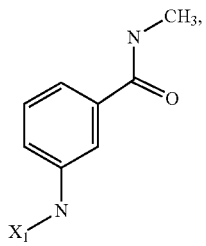
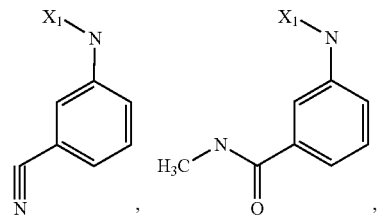
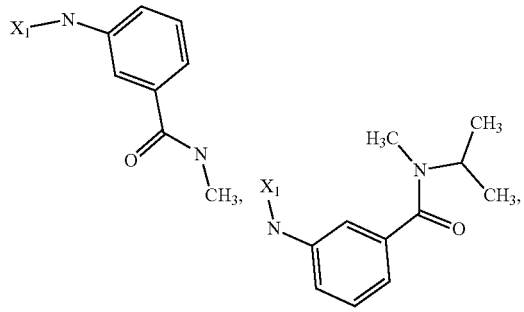
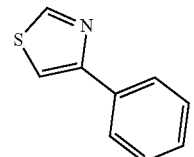
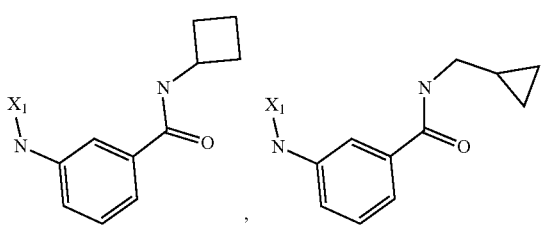
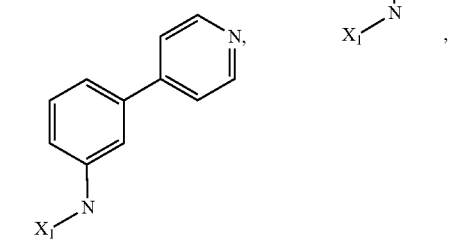
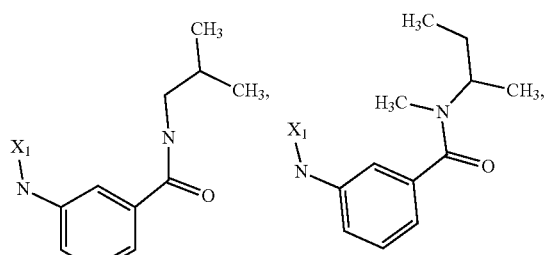
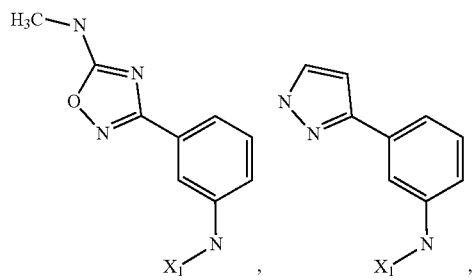
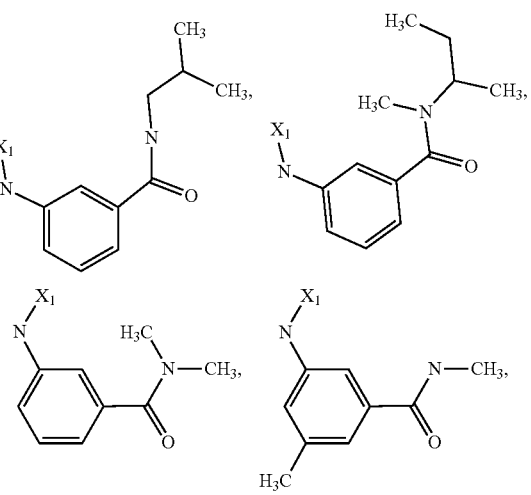
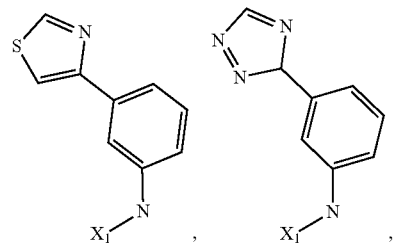

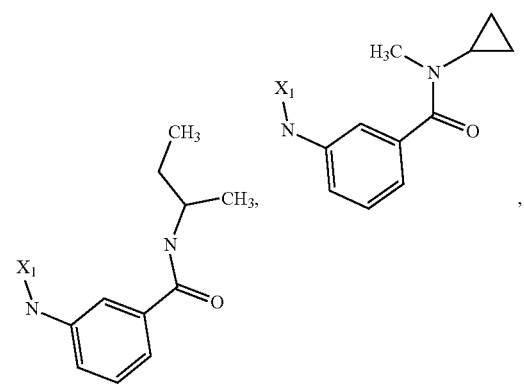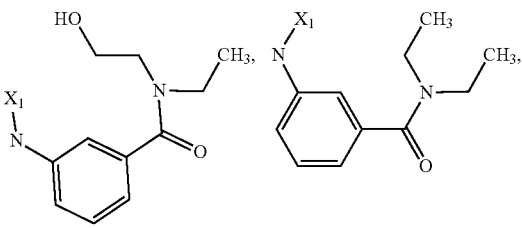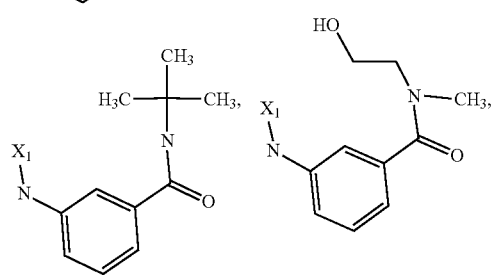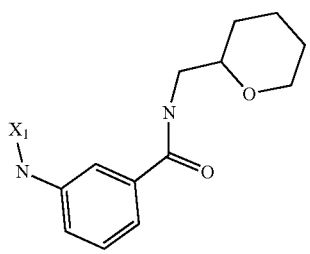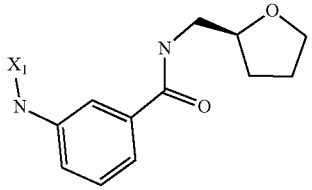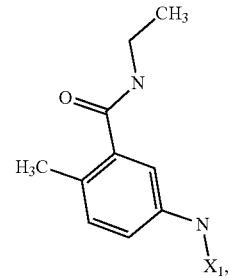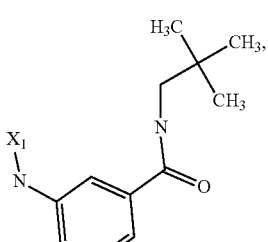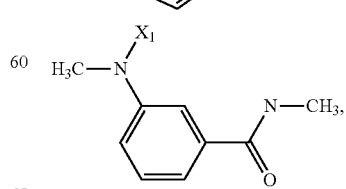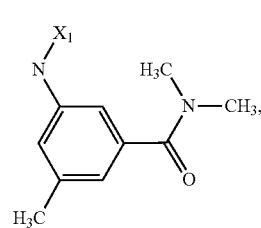

-continued
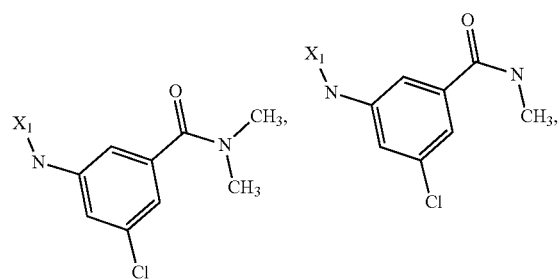
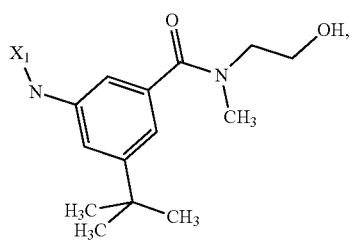
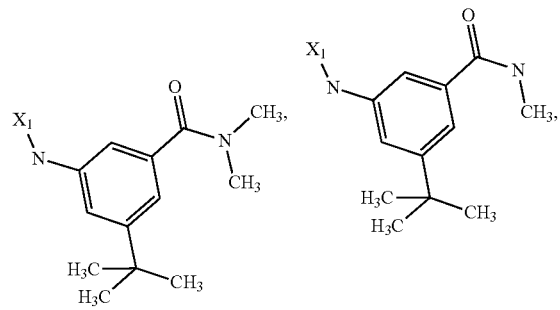
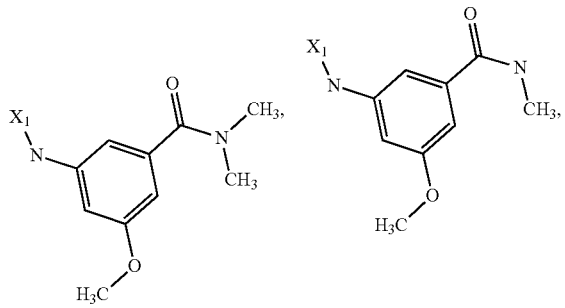
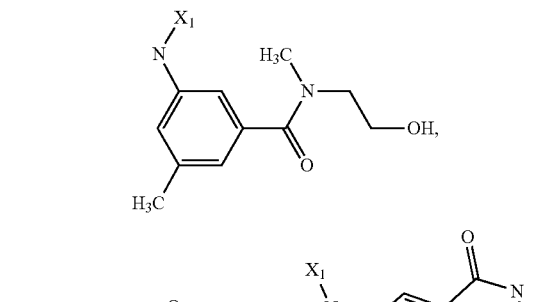
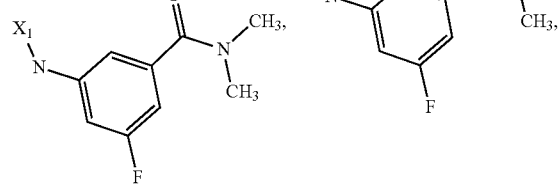
-continued
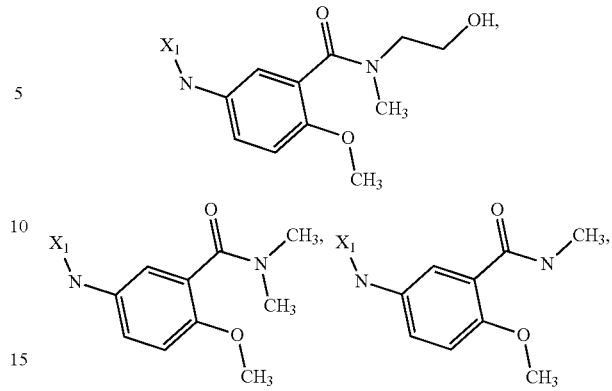
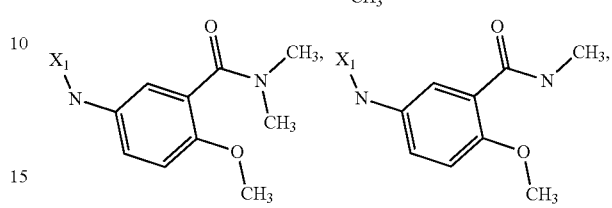
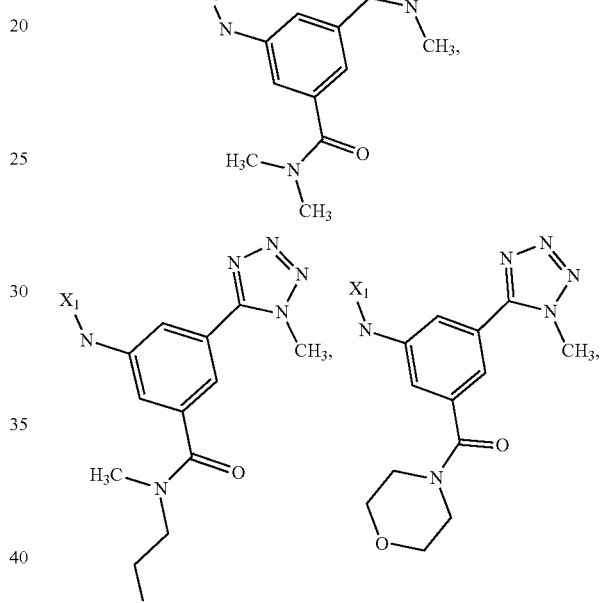
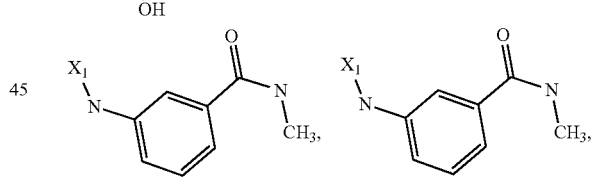
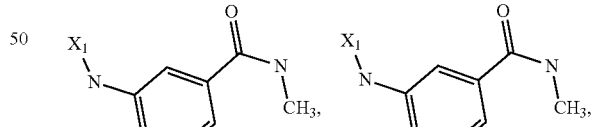
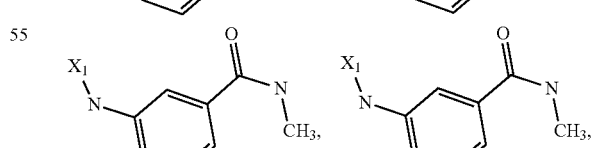
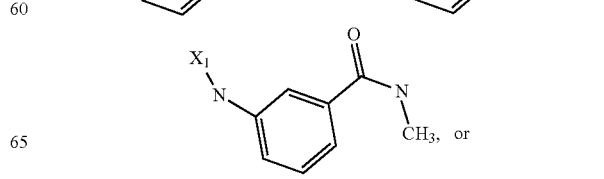, or 71
-continued
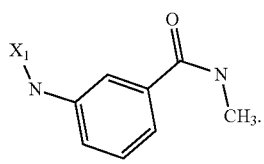
Another embodiment of the present invention further comprises administration to a subject of the compounds of formula 1, wherein A is defined as above; $R^3$ is H; $R^4$ is H; and $R^2$ is defined as in Table 1 shown below; and $R^1$ is selected from
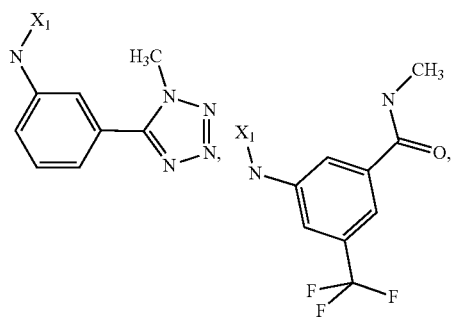
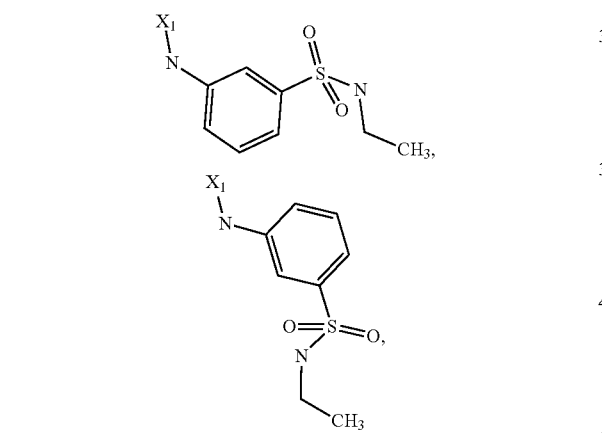
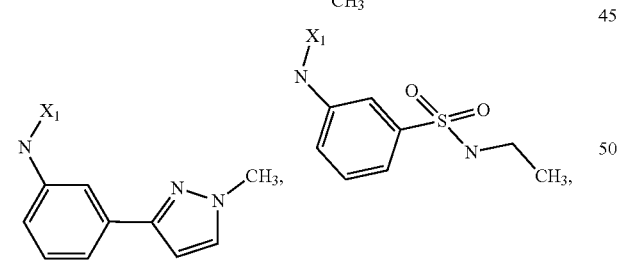
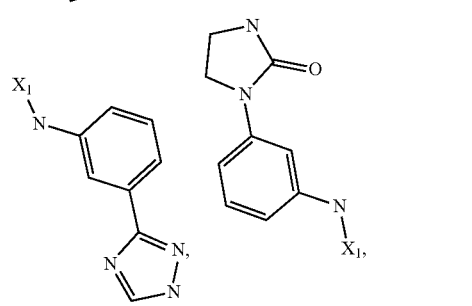
72
-continued
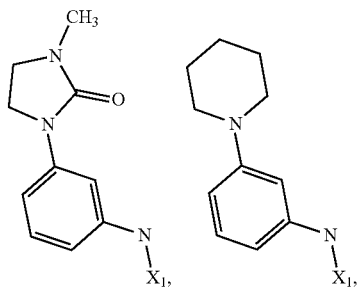
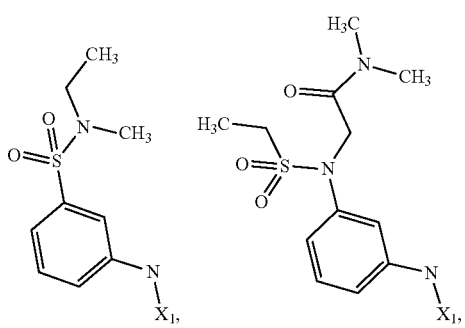
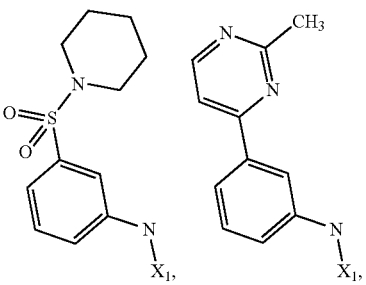
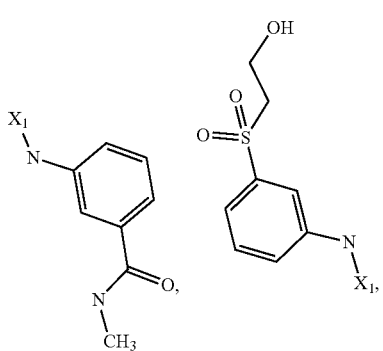
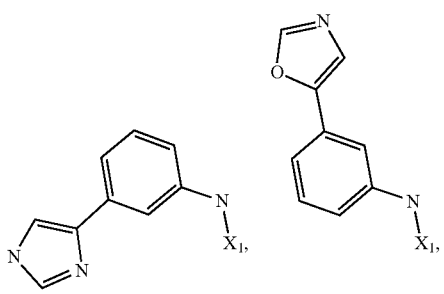

-continued
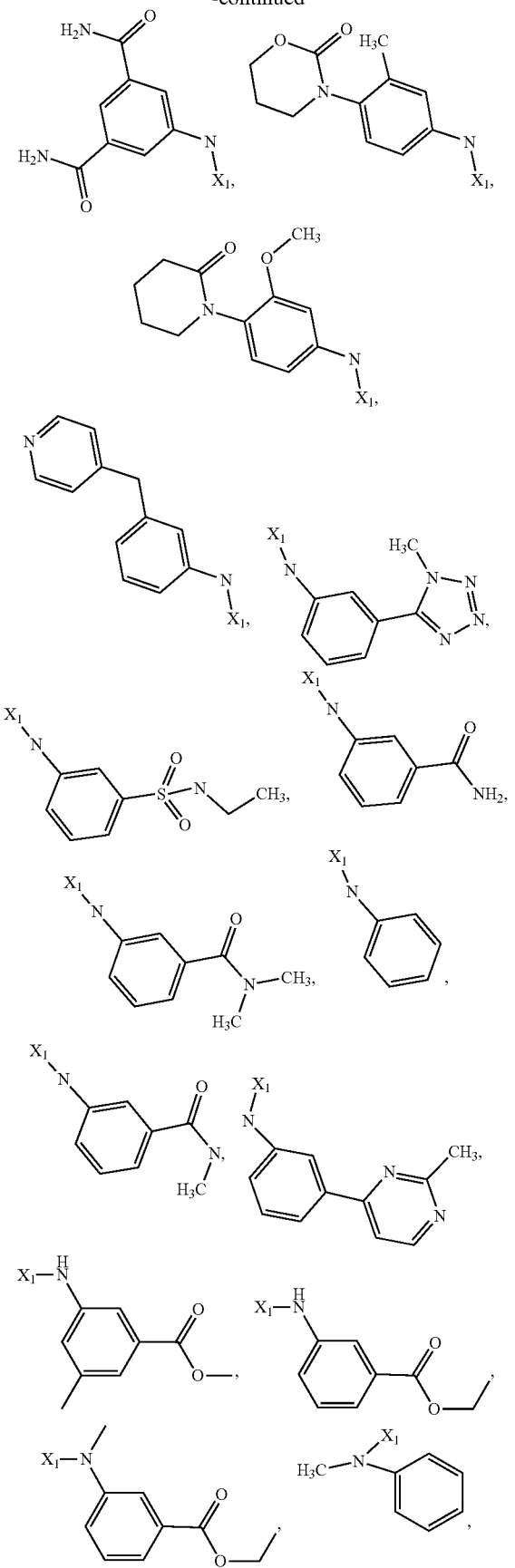
-continued
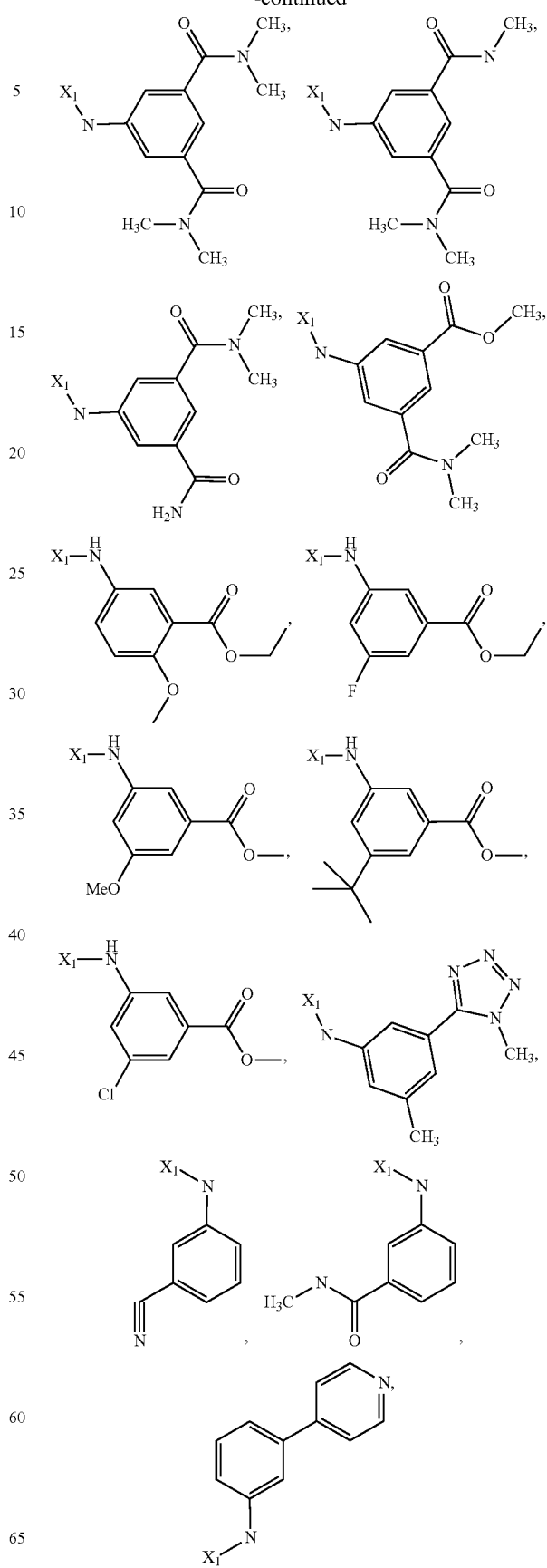

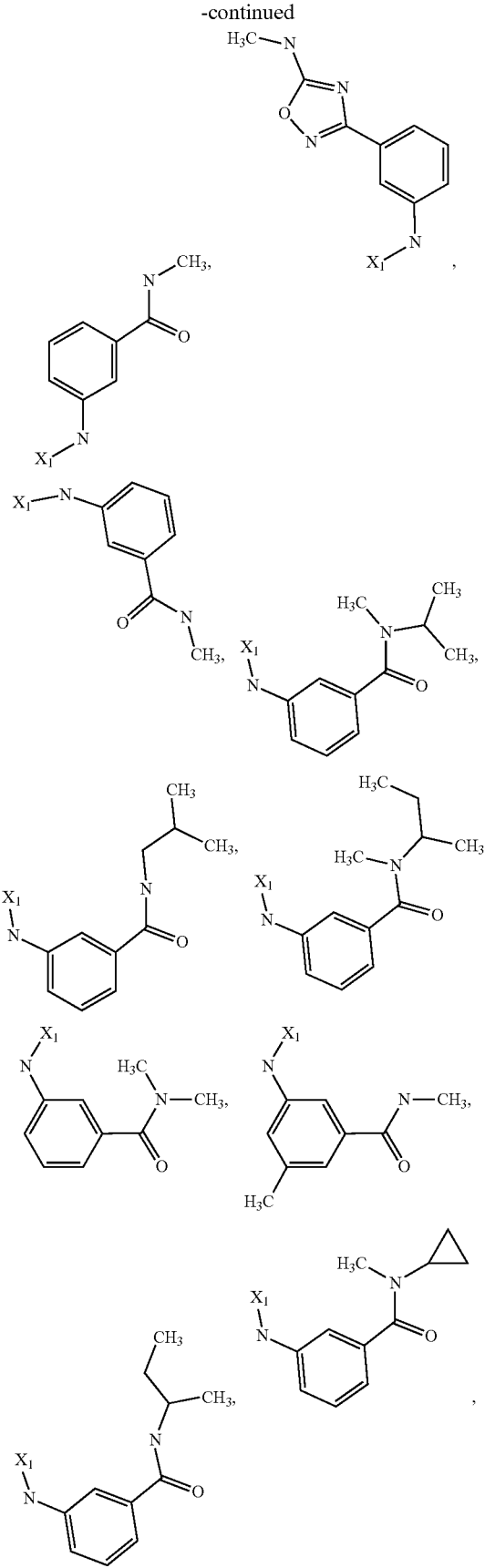
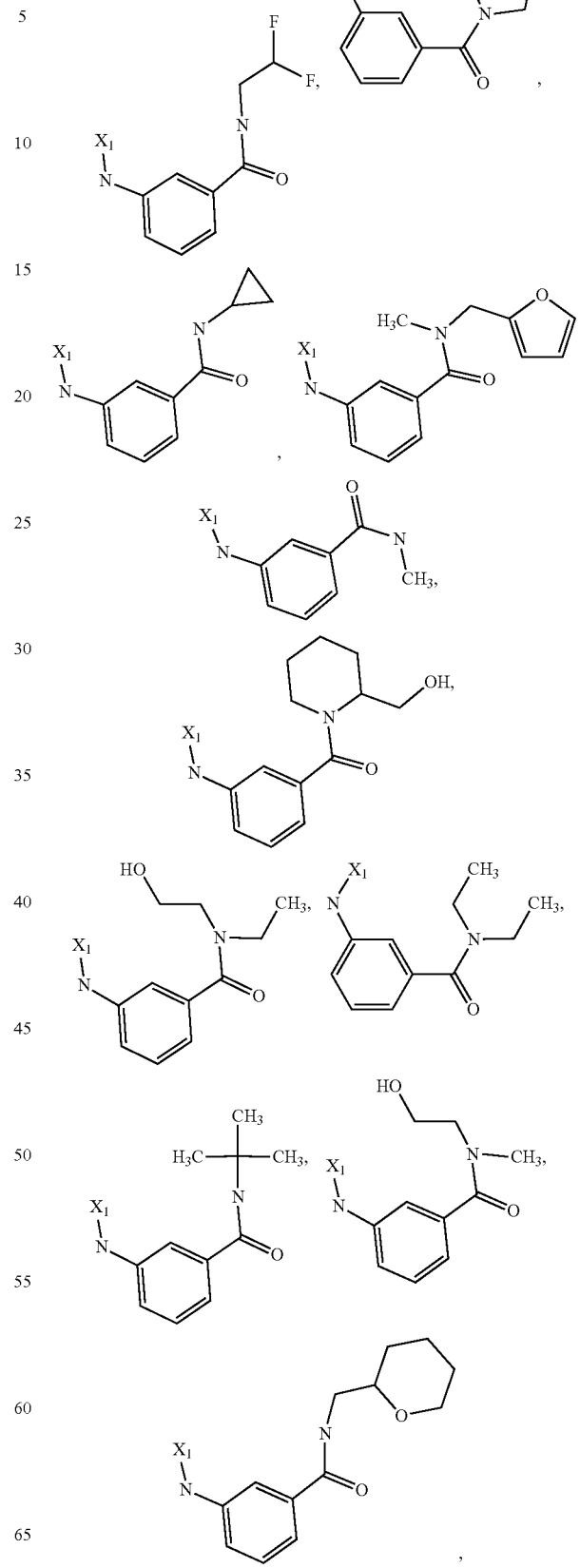

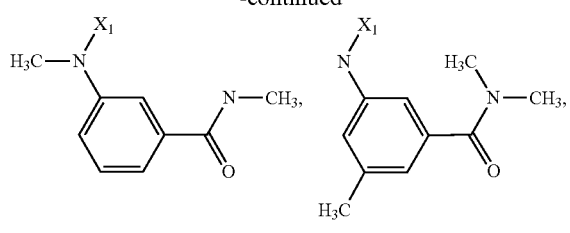
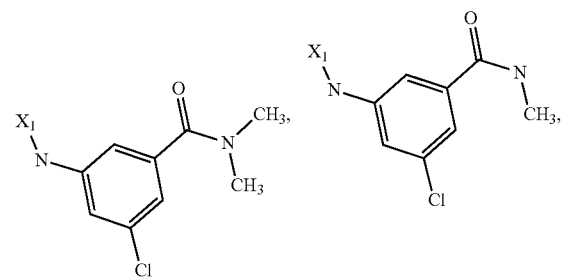
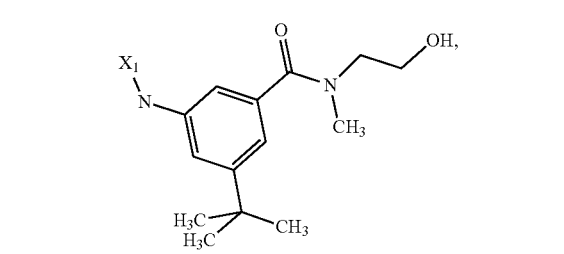
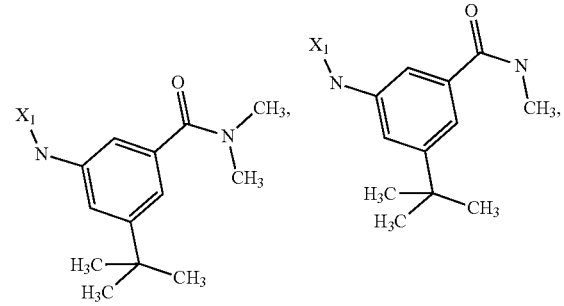
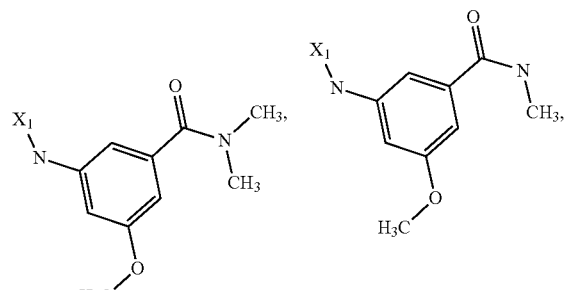
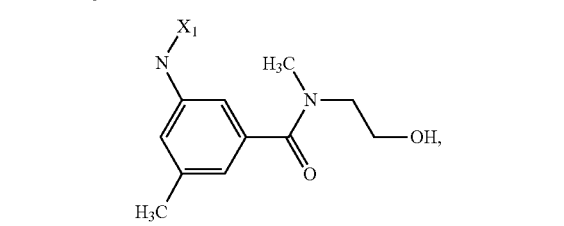
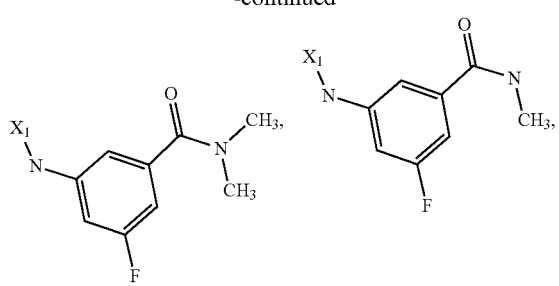
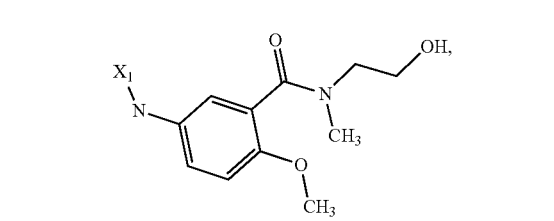
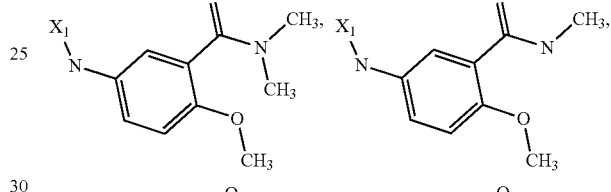
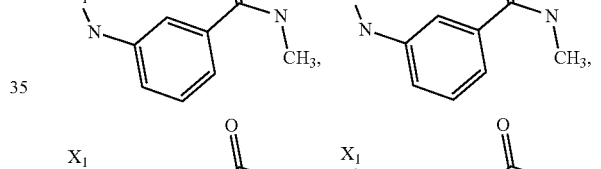
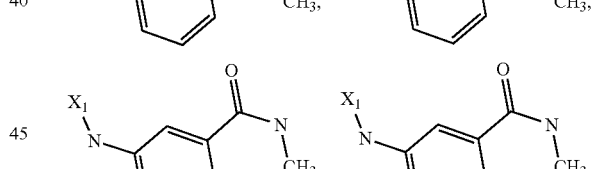
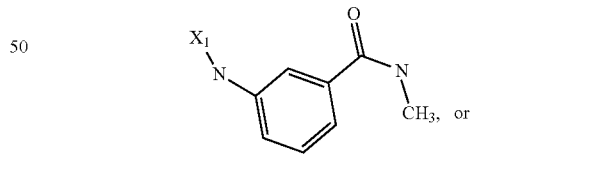
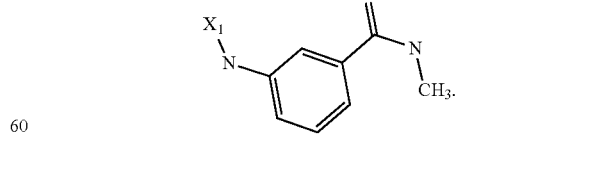
Another embodiment of the present invention further comprises administration to a subject of the compounds of formula 1, wherein A is defined as above; $R^3$ is H; $R^4$ is H; and $R^2$ is defined as in Table 1 shown below; $R^1$ is selected from

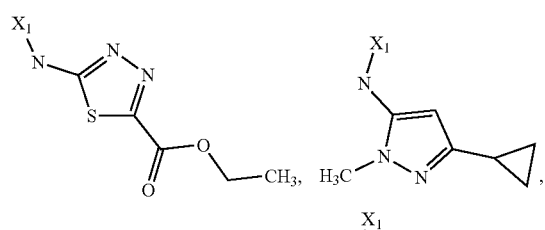
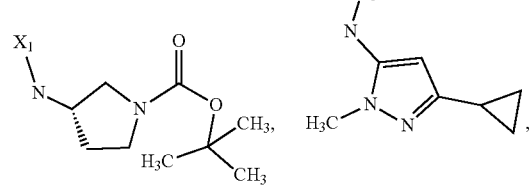
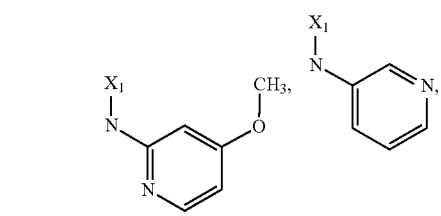
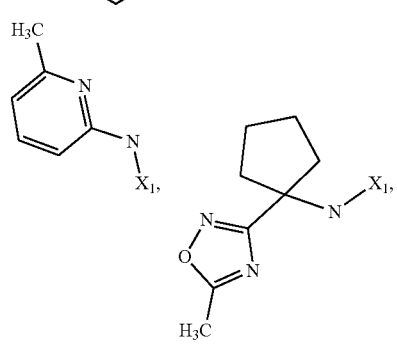
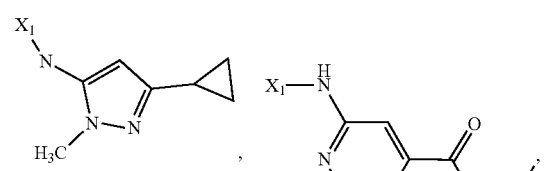
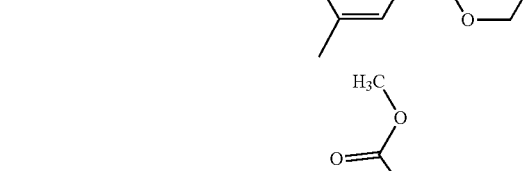
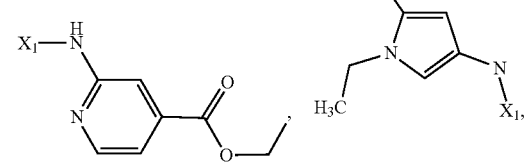
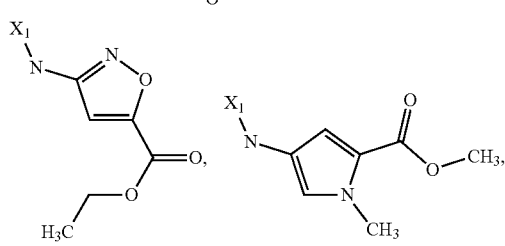
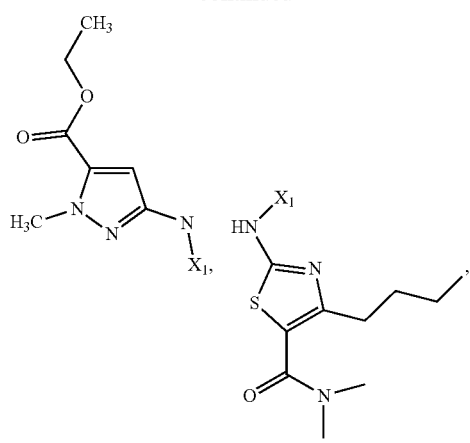
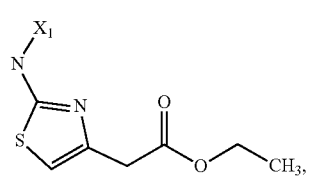
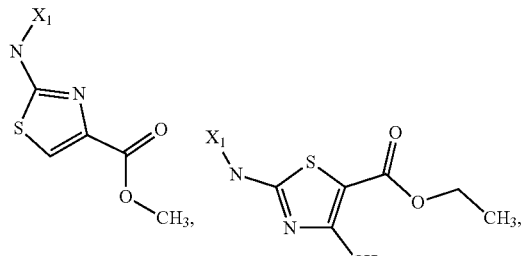
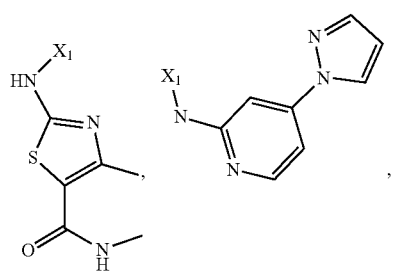
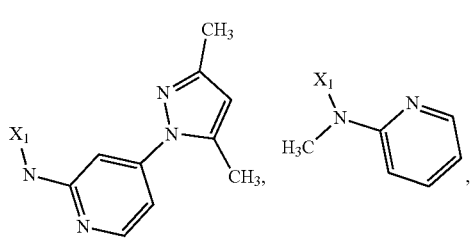

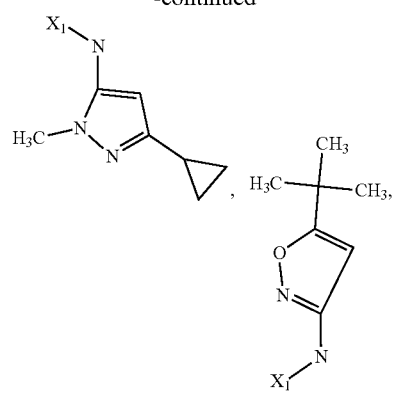
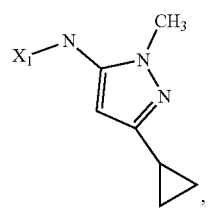
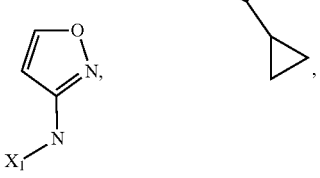
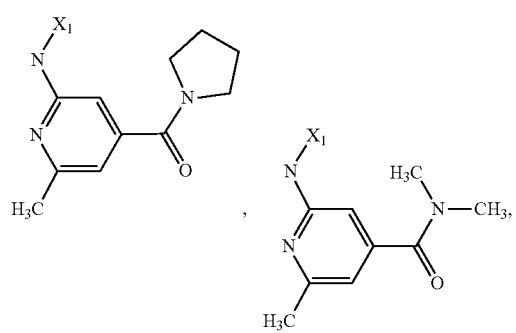
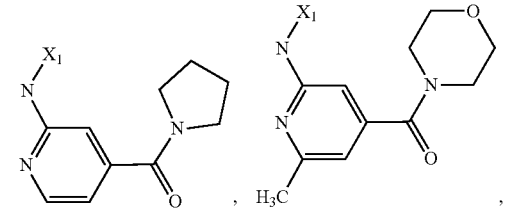
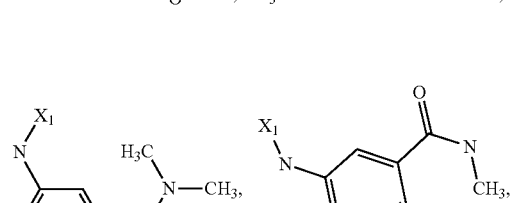
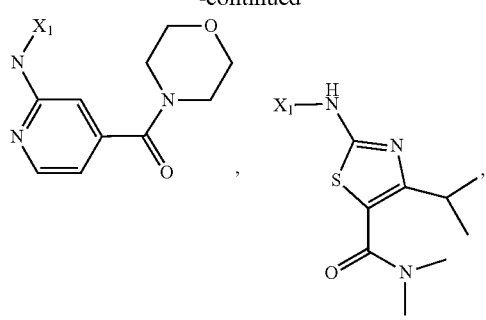
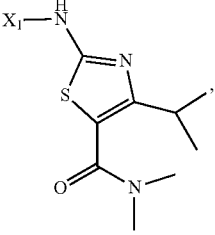
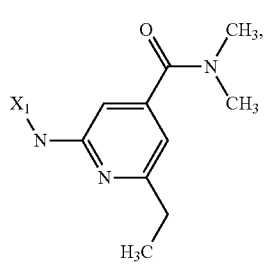

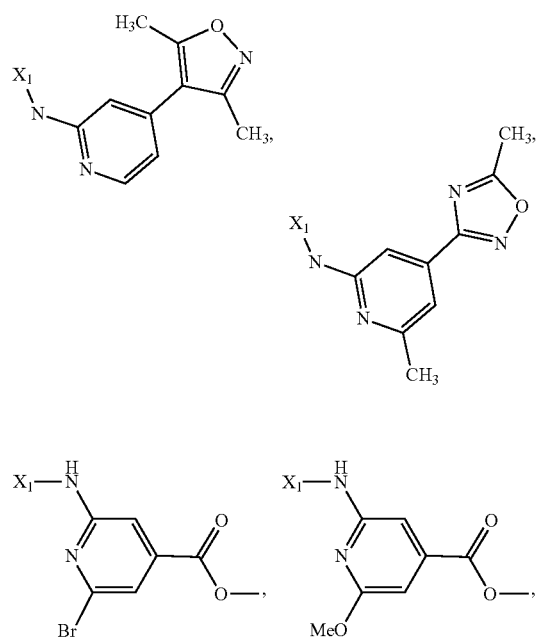
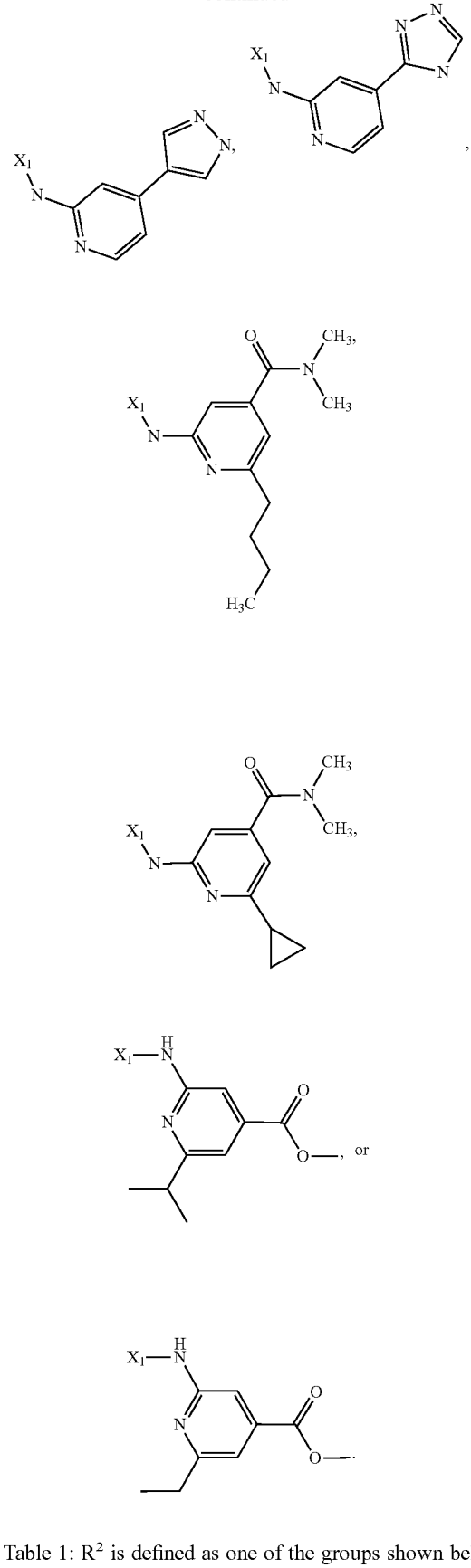
Table 1: R² is defined as one of the groups shown below in the definitions 1 to 4:

Definition 1 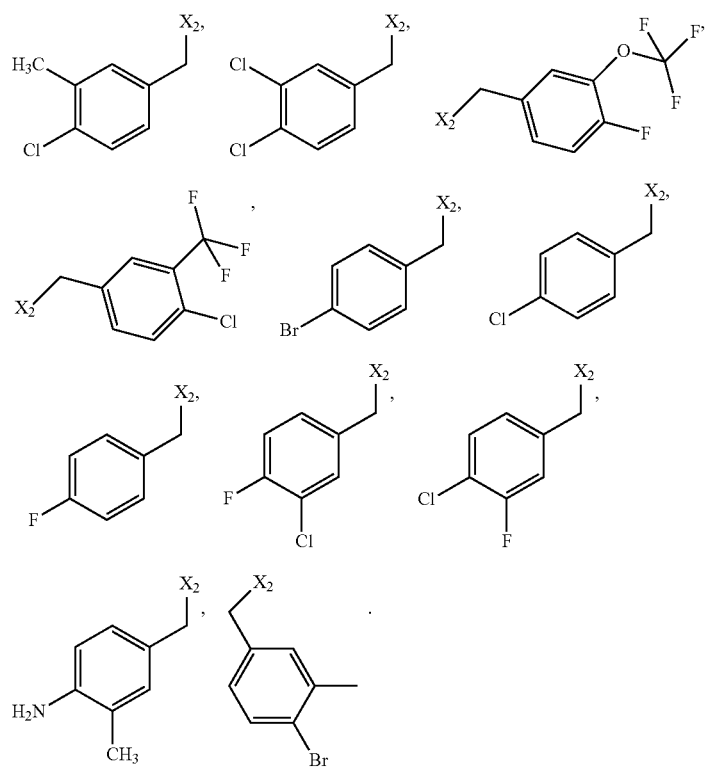
Definition 2 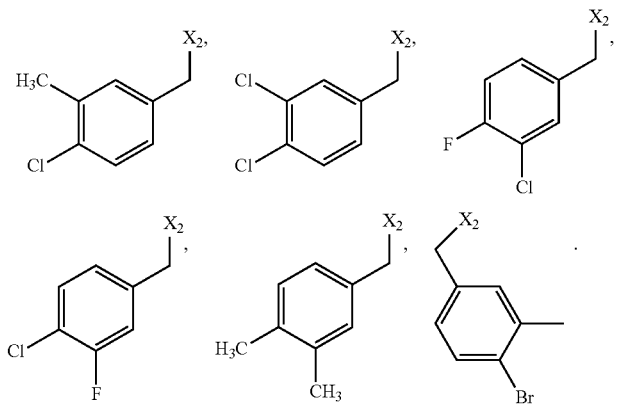
Definition 3 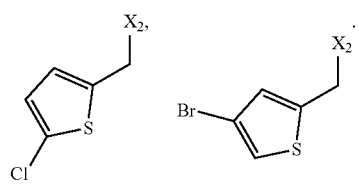
Definition 4 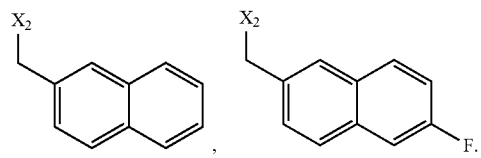

Another embodiment of the present invention further comprises administration to a subject of the compounds of formula 1, wherein the compounds of formula 1 are present in the form of the individual optical isomers, mixtures of the individual enantiomers or racemates, such as in the form of the enantiomerically pure compounds.

Another embodiment of the present invention further comprises administration to a subject of the compounds of formula 1, wherein the compounds of formula 1 are present in the form of the acid addition salts thereof with pharmacologically acceptable acids as well as optionally in the form of the solvates and/or hydrates.

b. Co-Crystals and Salts

Additional embodiments of the present invention further comprise administration to a subject of the co-crystals of the compounds of formula 2 (below). In general, for groups comprising two or more subgroups in this "Co-Crystals and Salts" section, the first named subgroup is the radical attachment point, for example, the substituent "$C_{1-3}$-alkyl-aryl" means an aryl group which is bound to a $C_{1-3}$-alkyl-group, the latter of which is bound to the core or to the group to which the substituent is attached.

Formula 2

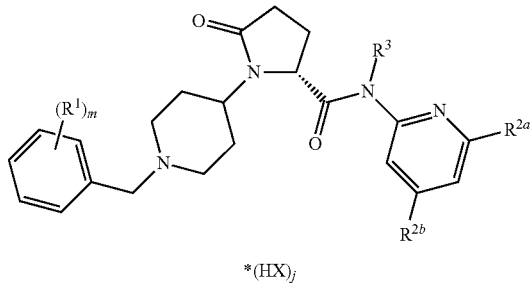

*(HX)$_j$ wherein
R$^1$ is selected from $C_{1-6}$-alkyl, $C_{1-6}$-haloalkyl, O—$C_{1-6}$-haloalkyl, halogen;
m is 1, 2 or 3, in some instances 1 or 2;
R$^{2a}$ and R$^{2b}$ are each independently selected from H, $C_{1-6}$-alkyl, $C_{1-6}$-alkenyl, $C_{1-6}$-alkynyl, $C_{3-6}$-cycloalkyl, COO—$C_{1-6}$-alkyl, O—$C_{1-6}$-alkyl, CONR$^{2b.1}$R$^{2b.2}$, halogen;
  R$^{2b.1}$ is selected from H, $C_{1-6}$-alkyl, $C_{0-4}$-alkyl-$C_{3-6}$-cycloalkyl, $C_{1-6}$-haloalkyl;
  R$^{2b.2}$ is selected from H, $C_{1-6}$-alkyl;
  or R$^{2b.1}$ and R$^{2b.2}$ are together a $C_{3-6}$-alkylene group forming with the nitrogen atom a heterocyclic ring, wherein optionally one carbon atom of the ring is replaced by an oxygen atom;
R$^3$ is selected from H, $C_{1-6}$-alkyl;
X is an anion selected from the group consisting of chloride, bromide, iodide, sulphate, phosphate, methanesulphonate, nitrate, maleate, acetate, benzoate, citrate, salicylate, fumarate, tartrate, dibenzoyltartrate, oxalate, succinate, benzoate and p-toluenesulphonate; in some instances chloride or dibenzoyltartrate;
J is 0, 0.5, 1, 1.5 or 2; in some instances 1 or 2;
with a co-crystal former selected from the group consisting of orotic acid, hippuric acid, L-pyroglutamic acid, D-pyroglutamic acid, nicotinic acid, L-(+)-ascorbic acid, saccharin, piperazine, 3-hydroxy-2-naphtoic acid, mucic (galactaric) acid, pamoic (embonic) acid, stearic acid, cholic acid, deoxycholic acid, nicotinamide, isonicotinamide, succinamide, uracil, L-lysine, L-proline, D-valine, L-arginine, glycine, in some instances ascorbic acid, mucic acid, pamoic acid, succinamide, nicotinic acid, nicotinamide, isonicotinamide, 1-lysine, or 1-proline.

Another aspect of the present invention further comprises administration to a subject of the co-crystals of the compounds of formula 2, wherein
R$^{2a}$ is selected from H, $C_{1-6}$-alkyl, $C_{1-6}$-alkenyl, $C_{1-6}$-alkynyl, $C_{3-6}$-cycloalkyl, O—$C_{1-6}$-alkyl, CONR$^{2a.1}$R$^{2a.2}$;
  R$^{2a.1}$ is selected from H, $C_{1-6}$-alkyl, $C_{1-6}$-haloalkyl;
  R$^{2a.2}$ is selected from H, $C_{1-6}$-alkyl;
R$^{2b}$ is selected from H, $C_{1-6}$-alkyl, $C_{1-6}$-alkenyl, $C_{1-6}$-alkynyl, $C_{3-6}$-cycloalkyl, COO—$C_{1-6}$-alkyl, O—$C_{1-6}$-alkyl, CONR$^{2b.1}$R$^{2b.2}$, halogen;
  R$^{2b.1}$ is selected from H, $C_{1-6}$-alkyl, $C_{0-4}$-alkyl-$C_{3-6}$-cycloalkyl, $C_{1-6}$-haloalkyl;
  R$^{2b.2}$ is selected from H, $C_{1-6}$-alkyl;
  or R$^{2b.1}$ and R$^{2b.2}$ are together a $C_{3-6}$-alkylene group forming with the nitrogen atom a heterocyclic ring, wherein optionally one carbon atom or the ring is replaced by an oxygen atom and the remaining residues are defined as above.

Another aspect of the present invention further comprises administration to a subject of the co-crystals of the compounds of formula 2, wherein
R$^{2a}$ is selected from H, $C_{1-6}$-alkyl, $C_{1-6}$-alkynyl, $C_{3-6}$-cycloalkyl, O—$C_{1-6}$-alkyl, CONR$^{2a.1}$R$^{2a.2}$;
  R$^{2a.1}$ is $C_{1-6}$-alkyl;
  R$^{2a.2}$ is H;
R$^{2b}$ is selected from H, $C_{1-6}$-alkyl, O—$C_{1-6}$-alkyl, CONR$^{2b.1}$R$^{2b.2}$;
  R$^{2b.1}$ is selected from $C_{1-6}$-alkyl, $C_{0-4}$-alkyl-$C_{3-6}$-cycloalkyl, $C_{1-6}$-haloalkyl;
  R$^{2b.2}$ is selected from H, $C_{1-6}$-alkyl;
  or R$^{2b.1}$ and R$^{2b.2}$ are together a $C_{3-6}$-alkylene group forming with the nitrogen atom a heterocyclic ring, wherein optionally one carbon atom or the ring is replaced by an oxygen atom and the remaining residues are defined as above.

Another aspect of the present invention further comprises administration to a subject of the co-crystals of the compounds of formula 2, wherein
R$^{2a}$ is selected from H, $C_{1-4}$-alkyl, $C_{1-4}$-alkynyl, $C_{3-6}$-cycloalkyl, O—$C_{1-4}$-alkyl, CONR$^{2a.1}$R$^{2a.2}$;
  R$^{2a.1}$ is $C_{1-4}$-alkyl;
  R$^{2a.2}$ is H;
R$^{2b}$ is selected from H, $C_{1-4}$-alkyl, O—$C_{1-4}$-alkyl, CONR$^{2b.1}$R$^{2b.2}$;
  R$^{2b.1}$ is selected from $C_{1-4}$-alkyl, $C_{0-4}$-alkyl-$C_{3-6}$-cycloalkyl, $C_{1-4}$-haloalkyl;
  R$^{2b.2}$ is selected from H, $C_{1-4}$-alkyl;
  or R$^{2b.1}$ and R$^{2b.2}$ are together a $C_{3-6}$-alkylene group forming with the nitrogen atom a heterocyclic ring, wherein optionally one carbon atom or the ring is replaced by an oxygen atom and the remaining residues are defined as above.

Another aspect of the present invention further comprises administration to a subject of the co-crystals of the compounds of formula 2, wherein
R$^{2a}$ is selected from H, $C_{1-4}$-alkyl,
R$^{2b}$ is selected from H, CONR$^{2b.1}$R$^{2b.2}$;
  R$^{2b.1}$ is selected from $C_{1-4}$-alkyl, $C_{0-4}$-alkyl-$C_{3-6}$-cycloalkyl, $C_{1-4}$-haloalkyl;

$R^{2b.2}$ is selected from H, $C_{1-4}$-alkyl;

or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom and the remaining residues are defined as above.

Another aspect of the present invention further comprises administration to a subject of the co-crystals of the compounds of formula 2, wherein $R^1$ is selected from $C_{1-6}$-alkyl, $C_{1-6}$-haloalkyl, O—$C_{1-6}$-haloalkyl, halogen;

m is 1 or 2;

$R^{2a}$ is selected from H, $C_{1-4}$-alkyl;

$R^{2b}$ is selected from H, $CONR^{2b.1}R^{2b.2}$;

$R^{2b.1}$ is selected from $C_{1-4}$-alkyl, $C_{0-4}$-alkyl-$C_{3-6}$-cycloalkyl, $C_{1-4}$-haloalkyl;

$R^{2b.2}$ is selected from H, $C_{1-4}$-alkyl;

or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom $R^3$ is selected from H, $C_{1-6}$-alkyl;

X is an anion selected from the group consisting of chloride or dibenzoyltartrate J is 1 or 2.

Another aspect of the present invention further comprises administration to a subject of the co-crystals of the compounds of formula 2, wherein $R^{2a}$ is selected from H, $C_{1-4}$-alkyl; in some instances Methyl, Ethyl, Propyl;

$R^{2b}$ is selected from H, $CONR^{2b.1}R^{2b.2}$;

$R^{2b.1}$ is $C_{1-4}$-alkyl; in some instances Methyl, Ethyl, Propyl;

$R^{2b.2}$ is $C_{1-4}$-alkyl; in some instances Methyl, Ethyl, Propyl;

and the remaining residues are defined as above.

Another aspect of the present invention further comprises administration to a subject of the co-crystals of the compounds of formula 2, wherein $R^{2a}$ is selected from H, $C_{1-4}$-alkyl; in some instances Methyl, Ethyl, Propyl;

$R^{2b}$ is selected from H, $CONR^{2b.1}R^{2b.2}$;

$R^{2b.1}$ is $C_{0-4}$-alkyl-$C_{3-6}$-cycloalkyl;

$R^{2b.2}$ is H, $C_{1-4}$-alkyl; in some instances H, Methyl, Ethyl, Propyl;

and the remaining residues are defined as above.

Another aspect of the present invention further comprises administration to a subject of the co-crystals of the compounds of formula 2, wherein $R^{2a}$ is selected from H, $C_{1-4}$-alkyl; in some instances Methyl, Ethyl, Propyl;

$R^{2b}$ is selected from H, $CONR^{2b.1}R^{2b.2}$;

$R^{2b.1}$ is $C_{1-4}$-haloalkyl;

$R^{2b.2}$ is selected from H, $C_{1-4}$-alky; in some instances H, Methyl, Ethyl, Propyl;

and the remaining residues are defined as above.

Another aspect of the present invention further comprises administration to a subject of the co-crystals of the compounds of formula 2, wherein $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom and the remaining residues are defined as above.

Another aspect of the present invention further comprises administration to a subject of the co-crystals of the compounds of formula 2, wherein $R^1$, m, $R^{2a}$, $R^{2b}$, $R^3$, X and j are defined as above and the co-crystal former is selected from the group consisting of ascorbic acid, mucic acid, pamoic acid, succinamide, nicotinic acid, nicotinamide, isonicotinamide, 1-lysine, 1-proline, or hydrates or hydrochlorides of the same.

Another aspect of the present invention further comprises administration to a subject of the co-crystals of the compounds of formula 2a, wherein $R^{2a}$, $R^{2b}$, $R^3$, X and j are defined as above

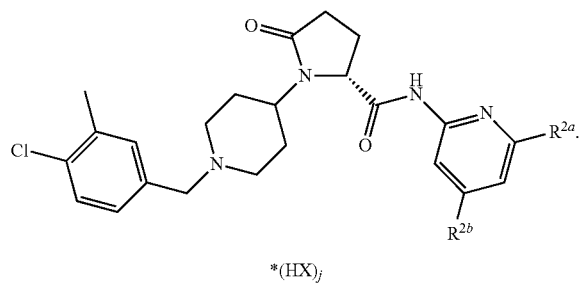

2a

*(HX)$_j$

Another aspect of the present invention further comprises administration to a subject of the co-crystals of the compounds of formula 2a, wherein $R^{2a}$ is selected from H, $C_{1-4}$-alkyl; in some instances Methyl, Ethyl, Propyl;

$R^{2b}$ is selected from H, $CONR^{2b.1}R^{2b.2}$;

$R^{2b.1}$ is $C_{1-4}$-alkyl; in some instances Methyl, Ethyl, Propyl;

$R^{2b.2}$ is $C_{1-4}$-alkyl; in some instances Methyl, Ethyl, Propyl;

and the remaining residues are defined as above.

Another aspect of the present invention further comprises administration to a subject of the co-crystals of the compounds of formula 2a, wherein $R^{2a}$ is selected from H, $C_{1-4}$-alkyl; in some instances Methyl, Ethyl, Propyl;

$R^{2b}$ is selected from H, $CONR^{2b.1}R^{2b.2}$;

$R^{2b.1}$ is $C_{0-4}$-alkyl-$C_{3-6}$-cycloalkyl;

$R^{2b.2}$ is H, $C_{1-4}$-alkyl; in some instances H, Methyl, Ethyl, Propyl;

and the remaining residues are defined as above.

Another aspect of the present invention further comprises administration to a subject of the co-crystals of the compounds of formula 2a, wherein $R^{2a}$ is selected from H, $C_{1-4}$-alkyl; in some instances Methyl, Ethyl, Propyl;

$R^{2b}$ is selected from H, $CONR^{2b.1}R^{2b.2}$;

$R^{2b.1}$ is $C_{1-4}$-haloalkyl;

$R^{2b.2}$ is selected from H, $C_{1-4}$-alky; in some instances H, Methyl, Ethyl, Propyl;

and the remaining residues are defined as above.

Another aspect of the present invention further comprises administration to a subject of the co-crystals of the compounds of formula 2a, wherein $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom, and the remaining residues are defined as above.

The free bases of compounds of formula 2 (j=0) are often amorphous and are used for a process of manufacturing co-crystal, and salts of compounds of formula 2 may be employed as desired for a process of manufacturing co-crystal. Thus, another aspect of the invention are salts of compounds of formula 2 wherein $R^1$, m, $R^{2a}$, $R^{2b}$, $R^3$ are defined as for the co-crystals above and X is an anion selected from the group consisting of chloride, bromide, iodide, sulphate, phosphate, methanesulphonate, nitrate, maleate, acetate, benzoate, citrate, salicylate, fumarate, tartrate, dibenzoyltartrate, oxalate, succinate, benzoate and p-toluenesulphonate; such as chloride, or dibenzoyltartrate; and j is 0, 0.5, 1, 1.5 or 2; such as 1 or 2.

Another aspect of the present invention further comprises administration to a subject of the co-crystals of the compounds of formula 2, wherein $R^1$, m, $R^{2a}$, $R^{2b}$, $R^3$ are defined as for the co-crystals above and X is an anion selected from the group consisting of chloride or dibenzoyltartrate;

j is 1 or 2.

Another aspect of the present invention further comprises administration to a subject of the salts of the compounds of formula 2, wherein $R^1$, m, $R^{2a}$, $R^{2b}$, $R^3$ are defined as for the salts above and X is chloride and j is 2.

Another aspect of the present invention further comprises administration to a subject of the salts of the compounds of formula 2, wherein $R^1$, m, $R^{2a}$, $R^{2b}$, $R^3$ are defined as for the salts above and X is dibenzoyltartrate and j is 1.

Another aspect of the present invention further comprises administration to a subject of the salts of the compounds of formula 2a, wherein $R^{2a}$, $R^{2b}$, $R^3$, X and j are defined as above

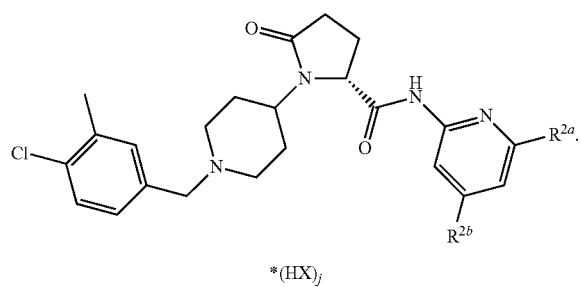

2a

*(HX)$_j$

Another aspect of the present invention further comprises administration to a subject of the salts of the compounds of formula 2a, wherein $R^{2a}$ is selected from H, $C_{1-4}$-alkyl; in some instances Methyl, Ethyl, Propyl;

$R^{2b}$ is selected from H, $CONR^{2b.1}R^{2b.2}$;

$R^{2b.1}$ is $C_{1-4}$-alkyl; in some instances Methyl, Ethyl, Propyl;

$R^{2b.2}$ is $C_{1-4}$-alkyl; in some instances Methyl, Ethyl, Propyl;

and the remaining residues are defined as above.

Another aspect of the present invention further comprises administration to a subject of the salts of the compounds of formula 2a, wherein $R^{2a}$ is selected from H, $C_{1-4}$-alkyl; in some instances Methyl, Ethyl, Propyl;

$R^{2b}$ is selected from H, $CONR^{2b.1}R^{2b.2}$;

$R^{2b.1}$ is $C_{0-4}$-alkyl-$C_{3-6}$-cycloalkyl;

$R^{2b.2}$ is H, $C_{1-4}$-alkyl; in some instances H, Methyl, Ethyl, Propyl;

and the remaining residues are defined as above.

Another aspect of the present invention further comprises administration to a subject of the salts of the compounds of formula 2a, wherein $R^{2a}$ is selected from H, $C_{1-4}$-alkyl; in some instances Methyl, Ethyl, Propyl;

$R^{2b}$ is selected from H, $CONR^{2b.1}R^{2b.2}$;

$R^{2b.1}$ is $C_{1-4}$-haloalkyl;

$R^{2b.2}$ is H, $C_{1-4}$-alky; in some instances H, Methyl, Ethyl, Propyl; and the remaining residues are defined as above.

Another aspect of the present invention further comprises administration to a subject of the salts of the compounds of formula 2a, wherein $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom and the remaining residues are defined as above.

Another aspect of the present invention further comprises administration to a subject of the salts of the compounds of formula 2a, wherein $R^1$, m, $R^{2a}$, $R^{2b}$, $R^3$ are defined as for the salts above and X is chloride and j is 2.

Another aspect of the present invention further comprises administration to a subject of the salts of the compounds of formula 2a, wherein $R^1$, m, $R^{2a}$, $R^{2b}$, $R^3$ are defined as for the salts above and X is dibenzoyltartrate and j is 1. Another aspect of the invention are salts of compounds of formula 2a, wherein $R^1$, m, $R^{2a}$, $R^{2b}$, $R^3$ are defined as for the salts above and X is (S)—(S)-(+)-2,3-dibenzoyl-tartrate and j is 1.

c. Formulations

Additional embodiments of the present invention further comprise administration to a subject of a pharmaceutical composition containing compounds of formula 3

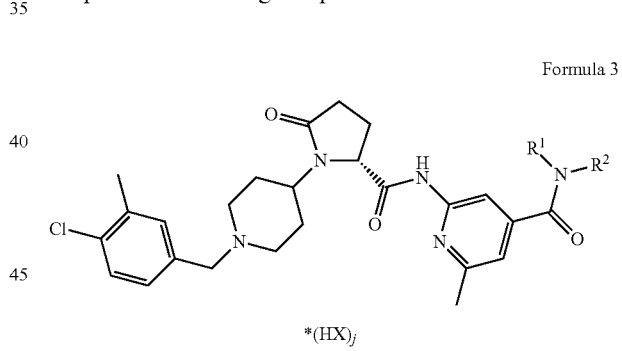

Formula 3

*(HX)$_j$ wherein $R^1$ is selected from H, $C_{1-6}$-alkyl, $C_{0-4}$-alkyl-$C_{3-6}$-cycloalkyl, $C_{1-6}$-haloalkyl;

$R^2$ is selected from H, $C_{1-6}$-alkyl;

X is an anion selected from the group consisting of chloride or ½ dibenzoyltartrate j is 1 or 2.

An embodiment of the present invention further comprises administration to a subject of a pharmaceutical composition containing compounds of formula 3 wherein $R^1$ is selected from H, $C_{1-6}$-alkyl;

$R^2$ is selected from H, $C_{1-6}$-alkyl;

X is an anion selected from the group consisting of chloride or ½ dibenzoyltartrate j is 1 or 2.

An embodiment of the present invention further comprises administration to a subject of a pharmaceutical composition containing compounds of formula 3 wherein R[1] is selected from H, Methyl, Ethyl, Propyl, Butyl;
R[2] is selected from H, Methyl, Ethyl, Propyl, Butyl;
X is an anion selected from the group consisting of chloride or ½ dibenzoyltartrate, such as chloride;
j is 1 or 2, in some instances 2.

An embodiment of the present invention further comprises administration to a subject of a pharmaceutical composition containing compounds of formula 3 wherein
R[1] is selected from H, Methyl, Ethyl, Propyl, Butyl;
R[2] is selected from H, Methyl;
X is an anion selected from the group consisting of chloride or ½ dibenzoyltartrate, such as chloride;
j is 1 or 2, in some instances 2.

An embodiment of the present invention further comprises administration to a subject of a pharmaceutical composition containing compounds of formula 3 wherein
R[1] is selected from H, Methyl;
R[2] is selected from H, Methyl;
X is an anion selected from the group consisting of chloride or ½ dibenzoyltartrate, such as chloride;
j is 1 or 2, in some instances 2.

An embodiment of the present invention further comprises administration to a subject of a pharmaceutical composition containing compounds described in Table 2 as a hydrochloride. An embodiment of the present invention further comprises administration to a subject of a pharmaceutical composition containing compounds described in Table 2 as a di-hydrochloride.

TABLE 2

| # | Structure |
|---|---|
| 1 | 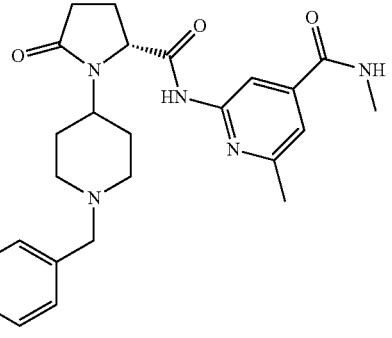 |
| 2 | 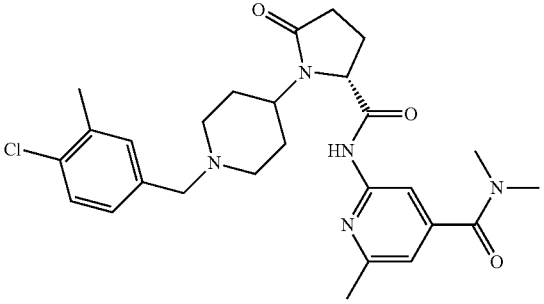 [SMILES: Cc1cc(C(=O)N(C)C)cc(NC(=O)[C@H]2CCC(=O)N2C2CCN(Cc3ccc(Cl)c(C)c3)CC2)n1] |
| 3 | 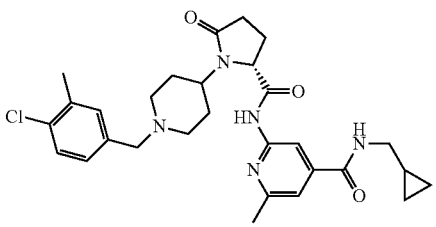 [SMILES: Cc1cc(C(=O)NCC2CC2)cc(NC(=O)[C@H]2CCC(=O)N2C2CCN(Cc3ccc(Cl)c(C)c3)CC2)n1] |

TABLE 2-continued

| # | Structure |
|---|---|
| 4 | 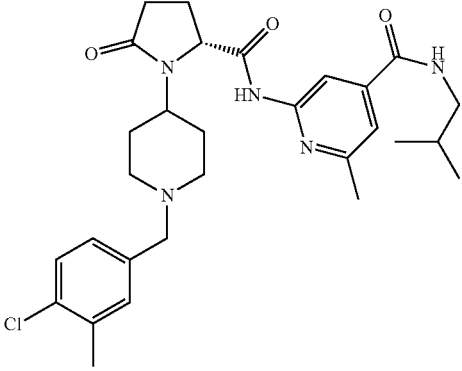 [SMILES: Cc1cc(C(=O)NCC(C)C)cc(NC(=O)[C@H]2CCC(=O)N2C2CCN(Cc3ccc(Cl)c(C)c3)CC2)n1] |
| 5 | 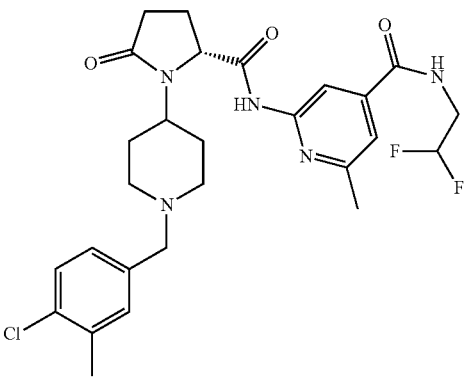 [SMILES: Cc1cc(C(=O)NCC(F)F)cc(NC(=O)[C@H]2CCC(=O)N2C2CCN(Cc3ccc(Cl)c(C)c3)CC2)n1] |
| 6 | 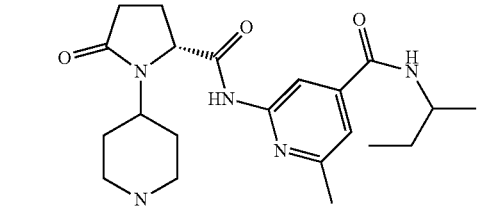 |
| 7 | 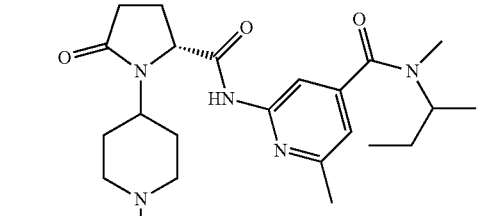 |

TABLE 2-continued

| # | Structure |
|---|---|
| 8 | (structure) |
| 9 | (structure) |
| 10 | (structure) |

Another aspect of the present invention is administration to a subject of a pharmaceutical dosage form of the compounds described above, wherein the dosage is an orally deliverable dosage form.

Another aspect of the present invention is administration to a subject of a pharmaceutical dosage form of the compounds described above, which is in the form of a tablet, capsule, pellets, powder or granules.

Another aspect of the present invention is administration to a subject of the pharmaceutical dosage forms described above for use as medicament.

Another aspect of the present invention is the use of the above pharmaceutical dosage forms for the preparation of a medicament for the treatment of a retina-associated disease or condition selected from dry age-related macular degeneration, wet age-related macular degeneration, central retinal vein occlusion, retinopathy of prematurity, and diabetic retinopathy.

Another aspect of the present invention is a method for the treatment and/or prevention of a disease or condition selected from retinal-associated disease such as dry age-related macular degeneration, wet age-related macular degeneration, central retinal vein occlusion, retinopathy of prematurity, and diabetic retinopathy, characterized in that an effective amount of the above defined pharmaceutical dosage form is administered orally to a subject or patient once, twice, thrice or several times daily.

The invention further provides a method of improving visual acuity in a subject in need thereof, the method comprising administering to the subject an effective amount of the compound described herein. Optionally, the subject suffers from a retinal-associated disease, such as the retinal-associated diseases described herein. Use of the compound described herein in the preparation of a medicament also is contemplated, as is use of the compound to improve visual acuity.

d. Dosage Forms/Ingredients

Solid pharmaceutical compositions ready for use/ingestion made from a compound of formula 3 comprise, for example, powders, granules, pellets, tablets, capsules, chewable tablets, dispersible tables, troches and lozenges.

Capsule formulations according to the invention comprise the powdery intermediate of a compound of formula 3, an intermediate blend comprising the powdery intermediate, pellets or granules obtained by conventional wet-, dry or hot-melt granulation or hot-melt extrusion or spray-drying of a suitable intermediate blend, filled in conventional capsules, e.g. hard gelatin or HPMC capsules.

The Capsule formulations from above may also comprise the powdery intermediate of a compound of formula 3 in a compacted form.

Capsule formulations according to the invention also may comprise the compound of formula 3 suspended or diluted in a liquid or mixture of liquids.

Tablet formulations according to the invention comprise such tablets obtained by, e.g., direct compression of a suitable final blend or by tableting of pellets or granules obtained by conventional wet-, dry or hot-melt granulation or hot-melt extrusion or spray-drying of a suitable intermediate blend.

Another aspect of the present invention is a dosage form where a pH-adjusting or buffering agent is added for stability improvement of the active ingredient. The pH-adjusting/buffering agent may be a basic amino acid, which has an amino group and alkaline characteristics (isoelectric point, pI: 7.59-10.76), such as, e.g., L-arginine, L-lysine or L-histidine. A buffering agent within the meaning of this invention is L-arginine. L-arginine has a particular suitable stabilizing effect on the compositions of this invention, e.g., by suppressing chemical degradation of compounds of formula 3.

Thus, in an embodiment, the present invention is directed to a pharmaceutical composition (e.g. an oral solid dosage form, particularly a tablet) comprising a compound of formula 3 and L-arginine for stabilizing the composition, particularly against chemical degradation; as well as one or more pharmaceutical excipients.

Suitably the pharmaceutical excipients used within this invention are conventional materials such as cellulose and its derivates, D-mannitol, corn starch, pregelatinized starch as a filler, copovidone as a binder, crospovidone as disintegrant, magnesium stearate as a lubricant, colloidal anhydrous silica as a glidant, hypromellose as a film-coating agent, polyethylene glycol as a plasticizer, titanium dioxide, iron oxide red/yellow as a pigment, and talc, etc.

Pharmaceutical excipients can be a first and second diluent, a binder, a disintegrant and a lubricant; an additional disintegrant and an additional glidant are a further option.

Diluents suitable for a pharmaceutical composition according to the invention are, for example, cellulose powder, microcrystalline cellulose, lactose in various crystalline modifications, dibasic calcium phosphate anhydrous, dibasic calcium phosphate dihydrate, erythritol, low substituted hydroxypropyl cellulose, mannitol, starch or modified starch (e.g. pregelatinized or partially hydrolysed) or xylitol.

Among those diluents mannitol and microcrystalline cellulose are employed in some instances.

Diluents that may be employed in some instances as the second diluent are the above mentioned diluents mannitol and microcrystalline cellulose.

Lubricants suitable for a pharmaceutical composition according to the invention are, for example, talc, polyethyleneglycol, calcium behenate, calcium stearate, sodium stearylfumarate, hydrogenated castor oil or magnesium stearate, where in some instances magnesium stearate is employed.

Binders suitable for a pharmaceutical composition according to the invention include, but are not limited to, copovidone (copolymerisates of vinylpyrrolidon with other vinylderivates), hydroxypropyl methylcellulose (HPMC), hydroxypropylcellulose (HPC), polyvinylpyrrolidon (povidone), pregelatinized starch, stearic-palmitic acid, low-substituted hydroxypropylcellulose (L-HPC), copovidone and pregelatinized starch being employed in some instances. The above mentioned binders pregelatinized starch and L-HPC show additional diluent and disintegrant properties and can also be used as the second diluent or the disintegrant.

Disintegrants suitable for a pharmaceutical composition according to the present invention are, e.g., corn starch, crospovidone, polacrilin potassium, croscarmellose sodium, low-substituted hydroxypropylcellulose (L-HPC) or pregelatinized starch, such as croscarmellose sodium.

As an optional glidant colloidal silicon dioxide can be used.

An exemplary composition according to the present invention comprises the diluent mannitol, microcrystalline cellulose as a diluent with additional disintegrating properties, the binder copovidone, the disintegrant croscarmellose sodium, and magnesium stearate as the lubricant.

Typical pharmaceutical compositions comprise (% by weight):
10-50% active ingredient
20-88% diluent 1,
5-50% diluent 2,
1-5% binder,
1-15% disintegrant, and
0.1-5% lubricant.

Pharmaceutical compositions according to some embodiments comprise (% by weight):
10-50% active ingredient
20-75% diluent 1,
5-30% diluent 2,
2-30% binder,
1-12% disintegrant, and
0.1-3% lubricant Pharmaceutical compositions according to some embodiments comprise (% by weight):
10-90% active ingredient
5-70% diluent 1,
5-30% diluent 2,
0-30% binder,
1-12% disintegrant, and
0.1-3% lubricant.

Pharmaceutical compositions according to some embodiments comprise (% by weight):
10-50% active ingredient
20-75% diluent 1,
5-30% diluent 2,
2-30% binder,
0.5-20% buffering agent,
1-12% disintegrant, and
0.1-3% lubricant Pharmaceutical compositions according to some embodiments comprise (% by weight):
30-70% active ingredient
20-75% diluent 1,
5-30% diluent 2,
2-30% binder,
0.5-20% buffering agent,
1-12% disintegrant, and
0.1-3% lubricant.

Pharmaceutical compositions containing 10-90% of active ingredient, preferably 30-70% active ingredient (% by weight) are employed in some instances.

A tablet formulation according to the invention may be uncoated or coated, e.g., film-coated, using suitable coatings known not to negatively affect the dissolution properties of the final formulation. For instance the tablets can be provided with a seal coat for protection of the patients environment and clinical staff as well as for moisture protection purposes by dissolving a high molecular weight polymer as polyvinylpyrrolidone or hydroxypropyl-methylcellulose together with plasticizers, lubricants and optionally pigments and tensides in water or organic solvent as acetone and spraying this mixture on the tablet cores inside a coating equipment as a pan coater or a fluidized bed coater with wurster insert.

Additionally, agents such as beeswax, shellac, cellulose acetate phthalate, polyvinyl acetate phthalate, zein, film forming polymers such as hydroxypropyl cellulose, ethylcellulose and polymeric methacrylates can be applied to the tablets, provided that the coating has no substantial effect on the disintegration/dissolution of the dosage form and that the coated dosage form is not affected in its stability.

After the dosage form is film-coated, a sugar coating may be applied onto the sealed pharmaceutical dosage form. The sugar coating may comprise sucrose, dextrose, sorbitol and the like or mixtures thereof. If desired, colorants or opacifiers may be added to the sugar solution.

Solid formulations of the present invention tend to be hygroscopic. They may be packaged using PVC-blisters, PVDC-blisters or a moisture-proof packaging material such as aluminum foil blister packs, alu/alu blister, transparent or opaque polymer blister with pouch, polypropylene tubes, glass bottles and HDPE bottles optionally containing a child-resistant feature or may be tamper evident. The primary packaging material may comprise a desiccant such as molecular sieve or silica gel to improve chemical stability of the API. Opaque packaging such as colored blister materials, tubes, brown glass bottles or the like can be used to prolong shelf life of the API by reduction of photo degradation.

e. Dosages

A dosage range of the compound of formula 3 is usually between 100 and 1000 mg, in particular between 200 and 900 mg, 300 and 900 mg, or 350 and 850 mg, or 390 and 810 mg. It is possible to give one or two tablets, and in some instances two tablets are employed for a daily oral dosage of 100, 200, 300, 350, 400, 450, 500, 550, 600, 650, 700, 750, 800, 850, or 900 mg, such as 350, 400, 450, 750, 800, or 850 mg.

The dosages range can be achieved by one tablet or by two tablets; e.g., where two tablets are administered, each containing half of the dosage.

The application of the active ingredient may occur up to three times a day, such as one or two times a day. Particular dosage strengths are 400 mg or 800 mg.

f. Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The term "about" means 5% more or less of the specified value. Thus, about 100 minutes could also be read as from 95 to 105 minutes.

Where a compound of the present invention is depicted in form of a chemical name and as a formula, in case of any discrepancy, the formula shall prevail. An asterisk is may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof, as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Of interest are groups that have no negative effect on the pharmacological efficacy of the compounds. For example the groups may comprise:
- straight-chain or branched carbon chains, optionally interrupted by heteroatoms, optionally substituted by rings, heteroatoms or other common functional groups;
- aromatic or non-aromatic ring systems consisting of carbon atoms and optionally heteroatoms, which may in turn be substituted by functional groups; or
- a number of aromatic or non-aromatic ring systems consisting of carbon atoms and optionally heteroatoms which may be linked by one or more carbon chains, optionally interrupted by heteroatoms, optionally substituted by heteroatoms or other common functional groups.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley—VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N, N-dibenzylphenethylamine, 1-ephenamine, and N,P-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

By the term heterocyclic rings ("het") are meant five-, six- or seven-membered, saturated or unsaturated heterocyclic rings or 5-10 membered, bicyclic hetero rings which may contain one, two or three heteroatoms, selected from among oxygen, sulphur and nitrogen; the ring may be linked to the molecule by a carbon atom or, if present, by a nitrogen atom. The following are examples of five-, six- or seven-membered, saturated or unsaturated heterocyclic rings:

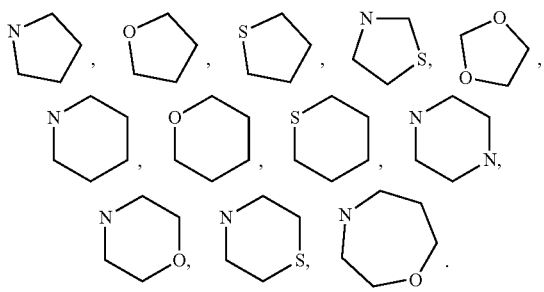

Unless stated otherwise, a heterocyclic ring may be provided with a keto group. Examples include:

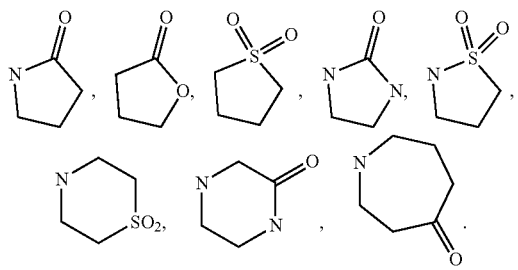

Examples of 5-10-membered bicyclic hetero rings are pyrrolizine, indole, indolizine, isoindole, indazole, purine, quinoline, isoquinoline, benzimidazole, benzofurane, benzopyrane, benzothiazole, benzoisothiazole, pyridopyrimidine, pteridine, pyrimidopyrimidine,

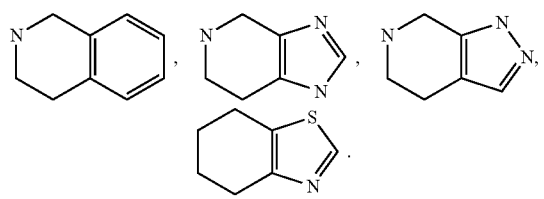

Although the term heterocyclic rings includes heterocyclic aromatic groups, the term heterocyclic aromatic groups ("hetaryl") denotes five- or six-membered heterocyclic aromatic groups or 5-10 membered, bicyclic hetaryl rings which may contain one, two or three heteroatoms, selected from among oxygen, sulphur and nitrogen, which contain sufficient conjugated double bonds that an aromatic system is formed. The ring may be linked to the molecule through a carbon atom or if present through a nitrogen atom. The following are examples of five- or six-membered heterocyclic aromatic groups:

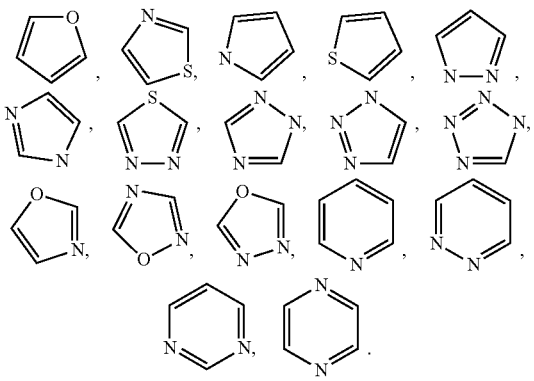

Examples of 5-10-membered bicyclic hetaryl rings include pyrrolizine, indole, indolizine, isoindole, indazole, purine, quinoline, isoquinoline, benzimidazole, benzofuran, benzopyrane, benzothiazole, benzoisothiazole, pyridopyrimidine, pteridine, pyrimidopyrimidine.

The term "halogen" as used herein means a halogen substituent selected from fluoro, chloro, bromo or iodo.

By the term "$C_{1-6}$-alkyl" (including those which are part of other groups) are meant branched and unbranched alkyl groups with 1 to 6 carbon atoms, and by the term "$C_{1-4}$-alkyl" are meant branched and unbranched alkyl groups with 1 to 4 carbon atoms. Alkyl groups with 1 to 4 carbon atoms are present in some instances. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc. may optionally also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are present in some instances. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene also include all the possible isomeric forms of the relevant groups with the same number of carbons. Thus for example propyl also includes 1-methylethylene and butylene includes 1-methylpropylene, 1,1-dimethylethylene, 1,2-dimethylethylene.

The term "$C_{2-6}$-alkenyl" (including those which are part of other groups) denotes branched and unbranched alkenyl groups with 2 to 6 carbon atoms and the term "$C_{2-4}$-alkenyl" denotes branched and unbranched alkenyl groups with 2 to 4 carbon atoms, provided that they have at least one double bond. Of interest in some embodiments are alkenyl groups with 2 to 4 carbon atoms. Examples include: ethenyl or vinyl, propenyl, butenyl, pentenyl, or hexenyl. Unless otherwise stated, the definitions propenyl, butenyl, pentenyl and hexenyl include all possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are present in some instances. Examples include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the respective groups with the same number of carbons. Thus, for example, propenyl also includes 1-methylethenylene and butenylene includes 1-methylpropenylene, 1,1-dimethylethenylene, 1,2-dimethylethenylene.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are present in some instances. Examples include: ethynyl, propynyl, butynyl, pentynyl, or hexynyl. Unless stated otherwise, the definitions propynyl, butynyl, pentynyl and hexynyl include all the possible isomeric forms of the respective groups. Thus, for example, propynyl includes 1-propynyl and 2-propynyl, butynyl includes 1-, 2- and 3-butynyl, 1-methyl-1-propynyl, 1-methyl-2-propynyl etc.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Alkynylene groups with 2 to 4 carbon atoms are present in some instances. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene or hexynylene. Unless stated otherwise, the definitions propynylene, butynylene, pentynylene and hexynylene include all the possible isomeric forms of the respective groups with the same number of carbons. Thus for example propynyl also includes 1-methylethynylene and butynylene includes 1-methylpropynylene, 1,1-dimethylethynylene, 1,2-dimethylethynylene.

The term "$C_{3-6}$-cycloalkyl" (including those which are part of other groups) as used herein means cyclic alkyl groups with 3 to 8 carbon atoms, of interest in certain embodiments are cyclic alkyl groups with 5 to 6 carbon atoms. Examples include: cyclopropyl, cyclobutyl, cyclopentyl or cyclohexyl.

By the term "$C_{1-6}$-haloalkyl" (including those which are part of other groups) are meant branched and unbranched alkyl groups with 1 to 6 carbon atoms wherein one or more hydrogen atoms are replaced by a halogen atom selected from among fluorine, chlorine or bromine, such as fluorine and chlorine, where in some instances the halogen atom is fluorine. By the term "$C_{1-4}$-haloalkyl" are meant correspondingly branched and unbranched alkyl groups with 1 to 4 carbon atoms, wherein one or more hydrogen atoms are replaced analogously to what was stated above. $C_{1-4}$-haloalkyl is present in some instances. Examples include: $CH_2F$, $CHF_2$, $CF_3$.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-haloalkyl", wherein n is an integer from 2 to n, either alone or in combination with another radical denotes an acyclic, saturated, branched or linear hydrocarbon radical with 1 to n C atoms wherein one or more hydrogen atoms are replaced by a halogen atom selected from among fluorine, chlorine or bromine, such as fluorine and chlorine, where in some instances the halogen is fluorine. Examples include: $CH_2F$, $CHF_2$, $CF_3$.

The term "$C_{1-n}$-alkylene" wherein n is an integer 2 to n, either alone or in combination with another radical, denotes an acyclic, straight or branched chain divalent alkyl radical containing from 1 to n carbon atoms. For example the term $C_{1-4}$-alkylene includes —$CH_2$—, —$CH_2$—$CH_2$—, —$CH(CH_3)$—, —$CH_2$—$CH_2$—$CH_2$—, —$C(CH_3)_2$—, —$CH(CH_2CH_3)$—, —$CH(CH_3)$—$CH_2$—, —$CH_2$—$CH(CH_3)$—, —$CH_2$—$CH_2$—$CH_2$—$CH_2$—, —$CH_2$—$CH_2$—$CH(CH_3)$—, —$CH(CH_3)$—$CH_2$—$CH_2$—, —$CH_2$—$CH(CH_3)$—$CH_2$—, —$CH_2$—$C(CH_3)_2$—, —$C(CH_3)_2$—$CH_2$—, —$CH(CH_3)$—$CH(CH_3)$—, —$CH_2$—$CH(CH_2CH_3)$—, —$CH(CH_2CH_3)$—$CH_2$—, —$CH(CH_2CH_2CH_3)$—, —$CH(CH(CH_3))_2$— and —$C(CH_3)(CH_2CH_3)$—.

The term "$C_2$-n-alkenyl", is used for a group as defined in the definition for "$C_{1-n}$-alkyl" with at least two carbon atoms, if at least two of those carbon atoms of said group are bonded to each other by a double bond.

The term "$C_2$-n-alkynyl", is used for a group as defined in the definition for "$C_{1-n}$-alkyl" with at least two carbon atoms, if at least two of those carbon atoms of said group are bonded to each other by a triple bond.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

g. Combinations

The compounds of general formula 1 may be used on their own or combined with other active substances of formula 1 according to the invention. The compounds of general formula 1 may optionally also be combined with other pharmacologically active substances. These include, ß2-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-1B signaling pathway as for example IKK2 kinase inhibitors, iNOS inhibitors, MRP4 inhibitors, leukotriene biosynthesis inhibitors as for example 5-Lipoxygenase (5-LO) inhibitors, cPLA2 inhibitors, Leukotriene A4 Hydrolase inhibitors or FLAP inhibitors, Non-steroidal anti-inflammatory agents (NSAIDs), CRTH2 antagonists, DP1-receptor modulators, Thromboxane receptor antagonists, CCR3 antagonists, $CCR^4$ antagonists, $CCR^1$ antagonists, CCR5 antagonists, CCR6 antagonists, CCR7 antagonists, CCR8 antagonists, CCR9 antagonists, CCR30 antagonists, $CXCR^3$ antagonists, $CXCR^4$ antagonists, $CXCR^2$ antagonists, $CXCR^1$ antagonists, CXCR5 antagonists, CXCR6 antagonists, $CX3CR^3$ antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic receptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, VEGF inhibitors, but also combinations of two or three active substances.

Also contemplated are betamimetics, anticholinergics, corticosteroids, PDE4-inhibitors, LTD4-antagonists, EGFR-inhibitors, CRTH2 inhibitors, 5-LO-inhibitors, Histamine receptor antagonists and SYK-inhibitors, but also combinations of two or three active substances, e.g., betamimetics with corticosteroids, PDE4-inhibitors, CRTH2-inhibitors or LTD4-antagonists; anticholinergics with betamimetics, corticosteroids, PDE4-inhibitors, CRTH2-inhibitors or LTD4-antagonists, corticosteroids with PDE4-inhibitors, CRTH2-inhibitors or LTD4-antagonists; PDE4-inhibitors with CRTH2-inhibitors or LTD4-antagonists; and CRTH2-inhibitors with LTD4-antagonists.

Also contemplated by the invention is combination treatment of the indications disclosed herein using the compounds of general formula 1 plus an anti-VEGF therapy (e.g., one or more VEGF modulators and inhibitors). In various aspects, the method comprises improving visual acuity by administering a compound of formula 1 and further administering an anti-VEGF therapy that reduces the biological effect of VEGF at the target site. VEGF modulators/inhibitors include, but are not limited to, antibody and small molecule VEGF-A inhibitors such as ranibizumab, bevacizumab, and aflibercept, which are listed by way of example and not limitation. Anti-VEGF antibody-like constructs also are contemplated, such as the single-chain antibody fragment VEGF Inhibitor brolucizumab (also known as RTH258). Further, the compounds of general formula 1 may be used in combination with VEGF receptor modulators or inhibitors such as antibody and small molecule inhibitors of the VEGF receptor or of downstream signaling mechanisms. Examples, by way of example and not limitation, include sunitnib, sorafenib, cabozantinib, ponantinib, and axitinib. The disclosure contemplates a therapeutic regimen comprising administration of the compound of formula 1 and administration of any one or more of the following: an aptamer that inhibits VEGF expression or function, such as pegaptanib sodium (Macugen, Eyetech Pharmaceuticals, Cedar Knolls, NJ; an aptamer that selectively binds the VEGFA 165 isoform); a tyrosine kinase inhibitor (e.g., PAN-90806, a topical Anti-VEGF eye drop, PanOptica, Bernardsville, NJ); siRNA (e.g., Bevasiranib); soluble VEGF or a gene therapy vector encoding a soluble VEGF, such as RGX-314 (Regenxbio Inc); or a soluble VEGF receptor protein, such as conbercept (a fusion of domain 2 of VEGFR-1, domains 3 and 4 of VEGFR-2, and IgG1 Fc region).

In these embodiments, the compounds that make up the combination are co-administered to a subject. The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent. "Concomitant administration" of a known therapeutic drug with a pharmaceutical composition of the present disclosure means administration of the compound and second agent at such time that both the known drug and the composition of the present invention will have a therapeutic effect. Such concomitant administration may involve concurrent (i.e., at the same time), prior, or subsequent administration of the drug with respect to the administration of a subject compound. Routes of administration of the two agents may vary, where representative routes of administration are described in greater detail below. A person of ordinary skill in the art would have no difficulty determining the appropriate timing, sequence and dosages of administration for particular drugs and compounds of the present disclosure. In some embodiments, the compounds (e.g., a subject compound and the at least one additional compound) are administered to the subject within twenty-four hours of each other, such as within 12 hours of each other, within 6 hours of each other, within 3 hours of each other, or within 1 hour of each other. In certain embodiments, the compounds are administered within 1 hour of each other. In certain embodiments, the compounds are administered substantially simultaneously. By administered substantially simultaneously is meant that the compounds are administered to the subject within about 10 minutes or less of each other, such as 5 minutes or less, or 1 minute or less of each other.

h. Pharmaceutical Forms

Suitable preparations for administering the compounds of formula 1 and the co-crystal or salt forms of formulae 2 and 2a include for example tablets, capsules, suppositories, solutions and powders etc. The content of the pharmaceutically active compound(s) should be in the range from 0.05 to 90 wt.-%, such as 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatin, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly, the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g., with the addition of isotonic agents, preservatives such as p-hydroxybenzoates or stabilizers such as alkali metal salts of ethylenediaminetetraacetic acid, optionally using emulsifiers and/or dispersants, while if water is used as diluent, for example, organic solvents may optionally be used as solubilizers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatin capsules.

Suitable suppositories may be made for example by mixing with carriers provided for this purpose, such as neutral fats or polyethylene glycol or the derivatives thereof.

Excipients which may be used include, for example, water, pharmaceutically acceptable organic solvents such as paraffins (e.g., petroleum fractions), vegetable oils (e.g., groundnut or sesame oil), mono- or polyfunctional alcohols (e.g., ethanol or glycerol), carriers such as, e.g., natural mineral powders (e.g., kaolins, clays, talc, chalk), synthetic mineral powders (e.g., highly dispersed silicic acid and silicates), sugars (e.g., cane sugar, lactose and glucose), emulsifiers (e.g., lignin, spent sulphite liquors, methylcellulose, starch and polyvinylpyrrolidone) and lubricants (e.g., magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, such as potato starch, gelatin and the like. Lubricants such as magnesium stearate, sodium laurylsulphate and talc may also be used to produce the tablets. In the case of aqueous suspensions the active substances may be combined with various flavor enhancers or colorings in addition to the abovementioned excipients.

For administering the compounds of formula 1 or the co-crystal or salt forms of formulae 2 and 2a in some instances preparations or pharmaceutical formulations which are suitable for inhalation are employed. Inhalable preparations include inhalable powders, propellant-containing metered-dose aerosols or propellant-free inhalable solutions. Within the scope of the present invention, the term propellant-free inhalable solutions also include concentrates or sterile inhalable solutions ready for use. The formulations which may be used within the scope of the present invention are described in more detail in the next part of the specification.

The inhalable powders which may be used according to the invention may contain a compound of formula 1 or a co-crystal or salt form of formulae 2 and 2a either on their own or in admixture with suitable physiologically acceptable excipients.

If the active substances of the compounds of formula 1 or the co-crystal or salt forms of formulae 2 and 2a are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g., dextrans), polyalcohols (e.g. sorbitol, mannitol, xylitol), salts (e.g. sodium chloride, calcium carbonate) or mixtures of these excipients. In some instances, mono- or disaccharides are used, such as lactose or glucose, e.g., in the form of their hydrates. In some instances, lactose, e.g., in the form of lactose monohydrate, is employed as an excipient.

Within the scope of the inhalable powders according to the invention the excipients have a maximum average particle size of up to 250 µm, such as between 10 and 150 µm, and including between 15 and 80 µm. It may sometimes seem appropriate to add finer excipient fractions with an average particle size of 1 to 9 µm to the excipient mentioned above. These finer excipients are also selected from the group of possible excipients listed hereinbefore. Finally, in order to prepare the inhalable powders according to the invention, micronized active substance of the compounds of formula 1 or the co-crystal or salt forms of formulae 2 and 2a, such as with an average particle size of 0.5 to 10 µm, including from 1 to 5 µm, is added to the excipient mixture. Processes for producing the inhalable powders according to the invention by grinding and micronising and finally mixing the ingredients together are known from the prior art.

The inhalable powders according to the invention may be administered using inhalers known from the prior art.

The inhalation aerosols containing propellant gas according to the invention may contain a compound of formula 1 or a co-crystal or salt form of formulae 2 and 2a dissolved in the propellant gas or in dispersed form. The compounds of formula 1 or the co-crystal or salt forms of formulae 2 and 2a may be contained in separate formulations or in a common formulation, in which they are either both dissolved, both dispersed or in each case only one component is dissolved and the other is dispersed. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The abovementioned propellant gases may be used on their own or mixed together. Specific propellant gases that may be employed are halogenated alkane derivatives selected from TG134a and TG227 and mixtures thereof.

The propellant-driven inhalation aerosols may also contain other ingredients such as co-solvents, stabilizers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances of the compounds of formula 1 or the co-crystal or salt forms of formulae 2 and 2a according to the invention may be administered in the form of propellant-free inhalable solutions and suspensions. The solvent used may be an aqueous or alcoholic, such as an ethanolic solution. The solvent may be water on its own or a mixture of water and ethanol. The relative proportion of ethanol compared with water is not limited but the maximum may, in some instances, be up to 70 percent by volume, such as up to 60 percent by volume and including up to 30 percent by volume. The remainder of the volume may be made up of water. The solutions or suspensions containing a compound of formula 1 or a co-crystal or salt form of formulae 2 and 2a are adjusted to a pH of 2 to 7, such as 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Inorganic acids that are employed in some instances are hydrochloric and sulfuric acids. It is also possible to use the acids which have already formed an acid addition salt with one of the active substances. Of the organic acids, ascorbic acid, fumaric acid and citric acid are employed in some instances. If desired, mixtures of the above acids may be used, particularly in the case of acids which have other properties in addition to their acidifying qualities, e.g. as flavorings, antioxidants or complexing agents, such as citric acid or ascorbic acid, for example. According to the invention, in some instances hydrochloric acid to adjust the pH.

If desired, the addition of editic acid (EDTA) or one of the known salts thereof, sodium edetate, as stabilizer or complexing agent may be omitted in these formulations. Other embodiments may contain this compound or these compounds. In an embodiment the content based on sodium edetate is less than 100 mg/100 ml, such as less than 50 mg/100 ml, including less than 20 mg/100 ml. Inhalable solutions in which the content of sodium edetate is from 0 to 10 mg/100 ml are employed in some instances. Co-solvents and/or other excipients may be added to the propellant-free inhalable solutions. Co-solvents that may be employed are those which contain hydroxyl groups or other polar groups, e.g., alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. In some instances, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilizers, complexing agents, antioxidants and/or preservatives which guarantee or prolong the shelf life of the finished pharmaceutical formulation, flavorings, vitamins and/or other additives known in the art. The additives also include pharmacologically acceptable salts such as sodium chloride as isotonic agents.

Excipients employed in some embodiments include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are, in some instances, present in concentrations of up to 50 mg/100 ml, more preferably between 5 and 20 mg/100 ml. Formulations of some embodiments contain, in addition to the solvent water and the compounds of formula 1 or the co-crystal or salt forms of formulae 2 and 2a, only benzalkonium chloride and sodium edetate. In an embodiment, no sodium edetate is present.

The dosage of the compounds according to the invention is naturally highly dependent on the method of administration and the complaint which is being treated. When administered by inhalation the compounds of formula 1 or the co-crystal or salt forms of formulae 2 and 2a are characterized by a high potency even at doses in the μg range. The compounds of formula 1 or the co-crystal or salt forms of formulae 2 and 2a may also be used effectively above the μg range. The dosage may then be in the gram range, for example.

In another aspect the present invention relates to the above-mentioned pharmaceutical formulations as such which are characterized in that they contain a compound of formula 1 or a co-crystal or salt form of formulae 2 and 2a, particularly the above-mentioned pharmaceutical formulations which can be administered by inhalation.

The following examples of formulations illustrate the present invention without restricting its scope.

| A) | Tablets | per tablet |
|---|---|---|
| | active substance 1, 2, or 2a | 100 mg |
| | lactose | 140 mg |
| | maize starch | 240 mg |
| | polyvinylpyrrolidone | 15 mg |
| | magnesium stearate | 5 mg |
| | | 500 mg |

The finely ground active substance, lactose and some of the maize starch are mixed together. The mixture is screened, then moistened with a solution of polyvinylpyrrolidone in water, kneaded, wet granulated and dried. The granules, the remaining maize starch and the magnesium stearate are screened and mixed together. The mixture is pressed into tablets of suitable shape and size.

| B) | Tablets | per tablet |
|---|---|---|
| | active substance 1, 2, or 2a | 80 mg |
| | lactose | 55 mg |
| | maize starch | 190 mg |
| | microcrystalline cellulose | 35 mg |
| | polyvinylpyrrolidone | 15 mg |
| | sodium carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) | Ampoule solution | |
|---|---|---|
| | active substance 1, 2, or 2a | 50 mg |
| | sodium chloride | 50 mg |
| | water for inj. | 5 ml |

The active substance is dissolved in water at its own pH or optionally at pH 5.5 to 6.5 and sodium chloride is added to make the solution isotonic. The resulting solution is filtered to remove pyrogens and the filtrate is transferred under aseptic conditions into ampoules which are then sterilized and heat-sealed. The ampoules contain 5 mg, 25 mg and 50 mg of active substance.

| D) | Metering aerosol | |
|---|---|---|
| | active substance 1, 2, or 2a | 0.005 |
| | sorbitan trioleate | 0.1 |
| | monofluorotrichloromethane and TG134a:TG227 2:1 | ad 100 |

The suspension is transferred into a conventional aerosol container with metering valve. Preferably 50 µl suspension are released on each actuation. The active substance may also be released in higher doses if desired (e.g. 0.02 wt.-%).

| E) | Solutions (in mg/100 ml) | |
|---|---|---|
| | active substance 1, 2, or 2a | 333.3 mg |
| | benzalkonium chloride | 10.0 mg |
| | EDTA | 50.0 mg |
| | HCl (1N) | ad pH 2.4 |

This solution can be prepared in the usual way.

| F) | Inhalable powder | |
|---|---|---|
| | active substance 1, 2, or 2a | 12 µg |
| | lactose monohydrate | ad 25 mg |

The inhalable powder is prepared in the usual way by mixing the individual ingredients.

i. Indications

Methods of improving visual acuity are provided, including methods of improving visual acuity through treating a subject/patient for retina-associated diseases. In some aspects, the subject is suffering from (or diagnosed as suffering from) a retina-associated disease resulting in loss of visual acuity. The retina-associated disease may be associated with neovascularization, or the retina-associate disease may not include a vascular component (i.e., may not stem from or be associated with neovascularization). For example, the patient may, in various embodiments, suffer from loss of visual acuity which is not caused by ocular neovascularization. Aspects of the methods include modulating CCR3, e.g., with a CCR3 modulating agent in a manner sufficient to improve visual acuity and, in various aspects, treat the patient for the retina-associated disease. The methods include improving visual acuity (e.g., by treating the retina-associated disease) with an orally administrable and bioavailable composition, including a composition of compound of formula 1, a co-crystal or salt of formulae 2 or 2a, or a formulation of formula 3, described above. The composition, which modulates CCR3, can be administered to a patient/subject in need of improvement in visual acuity, including subjects diagnosed with the retina-associated disease, such as age-related macular degeneration (dry or wet forms), central retinal vein occlusion, central retinal artery occlusion, macular edema (such as diabetic macular edema), glaucoma, Stargardt disease, retinopathy of prematurity, or diabetic retinopathy which are further described below. The methods of the invention can further comprise monitoring improvement in the progression of the retina-associated disease through visual acuity or other tests. Various exemplary retina-associate disease indications are described in further detail below.

j. Retina-Associated Disease Indications i. Macular Degeneration

Macular Degeneration. Macular degeneration is a clinical term that is used to describe a family of disease that are all characterized by a progressive loss of central vision associated with abnormalities of Bruch's membrane, the choroid, the neural retina and/or the retinal pigment epithelium. These disorders include very common conditions that affect older subjects-such as age-related macular degeneration (AMD) as well as rarer, earlier-onset dystrophies that in some cases can be detected in the first decade of life. Other maculopathies include North Carolina macular dystrophy, Best disease, and Malattia leventinese.

AMD is the leading cause of permanent vision loss for individuals over the age of 65, currently affecting approximately 15 million Americans. AMD affects light-sensitive photoreceptor cells and pigmented epithelial cells in the macula, the center of the retina of the eye. While it may not cause total blindness, the disease destroys central vision, making reading, watching electronic monitor screens, and driving impossible. It has no documented cure, has never demonstrated spontaneous remission, and effective treatments are limited with substantial burden upon patient and caregiver as well as side effects.

The retina, or neural portion of the eye, is a complicated network of nerve cells that changes light into nerve impulses that travel to the brain where they are interpreted as visual images. There are five types of neurons in the retina. These include photoreceptors, bipolar cells, ganglion cells, horizontal cells, and amacrine cells. The central part of the retina, called the macula, is responsible for vision that is needed for reading and other detailed work. Damage to the macula results in poor vision. The most common disease process that affects the macula is AMD. In patients with AMD, retinal photoreceptor and pigment epithelial cells in the macula die over the course of several years. The cell death and gradual visual loss usually do not begin until age 60 or older, thus the name, age-related macular degeneration.

There are two types of AMD: dry macular degeneration and wet macular degeneration. Dry macular degeneration, although more common, typically results in a less severe, more gradual loss of vision. Patients who are affected by dry AMD have gradual loss of central vision due to the death of photoreceptor cells and their close associates, retinal pigmented epithelial (RPE) cells, with deposition of a complex waxy amyloid mixture, termed 'drusen'. Photoreceptors, the cells in the retina that actually 'see' light, are essential for vision. Macrophagic RPE cells are necessary for photoreceptor survival, function and renewal. Patients with wet macular degeneration develop new blood vessels under the retina. As the photoreceptor and RPE cells slowly degenerate, there is a tendency for blood vessels to grow from their normal location in the choroid into an abnormal location beneath the retina. This abnormal new blood vessel growth is called choroidal neovascularization (CNV). The abnormal blood vessels leak and bleed, causing hemorrhage, swelling, scar tissue, and severe loss of central vision. Only 10% of patients with AMD have the wet type, but it is responsible for 90% of all blindness resulting from AMD.

ii. Central Retinal Vein Occlusion (CRVO)

Central Retinal Vein Occlusion, also known as CRVO, occurs when venous occlusion prevents oxygen-depleted blood from flowing out of the eye's vasculature. As a result of reduced flow of oxygen-depleted blood in the eye, oxygen-rich blood is inhibited from reaching the retina's surface layers, resulting in a hypoxic state. In response, the surface layers of the retina produce pro-angiogenic factors which contribute to the development of abnormal macular edema and neovascularization. One of the utilities of the compounds of formula 1 is the treatment of the macular edema and neovascularization resulting from CRVO.

iii. Retinopathy of Prematurity

Affecting prematurely born babies, Retinopathy of Prematurity (ROP) is an eye disease associated with both oxygen toxicity and local hypoxia. These conditions are thought to contribute to the development of ROP. The underlying pathophysiology of the disease is that hypoxic conditions lead to stimulation of pro-angiogenic factors that cause disorganized growth of blood vessels with result in scarring and retinal detachment. Some patients with ROP can have it in a mild form and fully recover without therapeutic intervention, but in others it can lead to permanent blindness. The exact cause of the disease is unknown but leading hypotheses are that supplemental oxygen either causes local retinal hypoxia through vasoconstriction which triggers neovascularization, or that normal vascular processes are blunted by supplemental oxygen, but when it is suddenly removed results a rapid proliferation of vascular and fibrovascular disease. Surgery and therapeutic intervention are current therapies to treat the disease in its severe form. Surgical therapy can include sclera buckling and/or vitrectomy for retinal detachment. Laser induced photocoagulation is however the mainstay of ROP treatment currently. The compounds of formula 1 have utility in the prevention of neo-vascularization associated with ROP. The compounds described herein are useful for improving visual acuity associated with ROP.

iv. Diabetic Retinopathy

Diabetic Retinopathy is a complication from diabetes that can cause blindness. The mechanism through which it is caused is damage to the blood vessels of the retinal tissue. Diabetic Retinopathy can develop in subjects with either Type 1 or Type 2 diabetes, which is associated with loss of control of blood sugar content. Symptoms include spots or floaters in the subject's vision, blurred vision, fluctuating vision, impaired color vision, dark/empty areas of vision, and vision loss, usually affecting both eyes. The cause of this disease is too much sugar in the subject's blood, leading to blockage of the blood vessels that nourish the retina and resulting in blockage of retinal blood supply. In response, the retina attempts to grow new blood vessels, producing pro-angiogenic factors. Improper regulation of the growth of these blood vessels ensues, resulting in vessels that leak readily.

Two types of Diabetic Retinopathy exist: Early Diabetic Retinopathy, or Non-proliferative Diabetic Neuropathy (NPDR) and Advanced Diabetic Retinopathy. NPDR results when new blood vessels do not grow, resulting in the walls of the retinal blood vessels weakening and the occurrence of microaneurysms. These microaneurysms can protrude and leak fluid and blood into the retina. As more blood vessels are blocked, the NPDR gets more severe. Retinal nerve fibers as well as the macula (central part of the retina) can swell, a condition known as macular edema. In Advanced Diabetic Retinopathy (or Proliferative Diabetic Retinopathy), blood vessels that have been damaged close off, which causes new, abnormal blood vessels to grow, and results in leakage into the vitreous of the eye. Scar tissue that results from the new blood vessel growth can cause retinal detachment as well as increased eye pressure-ultimately causing damage to the optic nerve and glaucoma.

k. Methods of Diagnosing and Monitoring for Improvement of Retina-Associated Disease and Visual Acuity i. Introduction The methods of the invention further comprise methods of diagnosing retina-associated disease. Such methods may include, by way of example, and not limitation, visual acuity (VA) tests, macular degeneration or Amsler grids, retina examination with dilated pupils, fundus photography, fluorescein angiography, or optical coherence tomography (OCT) which can determine such endpoints as central retinal thickness (CRT).

ii. Visual Acuity (VA)

One method that can diagnose or determine disease progression/improvement is testing for visual acuity. Methods for testing for visual acuity are well-known to those having ordinary skill in the art. Visual acuity tests the sharpness of the subject's vision, often using an "eye chart" the most common of which is the Snellen eye chart. Other methods of testing for visual acuity include use of the Early Treatment Diabetic Retinopathy Study (ETDRS) chart, which, as with other VA tests, can be used to diagnose and measure progression/improvement in visual acuity of subjects with retina-associated diseases such as, by way of example and not limitation, macular degeneration, central retinal vein occlusion, retinopathy of prematurity, and diabetic retinopathy. (See Bokinni, Y, et al., Eye 29:1085-91 (2015)).

One method of determining improvement in visual acuity in a patient is determining whether the subject, after treatment, is able to identify more letters on the Snellen, ETDRS, or other similar charts than they were able to before treatment. Since such visual acuity tests require communication between the subject and the medical professional (e.g., reading letters out-loud), it is difficult to get analogous readouts in visual acuity when testing on animal models in pre-clinical studies.

Visual acuity has the advantage of being a clinical endpoint that can be independent of other visual tests that depend upon observation of retinal vascularization or neovascularization such as fundus photography/observation, fluorescein angiography, or even optical coherence tomography. That is, if an improved effect on visual acuity is due not to a mechanism affecting the retinal vasculature, then this test can still reveal the efficacy of a treatment. While the magnitude of improvement may vary for a given patient, in some instances the magnitude of improvement as determined using a visual acuity test, e.g., as described above, is 5% or more, such as 10% or more, including 20% or more.

iii. Macular Degeneration/Amsler Grids

One method that is commonly used to diagnose macular degeneration and to determine disease progression is the use Amsler (macular degeneration) grids, the methods of which are well known to those having ordinary skill in the art. The grid comprises a square similar in appearance to graph paper, with dark lines forming a square grid and a dark dot in the middle of the square. Covering each eye in succession, the subject focuses each individual eye on the dark dot, and takes note if any of the lines of the grid are broken, distorted, wavy, or blurry.

iv. Comprehensive Retinal Examination with Pupil Dilation

Comprehensive retinal examination with pupil dilation is a method through which the retina may be observed directly by a practitioner such as an optometrist or ophthalmologist and is well-known to those having ordinary skill in the art. The practitioner administers dilating eye drops to the subject. The drops can be of two types of mydriatic medications, either administered together or separately. One stimulates contraction of the muscles that dilate the pupil (e.g., phenylephrine), and the other type relaxes the muscles that make the pupil constrict (e.g., cyclopentolate). Pupil dilation allows the practitioner to better observe a larger field of the retina during eye examination.

Comprehensive retinal examination with pupil dilation allows ophthalmologists to diagnose and determine disease progression of various eye and retina-associated diseases such as, by way of example and not limitation, glaucoma, diabetic retinopathy, retinopathy of prematurity, central retinal vein occlusion, and age-related macular degeneration. Telltale signs of these diseases that can be determined by fundus photography include swell or leaking of blood vessels in the retina, abnormal growth of blood vessels in or beneath the retina, and deterioration of the macula of the retina.

v. Fundus Photography

Similar to retinal examination with pupil dilation, fundus photography is a method through which the retina may be photographed directly and is well-known to those having ordinary skill in the art. (Saine, P J, et al., *Fundus Photography Overview*, OPHTHALMIC PHOTOGRAPHY: RETINAL PHOTOGRAPHY, ANGIOGRAPHY, AND ELECTRONIC IMAGING, Butterworth-Heinemann Medical (2nd ed.)). The procedure includes pupil dilation, with the patient sitting before the fundus camera. A flash sends light into the patient's eye, creating a fundus photograph or image of the retina. The photography can be performed with various colored filters, or the patient can be administered dues such as fluorescein to aid in imaging.

A fundus camera is a specialized, low power microscope attached to a camera. The angle of acceptance of the lens can create different outputs. A 30-degree angle is considered by those having ordinary skill in the art to be the normal view of the retina. Wide angle fundus cameras are capable of capturing images between 45 and 140 degrees, and narrow angle fundus cameras have angle views of 20 degrees or less.

As with comprehensive retinal examination with pupil dilation, fundus photography allows ophthalmologists to diagnose and determine disease progression of various eye and retina-associated diseases such as, by way of example and not limitation, glaucoma, retinopathy of prematurity, diabetic retinopathy, central retinal vein occlusion and age-related macular degeneration. Telltale signs of these diseases that can be determined by fundus photography include swell or leaking of blood vessels in the retina, abnormal growth of blood vessels in or beneath the retina, and deterioration of the macula of the retina.

vi. Fluorescein Angiography

Fluorescein angiography is a method through which the blood vessels of the retina can be evaluated and is well-known to those having ordinary skill in the art. It is used most commonly for diagnosing or measuring progression of wet macular degeneration/choroidal neovascularization.

Fluorescein dye is injected into the vein of a subject (whose eyes have been dilated prior) in order for the dye to travel to the eye and the vasculature of the retina. Before the dye is injected, baseline photos of the retina are taken. When it is determined that the dye has entered retinal vasculature, additional photos are taken of the retina over the span of one to several minutes. Viewing the photographs, the ophthalmologist can determine if any of the dye leaked from the vessels, which helps them understand where new and fragile blood vessels have developed.

vii. Optical Coherence Tomography (OCT)

OCT is a non-invasive test that provides high-resolution cross-sectional images of a retina and employs light waves to produce the images. (Fujimoto, J G, et al., *Neoplasia*, 2(1-2):9-25 (January 2000)). OCT allows for each of the distinctive layers of the retina to be imaged. Accordingly, an ophthalmologist is given the means through which they can map the retina and determine its thickness. By way of example, and not limitation, the central retinal thickness (CRT) of the subject's retina can be precisely measured. The methods of performing an OCT test as well as determining CRT are well-known to those of skill in the art.

OCT can be performed using eye drops which dilate the pupils and allow better examination of the subject's retinas. Once the pupils are fully dilated, the subject the OCT scanner may scan the subject's eyes in a non-invasive fashion. OCT can help to diagnose many retina-associated conditions/diseases including macular edema, age-related macular degeneration, glaucoma, diabetic retinopathy, and retinopathy of prematurity.

l. Reagents, Devices, and Kits

Also provided are reagents, devices, and kits thereof for practicing one or more of the above-described methods. The subject reagents, devices, and kits thereof may vary greatly. Reagents and devices of interest include those mentioned above with respect to the methods of administering the compounds described herein (e.g., the compounds for formula 1) to the subject.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g. diskette, CD, portable flash drive, etc., on which the information has been recorded. Yet another means that may be present is a website address which may be used via the internet to access the information at a remote site. Any convenient means may be present in the kits.

The following examples are provided by way of illustration and not by way of limitation.

Examples a. Pharmaceutical Preparation

The pharmaceutical compositions that are administered to subjects with retina-associated disease that are comprised of the compounds, co-crystals, and salts described above can be synthesized, made, and formulated using the examples disclosed in U.S. Patent Application Publication Nos. 2013/0266646, 2016/0081998, U.S. Pat. Nos. 8,278,302, 8,653,075, RE 45323, 8,742,115, 9,233,950, and 8,680,280, which are herein incorporated by reference in their entirety. Further, the pharmaceutical compositions may be prepared as described in the examples below:

1. Tablet Formulation—Wet Granulation

Copovidone is dissolved in ethanol at ambient temperature to produce a granulation liquid. An active CCR3 antagonist ingredient, lactose and part of the crospovidone are blended in a suitable mixer, to produce a pre-mix. The pre-mix is moistened with the granulation liquid and subsequently granulated. The moist granulate is optionally sieved through a sieve with a mesh size of 1.6-3.0 mm. The granulate is dried at 45° C. in a suitable dryer to a residual moisture content corresponding to 1-3% loss on drying. The dried granulate is sieved through a sieve with a mesh size of 1.0 mm. The granulate is blended with part of the crospovidone and microcrystalline cellulose in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
| --- | --- | --- |
| Active ingredient | 28.500 | 30.0 |
| Crospovidone | 1.500 | 1.6 |
| Lactose | 28.000 | 29.5 |
| Copovidone | 3.000 | 3.2 |
| Total (granulate) | 61.000 | 64.3 |
| Microcrystalline cellulose | 31.000 | 32.6 |
| Crospovidone | 2.500 | 2.6 |
| Magnesium stearate | 0.500 | 0.5 |
| Total | 95.000 | 100.000 |

2. Tablet Formulation—Melt Granulation

An active CCR3 antagonist ingredient, lactose, part of the mcc, polyethylene glycole, lactose and part of the crospovidone are blended in a suitable mixer, to produce a pre-mix. The pre-mix is heated in a high shear mixer and subsequently granulated. The hot granulate is cooled down to room temperature and sieved through a sieve with a mesh size of 1.0 mm. The granulate is blended with part of the crospovidone and microcrystalline cellulose in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
| --- | --- | --- |
| Active ingredient | 28.500 | 30.0 |
| Crospovidone | 1.500 | 1.6 |
| Lactose | 11.000 | 11.6 |
| Polyethylene glycole | 14.300 | 15.1 |
| MCC | 5.700 | 6.0 |
| Total (granulate) | 61.000 | 64.3 |
| Microcrystalline cellulose | 31.000 | 32.6 |
| Crospovidone | 2.500 | 2.6 |
| Magnesium stearate | 0.500 | 0.5 |
| Total | 95.000 | 100.000 |

3. Tablet Formulation—Hot Melt Granulation

An active CCR3 antagonist ingredient, mannit, polyethylene glycole and part of the crospovidone are blended in a suitable mixer, to produce a pre-mix. The pre-mix is heated in a high shear mixer and subsequently granulated. The hot granulate is cooled down to room temperature and sieved through a sieve with a mesh size of 1.0 mm. The granulate is blended with part of the crospovidone and mannit in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
| --- | --- | --- |
| Active ingredient | 28.500 | 30.0 |
| Crospovidone | 1.500 | 1.6 |
| Mannit | 16.700 | 17.6 |
| Polyethylene glycole | 14.300 | 15.1 |
| Total (granulate) | 61.000 | 64.3 |
| Mannit | 31.000 | 32.6 |
| Crospovidone | 2.500 | 2.6 |
| Magnesium stearate | 0.500 | 0.5 |
| Total | 95.000 | 100.000 |

4. Tablet Formulation—Hot Melt Extrusion

An active CCR3 antagonist ingredient and stearic-palmitic acid are blended in a suitable mixer, to produce a pre-mix. The pre-mix is extruded in a twin-screw-extruder and subsequently granulated. The granulate is sieved through a sieve with a mesh size of 1.0 mm. The granulate is blended with mannit and crospovidone in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
| --- | --- | --- |
| Active ingredient | 28.500 | 30.0 |
| Stearic-palmitic acid | 27.500 | 28.9 |
| Total (granulate) | 56.000 | 58.9 |
| Mannit | 32.600 | 34.3 |
| Crospovidone | 5.600 | 5.9 |
| Magnesium stearate | 0.800 | 0.9 |
| Total | 95.000 | 100.000 |

5. Tablet Formulation—Hot Melt Extrusion

An active CCR3 antagonist ingredient and stearic-palmitic acid are blended in a suitable mixer, to produce a pre-mix. The pre-mix is extruded in a twin-screw-extruder and subsequently granulated. The granulate is sieved through a sieve with a mesh size of 1.0 mm. The granulate is directly filled into hard capsules. The following capsule composition can be obtained:

| Component | mg/tablet | %/tablet |
| --- | --- | --- |
| Active ingredient | 70.000 | 70.0 |
| Stearic-palmitic acid | 30.000 | 30.0 |
| Total (granulate) | 100.000 | 100.0 |
| Capsule | 90.000 | — |
| Total | 190.000 | 100.000 |

6. Tablet Formulation—Roller Compaction

An active CCR3 antagonist ingredient, part of mannit and crospovidone and magnesium stearate are blended in a suitable mixer, to produce a pre-mix. The pre-mix is compacted with a roller compactor and subsequently granulated. Optionally, the granulate is sieved through a sieve with a mesh size of 0.8 mm. The granulate is blended with part of mannit and crospovidone in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
| --- | --- | --- |
| Active ingredient | 28.500 | 30.0 |
| Crospovidone | 1.400 | 1.5 |
| Mannit | 34.600 | 36.4 |
| Magnesium stearate | 0.500 | 0.5 |
| Total (granulate) | 65.000 | 68.4 |
| Mannit | 27.000 | 28.4 |
| Copovidone | 1.600 | 1.7 |
| Crospovidone | 0.950 | 1.0 |
| Magnesium stearate | 0.450 | 0.5 |
| Total | 95.000 | 100.000 |

7. Tablet Formulation—Roller Compaction

An active CCR3 antagonist ingredient and magnesium stearate are blended in a suitable mixer, to produce a pre-mix. The pre-mix is compacted with a roller compactor and subsequently granulated. Optionally, the granulate is sieved through a sieve with a mesh size of 0.8 mm. The granulate is blended with mannit and croscarmellose sodium in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
| --- | --- | --- |
| Active ingredient | 114.200 | 66.0 |
| Magnesium stearate | 1.800 | 1.0 |
| Total (granulate) | 116.000 | 67.0 |
| Mannit | 51.000 | 29.5 |
| Croscarmellose sodium | 3.500 | 2.0 |
| Magnesium stearate | 2.500 | 1.5 |
| Total | 173.000 | 100.000 |

8. Tablet Formulation—Roller Compaction

An active CCR3 antagonist ingredient and magnesium stearate are blended in a suitable mixer, to produce a pre-mix. The pre-mix is compacted with a roller compactor and subsequently granulated. Optionally, the granulate is sieved through a sieve with a mesh size of 0.8 mm. The granulate is blended with microcrystalline cellulose and crospovidone in a suitable mixer. Magnesium stearate is added to this blend after passing through a 1.0 mm sieve for de-lumping. Subsequently the final blend is produced by final blending in a suitable mixer and compressed into tablets. The following tablet composition can be obtained:

| Component | mg/tablet | %/tablet |
| --- | --- | --- |
| Active ingredient | 114.200 | 66.0 |
| Magnesium stearate | 1.800 | 1.0 |
| Total (granulate) | 116.000 | 67.0 |
| MCC | 51.000 | 29.5 |
| Crospovidone | 3.500 | 2.0 |
| Magnesium stearate | 2.500 | 1.5 |
| Total | 173.000 | 100.000 |

9. Coated Tablet Formulation

Tablet cores according above mentioned formulations can be used to produce film-coated tablets. Hydroxypropyl methylcellulose, polyethylene glycol, talc, titanium dioxide and iron oxide are suspended in purified water in a suitable mixer at ambient temperature to produce a coating suspension. The tablet cores are coated with the coating suspension to a weight gain of about 3% to produce film-coated tablets. The following film coating composition can be obtained:

| Component | mg/tablet | %/tablet |
| --- | --- | --- |
| Hypromellose | 2.40 | 48.0 |
| Polyethylene glycol 6000 | 0.70 | 14.0 |
| Titanium dioxide | 0.90 | 18.0 |
| Talcum | 0.90 | 18.0 |
| Iron oxide red | 0.10 | 2.0 |
| Purified water (volatile component) | — | — |
| Total | 5.00 | 100.0 | b. Drug Formulation and Administration

The investigational product of the invention conformed to the following chemical structure:

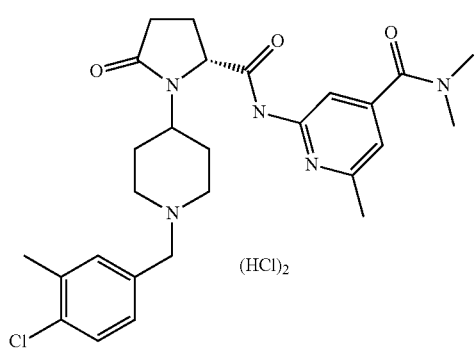 [SMILES: Cc1cc(C(=O)N(C)C)cc(NC(=O)[C@H]2CCC(=O)N2C2CCN(Cc3ccc(Cl)c(C)c3)CC2)n1 ; "(HCl)2"]

Those having ordinary skill in the relevant art would recognize that the compounds, co-crystals, salts, and formulations described in the previously in the sections above could also be used in these examples.

The investigational product of the invention was made available as 100 mg, 200 mg, and 400 mg film-coated tablets with a biconvex, round or oval shape and a dull red color. The tablets were produced by a dry granulation process and contained microcrystalline cellulose, hydrogen phosphate, croscarmellose sodium, magnesium stearate, polyvinyl alcohol, titanium dioxide, polyethylene glycol, talc, iron oxide red and iron oxide yellow as inactive ingredients. Placebo tablets matching the investigational product were produced by a direct compression process and contained the same inactive ingredients.

c. Pre-Clinical Examples

The antagonistic potency of the investigational product of the invention was determined in several human CCR3-dependent assays (FIG. 1). The investigational product of the invention's potency was determined via a receptor binding assay, with the $IC_{50}$ measured at 4.0±1.8 nM and the Ki at 3.2±0.6 nM. $IC_{50}$ for a calcium influx assay using human CCR3-transfected CHEM1-Gα15 cells was determined to be 0.9±0.2 nM. Antagonism by the investigational product of the invention of human eotaxin-1 induced eosinophil shape change in human whole blood was achieved with an $IC_{50}$ of 42.5±43.5 nM.

Potencies for several other mammalian species were also determined in different assays. Species included cynomolgus (macaque) monkeys, mouse, rat, and canines. With respect to receptor binding assays, the $K_i$ for the investigational drug of the invention on mouse CCR3 was 124.3±0.9 nM, and the $IC_{50}$ 87.3±5.6 nM. For rat CCR3, the Ki for the investigational drug of the invention was 1488.6±127.6 nM and the $IC_{50}$ 1719.0±129.9 nM.

d. Clinical Trial Design (Treatment—Naïve, 4 Week Regimen)

Patients with newly diagnosed (e.g. treatment—naïve) subfoveal CNV that was secondary to wAMD were entered into a single-arm, open-label study. Patients orally took 400 mg of the investigational drug of the invention b.o.d. (twice daily) for 4 weeks and had weekly scheduled visits with the physician. The regimen called for two 200 mg tablets in the morning and two 200 mg tablets in the evening. After the end of treatment (EoT) or on withdrawal from the study medication, eligible patients could receive standard of care therapy (anti-VEGF therapy). Patients were followed up twice within 4 weeks after EoT. FIG. 2 is a depiction of the clinical trial design. Boxes V1, V2, V3, V4, and V5 indicate patient visits 1 through 5, respectively. Gaps between the boxes indicate the time in days between visits. The box labeled EoT indicates visit 6, or the end of treatment. Visits 7 and 8 occurred during the follow-up (FU) visits.

1. Primary Endpoint—Central Retinal Thickness (CRT)

The primary endpoint was the change from baseline in central retinal thickness (CRT) as determined by spectral domain optical coherence tomography (SD-OCT) on day 29 (visit no. 6). For all primary and secondary endpoints, the value of the last assessment before first intake of study medication was used as the baseline on day 1 (visit no. 2).

Figure 3:
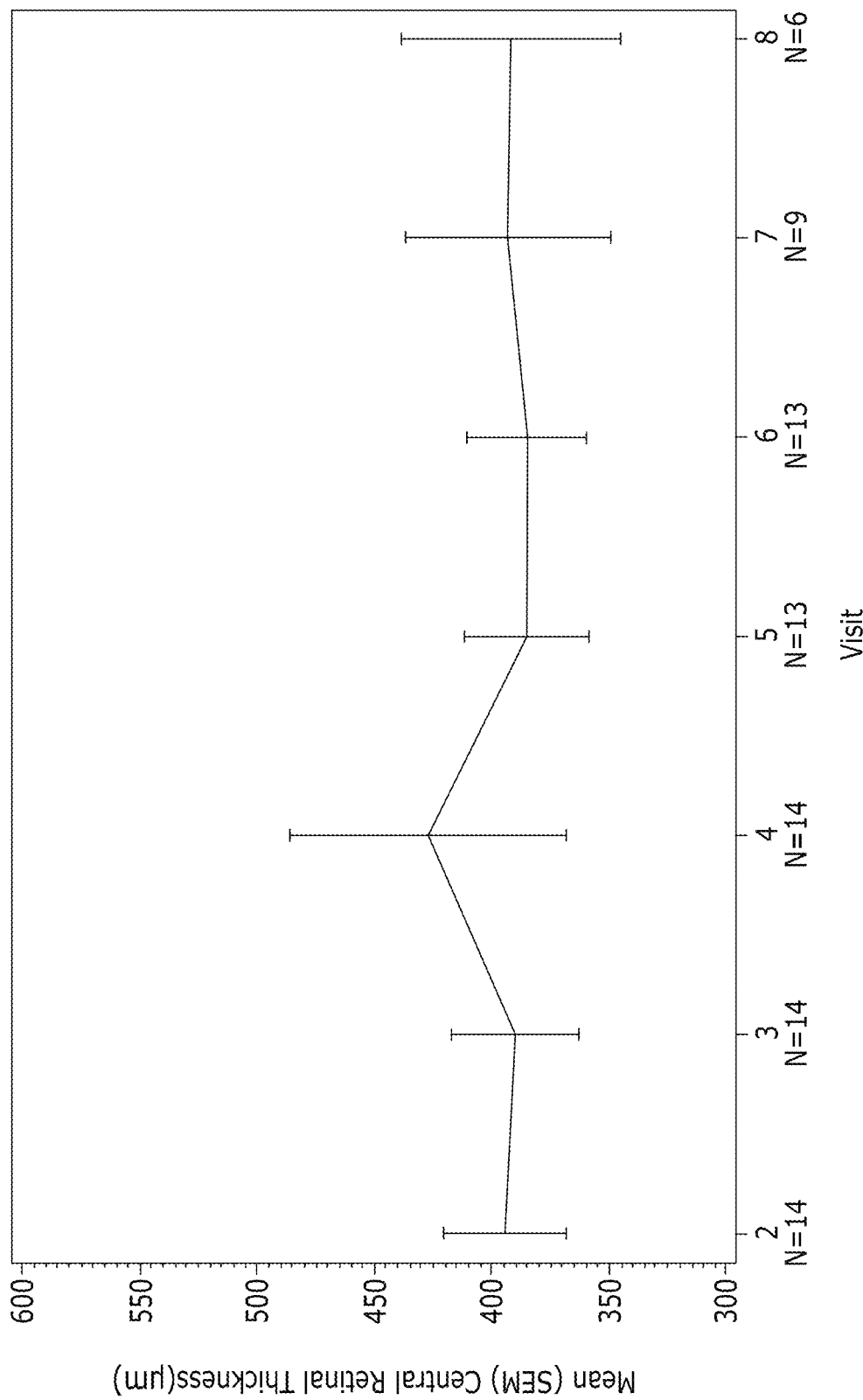
FIG. 3 depicts mean central 1-mm retinal thickness in patients over the clinical trial timeline described in FIG. 2.

FIG. 3 shows CRT over time. CRT was reported as mean (SEM) in units of μm and time as visit number. The retinal layers and thickness was visualized and measured by SD-OCT, and to those having ordinary of skill in the art and trained using OCT equipment, visualization and measurement of the retinal layers involve well-known techniques. (See, e.g., Fujimoto, J G, et al., Neoplasia 2(1-2)9-25 (2000); and Keane, P A, et al., Investigative Ophthalmology & Visual Science, 50(7):3378-85 (2009)). Overall, there was no significant change from baseline in median or mean CRT over time through the treatment phase.

2. Secondary Endpoints (a) Neovascular Leakage as Assessed by Fluorescein Angiography and Fundus Photography The retinal vasculature of the study eye was evaluated via fluorescein angiography (FA). The change in neovascular leakage by FA was determined on Day 29 (visit 6) compared to baseline. FIG. 4 reports absolute values as well as change in baseline over time as both mean and median values. N is the number of patients evaluated. Overall, there was no significant change from baseline in median or mean values over time through the treatment phase.

(b) Visual Acuity

Figure 5:
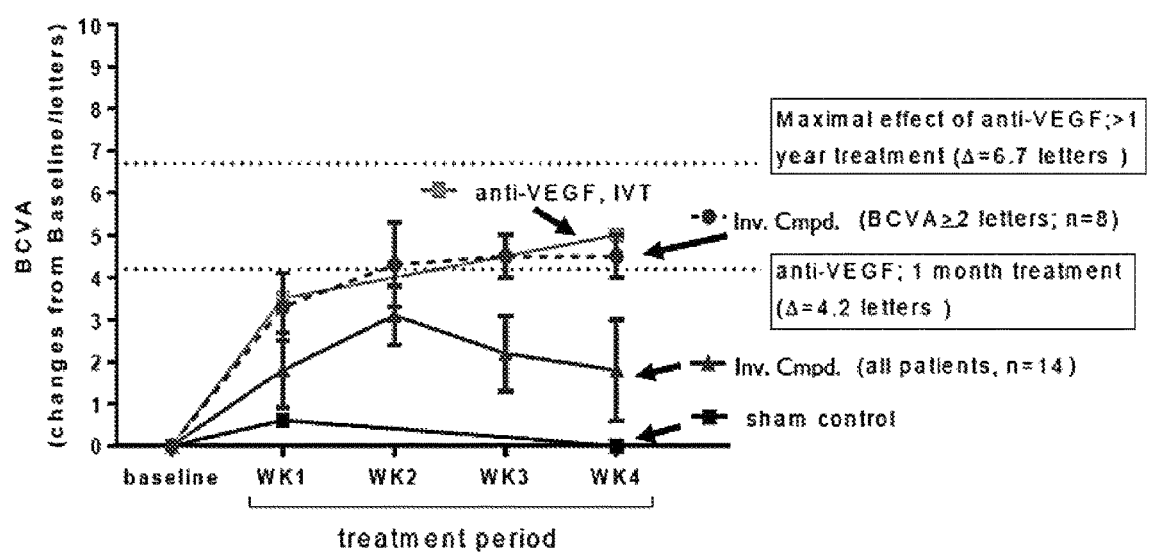
FIG. 5 depicts best-corrected visual acuity (BCVA) by number of letters read by patients over the time of trial described in FIG. 2. BCVA was tested using the ETDRS chart for visual acuity.

Visual acuity was determined using ETDRS charts over time of treatment. The absolute change in numbers of letters read by patients from their baseline levels was evaluated during visits. FIG. 5 depicts this change (x-axis) over time (y-axis) during treatment with the investigational drug of the invention (Inv. Cmpd.). Out of a total of 14 patients, a subset of 8 patients showed significant improvement in best corrected visual acuity (BCVA) compared to sham control and to the larger patient group overall. The improvement in visual acuity was surprising, at least in part, given that the therapy did not significantly affect central retinal thickness. For the subset of 8 patients, the best corrected visual acuity compared favorably with anti-VEGF therapy (ranibizumab intravitreal injection) as reported previously in the MARINA and VIEW studies. (Rosenfeld P J, et al., N. Engl. J. Med. 355(14):1419-31 (2006); and Heier J S, et al., Ophthalmology 119(12):2537-48 (2012)). Thus, remarkably, the method described herein achieved an improvement in visual acuity to levels observed in connection with anti-VEGF therapy, but employing a mechanism of action that differs from the current standard of care.

In light of the observation that the investigational compound of the invention failed to significantly alter central retinal thickness or neovascular leakage, this significant improvement in visual acuity in over half of the patients was both surprising and unexpected. It suggests that the investigational compound has a neuroprotective effect on neurons associated with the retina and retinal disease.

d. Clinical Trial Design (Treatment—Naïve, 6 Week Regimen)

Patients with newly diagnosed (e.g. treatment—naïve) subfoveal CNV that is secondary to wAMD are entered into a single-arm, open-label study. During each visit, patients are assessed for safety and tolerability. At specified visits, BCVA is determined by ETDRS and morphological evaluations are conducted utilizing SD-OCT and fundus photography/FA. The patients self-administer 800 mg per day p.o. (400 mg b.i.d.) of the investigational drug of the invention. The trial lasts 10 weeks, including 6 weeks of treatment plus 4 weeks of follow-up.

1. Primary Endpoint (BCVA)

The primary endpoint is the mean change in BCVA letter score as determined by the ETDRS (Early Treatment Diabetic Retinopathy Study) testing method. BCVA is measured during visits 1 (screening visit), 2-7 (treatment visits), 9-10 (follow-up visits).

2. Exploratory Endpoints (Morphological Changes)

Exploratory endpoints investigate ocular morphological effects related to b.i.d. administration of the investigational drug of the invention. Measurements of central retinal thickness (CRT), intraretinal fluid (IRF), subretinal fluid (SRF) and pigment epithelial detachment (PED) are all performed using SD-OCT and fundus photography/FA (fluorescein angiography).

e. Clinical Trial Design (Refractory wAMD, 6 Week Regimen)

Patients with refractory CNV secondary to wAMD following monthly treatment (for at least 3 months) with intravitreal (IVT) anti-vascular endothelial growth factor (anti-VEGR) therapeutics are entered into a single-arm, open-label study. During each visit, patients are assessed for safety and tolerability. At specified visits, BCVA is determined by ETDRS and morphological evaluations are conducted utilizing SD-OCT and fundus photography/FA. The patients self-administer 800 mg per day p.o. (400 mg b.i.d.) of the investigational drug of the invention. The trial lasts 10 weeks, including 6 weeks of treatment plus 4 weeks of follow-up.

1. Primary Endpoint (BCVA)

The primary endpoint is the mean change in BCVA letter score as determined by the ETDRS (Early Treatment Diabetic Retinopathy Study) testing method. BCVA is measured during visits 1 (screening visit), 2-7 (treatment visits), 9-10 (follow-up visits).

2. Exploratory Endpoints (Morphological Changes)

Exploratory endpoints investigate ocular morphological effects related to b.i.d. administration of the investigational drug of the invention. Measurements of central retinal thickness (CRT), intraretinal fluid (IRF), subretinal fluid (SRF) and pigment epithelial detachment (PED) are all performed using SD-OCT and fundus photography/FA (fluorescein angiography).

f. Combination Therapy Trial (Refractory wAMD, 1.5 Year Regimen)

Patients with newly diagnosed (e.g. treatment—naïve) subfoveal CNV that is secondary to wAMD are entered into a double-arm, randomized study. The first arm is comprised of anti-VEGF agent injection (e.g., a current standard of care, such as ranibizumab) delivered as an intravitreal injection plus the investigational drug of the invention administered orally. The second arm is comprised of anti-VEGF agent injection plus oral placebo (i.e., an active standard of care).

During each visit, patients are assessed for safety and tolerability. At specified visits, BCVA is determined by ETDRS and morphological evaluations are conducted utilizing SD-OCT and fundus photography/FA. The patients in the first arm self-administer 800 mg per day p.o. (400 mg b.i.d.) of the investigational drug of the invention and receive an anti-VEGF agent such as ranibizumab per visit injections at a dose of 10 mg/ml as 0.5 mg in a prefilled syringe. The patients in the second arm self-administer a placebo capsule twice day and receive an anti-VEGF agent such as ranibizumab as monthly injections at a dose of 10 mg/ml as 0.5 mg in a prefilled syringe.

1. Primary Endpoint (BCVA)

The primary endpoint is the mean change in BCVA letter score as determined by the ETDRS (Early Treatment Diabetic Retinopathy Study) testing method. BCVA is measured during screening visits, treatment visits of anti-VEGF agent and during follow-up visits. The mean change in BCVA between the two treatments groups is determined at 18 and 24 months.

2. Secondary Endpoints (Number of Injections)

The number of intravitreal injections per year administered in patients in the first treatment arm are determined. The two treatment arms are compared with those results to determine how many injections per year result in equivalent BCVA outcomes.

Additional endpoints investigate ocular morphological effects in each treatment arm. Measurements of central retinal thickness (CRT), intraretinal fluid (IRF), subretinal fluid (SRF) and pigment epithelial detachment (PED) are all performed using SD-OCT and fundus photography/FA (fluorescein angiography). These results then help to determine the degree of synergy between the anti-VEGF standard of care and the administration of the investigational drug of the invention, further elucidating comparisons in the mechanism of actions between the two therapies.

INCORPORATION BY REFERENCE

All publications, patents and patent applications mentioned in this specification are herein incorporated by reference to the same extent as if each individual publication or patent application was specifically and individually indicated to be incorporated by reference.

What is claimed:

1. A method of improving visual acuity in a subject diagnosed with a retina-associated disease, the method comprising orally administering to the subject a therapeutically effective amount of a compound of Formula 2:

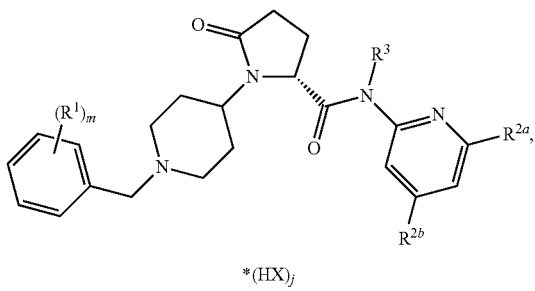

Formula 2 wherein:

A is $CH_2$, O or $N-C_{1-6}$-alkyl;

$R^1$ is $C_{1-6}$-alkyl, $C_{1-6}$-haloalkyl, $O-C_{1-6}$-haloalkyl, halogen;

m is 1, 2 or 3;

$R^{2a}$ and $R^{2b}$ are each independently selected from H, $C_{1-6}$-alkyl, $C_{2-6}$-alkenyl, $C_{2-6}$-alkynyl, $C_{3-6}$-cycloalkyl, COO—$C_{1-6}$-alkyl, O—$C_{1-6}$-alkyl, CONR$^{2b.1}$ R$^{2b.2}$, or halogen;

$R^{2b.1}$ is H, $C_{1-6}$-alkyl, $C_{0-4}$-alkyl-$C_{3-6}$-cycloalkyl, or $C_{1-6}$-haloalkyl;

$R^{2b.2}$ is H, or $C_{1-6}$-alkyl;

or $R^{2b.1}$ and $R^{2b.2}$ are together a $C_{3-6}$-alkylene group forming with the nitrogen atom a heterocyclic ring, wherein optionally one carbon atom of the ring is replaced by an oxygen atom $R^3$ is H, or $C_{1-6}$-alkyl;

X is an anion selected from the group consisting of chloride, bromide, iodide, sulphate, phosphate, methanesulphonate, nitrate, maleate, acetate, benzoate, citrate, salicylate, fumarate, tartrate, dibenzoyltartrate, oxalate, succinate, benzoate and p-toluenesulphonate; and j is 0, 0.5, 1, 1.5 or 2.

2. The method of claim 1, wherein
$R^{2a}$ is H, $C_{1-6}$-alkyl, $C_{2-6}$-alkenyl, $C_{2-6}$-alkynyl, $C_{3-6}$-cycloalkyl, O—$C_{1-6}$-alkyl, or CONR$^{2a.1}$R$^{2a.2}$;
$R^{2a.1}$ is H, $C_{1-6}$-alkyl, or $C_{1-6}$-haloalkyl;
$R^{2a.2}$ is H, or $C_{1-6}$-alkyl;
$R^{2b.1}$ is H, $C_{1-6}$-alkyl, $C_{2-6}$-alkenyl, $C_{2-6}$-alkynyl, $C_{3-6}$-cycloalkyl, COO—$C_{1-6}$-alkyl, O—$C_{1-6}$-alkyl, CONR$^{2b.1}$R$^{2b.2}$, or halogen;
$R^{2b.1}$ is H, $C_{1-6}$-alkyl, $C_{0-4}$-alkyl-$C_{3-6}$-cycloalkyl, or $C_{1-6}$-haloalkyl;
$R^{2b.2}$ is H, or $C_{1-6}$-alkyl;
or $R^{2b.1}$ and $R^{2b.2}$ are together a $C_{3-6}$-alkylene group forming with the nitrogen atom a heterocyclic ring, wherein optionally one carbon atom of the ring is replaced by an oxygen atom.

3. The method of claim 1, wherein
$R^1$ is $C_{1-6}$-alkyl, $C_{1-6}$-haloalkyl, O—$C_{1-6}$-haloalkyl, or halogen;
m is 1 or 2;
$R^{2a}$ is H, or $C_{1-4}$-alkyl;
$R^{2b}$ is H, or CONR$^{2b.1}$R$^{2b.2}$;
$R^{2b.1}$ is $C_{1-4}$-alkyl, $C_{0-4}$-alkyl-$C_{3-6}$-cycloalkyl, or $C_{1-4}$-haloalkyl;
$R^{2b.2}$ is H, or $C_{1-4}$-alkyl;
or $R^{2b.1}$ and $R^{2b.2}$ are together a $C_{3-6}$-alkylene group forming with the nitrogen atom a heterocyclic ring, wherein optionally one carbon atom of the ring is replaced by an oxygen atom
$R^3$ is H, or $C_{1-6}$-alkyl;
X is an anion selected from the group consisting of chloride or dibenzoyltartrate, and
j is 1 or 2.

4. The method of claim 1, wherein
$R^{2a}$ is H, or $C_{1-4}$-alkyl;
$R^{2b}$ is H, or CONR$^{2b.1}$R$^{2b.2}$;
  $R^{2b.1}$ is $C_{1-4}$-alkyl;
  $R^{2b.2}$ is $C_{1-4}$-alkyl.

5. The compound of claim 1, wherein
$R^{2a}$ is H, or $C_{1-4}$-alkyl;
$R^{2b}$ is H, or CONR$^{2b.1}$R$^{2b.2}$;
  $R^{2b.1}$ is $C_{0-4}$-alkyl-$C_{3-6}$-cycloalkyl;
  $R^{2b.2}$ is H, or $C_{1-4}$-alkyl.

6. The method of claim 1, wherein
$R^{2a}$ is H, or $C_{1-4}$-alkyl;
$R^{2b}$ is H, or CONR$^{2b.1}$R$^{2b.2}$;
  $R^{2b.1}$ is $C_{1-4}$-haloalkyl;
  $R^{2b.2}$ is H, $C_{1-4}$-alkyl.

7. The method of claim 1, wherein $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom.

8. The method of claim 1, wherein the compound Formula 2 is represented by the formula:

*(HX)$_j$ wherein j is 0.

9. The method of claim 1, wherein the compound of Formula 2 is a crystalline salt of formula:

*dibenzoyltartrate

10. The method of claim 1, wherein the compound of Formula 2 is a crystalline salt of formula:

*2 HCl

11. The method of claim 1, wherein the compound comprises a pharmaceutically acceptable carrier.

12. The method of claim 1, wherein the compound of Formula 2 is administered in the form of individual optical isomers, a mixture of the individual enantiomers, a racemate or in the form of the enantiomerically pure compounds.

13. The method of claim 1, wherein the compound comprises one or more compounds of the formula below,

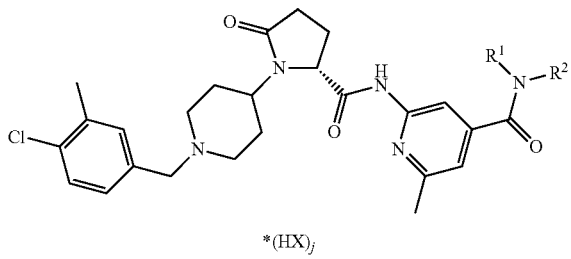

*(HX)$_j$ wherein

R$^1$ is H, C$_{1-6}$-alkyl, C$_{0-4}$-alkyl-C$_{3-6}$-cycloalkyl, or C$_{1-6}$-haloalkyl;

R$^2$ is H, or C$_{1-6}$-alkyl;

X is an anion selected from the group consisting of chloride or ½ dibenzoyltartrate; and j is 1 or 2, and the compound is administered in a pharmaceutical composition comprising a first diluent, a second diluent, a binder, a disintegrant and a lubricant.

14. The method of claim 13 characterized in that

R$^1$ is H, or methyl;

R$^2$ is H, or methyl;

X is an anion selected from the group consisting of chloride or ½ dibenzoyltartrate; and J is 1 or 2.

15. The method of claim 14, wherein X is chloride and j is 2.

16. The method of claim 15, wherein the pharmaceutical composition further comprises a buffering agent.

17. The method of claim 16, wherein the buffering agent comprises a basic amino acid.

18. The method of claim 17, wherein the basic amino acid is selected from L-arginine, L-lysine, L-histidine, or a combination thereof.

19. The method of claim 18, wherein the basic amino acid is L-arginine.

20. The method of claim 15, wherein the pharmaceutical composition further comprises
10-90% active ingredient
5-70% diluent 1,
5-30% diluent 2,
0-30% binder,
1-12% disintegrant, and
0.1-3% lubricant.

21. The method of claim 15, wherein the pharmaceutical composition further comprises
30-70% active ingredient
20-75% diluent 1,
5-30% diluent 2,
2-30% binder,
0.5-20% buffering agent,
1-12% disintegrant, and
0.1-3% lubricant.

22. The method of claim 15, wherein the pharmaceutical composition is a capsule, a tablet, or a film-coated tablet.

23. The method of claim 22, wherein the pharmaceutical composition further comprises a 2-4% film coat.

24. The method of claim 23, wherein the film coat comprises a film-forming agent, a plasticizer, a glidant, and optionally one or more pigments.

25. The method of claim 1, further comprising administering a therapeutically effective amount of an anti-VEGF therapy.

26. The method of claim 1, wherein the retina-associated disease is from the group consisting of dry age-related macular degeneration, wet age-related macular degeneration, central retinal vein occlusion, retinopathy of prematurity, and diabetic retinopathy.

* * * * *